(12) United States Patent
Zhuo et al.

(10) Patent No.: US 8,143,251 B2
(45) Date of Patent: *Mar. 27, 2012

(54) TRIAZOLOTRIAZINES AS KINASE INHIBITORS

(75) Inventors: Jincong Zhuo, Boothwyn, PA (US); Colin Zhang, Ambler, PA (US); Meizhong Xu, Hockessin, DE (US); Ding-Quan Qian, Newark, DE (US); Wenqing Yao, Kennett Square, PA (US); Ravi Kumar Jalluri, Avondale, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/033,918

(22) Filed: Feb. 24, 2011

(65) Prior Publication Data

US 2011/0144113 A1    Jun. 16, 2011

Related U.S. Application Data

(63) Continuation of application No. 12/695,636, filed on Jan. 28, 2010, now Pat. No. 7,915,408, which is a continuation of application No. 11/834,226, filed on Aug. 6, 2007, now Pat. No. 7,683,060.

(60) Provisional application No. 60/835,942, filed on Aug. 7, 2006, provisional application No. 60/861,931, filed on Nov. 30, 2006.

(51) Int. Cl.
*A61K 31/53* (2006.01)
*A61P 35/00* (2006.01)
*C07D 487/04* (2006.01)
*C07D 403/04* (2006.01)
*C07D 403/14* (2006.01)

(52) U.S. Cl. ........................ 514/243; 544/184
(58) Field of Classification Search .................. 544/184; 514/243

See application file for complete search history.

(56) References Cited

U.S. PATENT DOCUMENTS

| | | | |
|---|---|---|---|
| 2,837,520 A | 6/1958 | Fusco et al. | |
| 4,209,621 A | 6/1980 | Dusza et al. | |
| 4,405,619 A | 9/1983 | Heilman et al. | |
| 5,236,917 A | 8/1993 | Dunlap et al. | |
| 5,254,548 A | 10/1993 | Wermuth et al. | |
| 6,103,728 A | 8/2000 | Tang et al. | |
| 7,683,060 B2 * | 3/2010 | Zhuo et al. | 514/243 |
| 7,915,408 B2 * | 3/2011 | Zhuo et al. | 544/184 |
| 2005/0075340 A1 | 4/2005 | Zhang et al. | |
| 2005/0085473 A1 | 4/2005 | Van Hirschheydt et al. | |
| 2005/0165023 A1 | 7/2005 | Bettati | |
| 2005/0261297 A1 | 11/2005 | Igarashi et al. | |
| 2006/0046991 A1 | 3/2006 | Cui et al. | |
| 2006/0058303 A1 | 3/2006 | Chambers | |
| 2007/0191376 A1 | 8/2007 | Zou et al. | |
| 2008/0167287 A1 | 7/2008 | Zhuo et al. | |
| 2009/0124609 A1 | 5/2009 | Albrecht et al. | |
| 2009/0124612 A1 | 5/2009 | Albrecht et al. | |

FOREIGN PATENT DOCUMENTS

| | | |
|---|---|---|
| CA | 1246568 | 12/1988 |
| CA | 2158994 | 9/1994 |
| EP | 430385 | 6/1991 |
| EP | 443453 | 8/1996 |
| EP | 1640010 | 3/2006 |
| FR | 2662163 | 11/1991 |
| JP | 63037347 | 2/1988 |
| JP | 63199347 | 8/1988 |
| JP | 63310891 | 12/1988 |
| JP | 313934 | 1/1991 |
| JP | 4251243 | 9/1992 |
| JP | 5232618 | 9/1993 |
| JP | 2001043978 | 2/2001 |
| WO | WO 83/00864 | 3/1983 |
| WO | WO 96/40648 | 12/1996 |
| WO | WO 99/06404 | 2/1999 |
| WO | WO 01/34603 | 5/2001 |
| WO | WO 01/34605 | 5/2001 |
| WO | WO 02/00196 | 1/2002 |
| WO | WO 02/072579 | 9/2002 |
| WO | WO 02/079203 | 10/2002 |
| WO | WO 03/080621 | 10/2003 |
| WO | WO 03/087026 | 10/2003 |
| WO | WO 03/097641 | 11/2003 |
| WO | WO 2004/005290 | 1/2004 |
| WO | WO 2004/005291 | 1/2004 |
| WO | WO 2004/020438 | 3/2004 |
| WO | WO 2004/058769 | 7/2004 |
| WO | WO 2004/076412 | 9/2004 |
| WO | WO 2005/004607 | 1/2005 |
| WO | WO 2005/004808 | 1/2005 |
| WO | WO 2005/005378 | 1/2005 |
| WO | WO 2005/010005 | 2/2005 |
| WO | WO 2005/014598 | 2/2005 |

(Continued)

OTHER PUBLICATIONS

Abdel-Rahman, R. M.; Seada, M.; Fawzy, M.; El-Baz, Ibrahim, "Synthesis of some new thioethers of 1,2,4-triazine-3-hydrazones and assays for their anticancer and antihuman immune virus activities," Farmaco (1993), 48(3), 397-406, CODEN: FRMCE8; ISSN: 0014-827X.

Accornero et al., "An In vivo Model of Met-Driven Lymphoma as a Tool to Explore The Therapeutic Potential of Met Inhibitors", *Clin Cancer Res* 14(7):2220-26 (2008).

(Continued)

*Primary Examiner* — Venkataraman Balasubramanian
(74) *Attorney, Agent, or Firm* — Fish & Richardson P.C.

(57) ABSTRACT

The present invention is directed to [1,2,4]triazolo[4,3-b][1,2,4]triazines, and pharmaceutical compositions thereof, which are inhibitors of kinases such as c-Met and are useful in the treatment of cancer and other diseases related to the dysregulation of kinase pathways.

17 Claims, No Drawings

FOREIGN PATENT DOCUMENTS

| WO | WO 2005/028475 | 3/2005 |
|---|---|---|
| WO | WO 2005/030140 | 4/2005 |
| WO | WO 2005/039586 | 5/2005 |
| WO | WO 2005/040154 | 5/2005 |
| WO | WO 2005/040345 | 5/2005 |
| WO | WO 2005/070891 | 8/2005 |
| WO | WO 2005/073224 | 8/2005 |
| WO | WO 2005/077953 | 8/2005 |
| WO | WO 2005/097800 | 10/2005 |
| WO | WO 2005/113494 | 12/2005 |
| WO | WO 2005/121125 | 12/2005 |
| WO | WO 2006/014325 | 2/2006 |
| WO | WO 2006/018727 | 2/2006 |
| WO | WO 2006/124354 | 11/2006 |
| WO | WO 2007/008539 | 1/2007 |
| WO | WO 2007/013673 | 2/2007 |
| WO | WO 2007/015866 | 2/2007 |
| WO | WO 2007/025090 | 3/2007 |
| WO | WO 2007/064797 | 6/2007 |
| WO | WO 2007/075567 | 7/2007 |
| WO | WO 2007/096764 | 8/2007 |
| WO | WO 2008/008539 | 1/2008 |
| WO | WO 2008/051805 | 5/2008 |
| WO | WO 2008/058126 | 5/2008 |
| WO | WO 2008/144767 | 11/2008 |
| WO | WO 2009/091374 | 7/2009 |

OTHER PUBLICATIONS

Alarçon et al., "Unusual Ring Closure Reaction of Amides with Pyrimidines: Novel Stereoselective Synthesis of Hexahydroimidazo[1,2-c]pyrimidines." *Synthesis*, 12:2124-2130, 1999.

Balkovetz, Daniel, and Lipschutz, Joshua, "Hepatocyte Growth Factor and the Kidney: It Is Not Just for the Liver." *Intl. Rev. of Cytology*, 186:225-250, 1999.

Birchmeier et al., "Met, Metastasis, Motility, and More." *Nature*, 4:915-925, Dec. 2003.

Blom et al., "Preparative LC-MS Purification: Improved Compound-Specific Method Optimization." *J. Comb. Chem.*, 6:874-883, 2004.

Blume-Jensen, Peter, and Hunter, Tony, "Oncogenic kinase signaling." *Nature*, 411:355-365, May 17, 2001.

Boccaccio, Carla, and Comoglio, Paolo, "Invasive growth: a MET-driven genetic programme for cancer and stem cells." *Nature*, 6:637-645, Aug. 2006.

Bolen, Joseph, "Nonreceptor tyrosine protein kinases." *Oncogene*, 8(8):2025-2031, Aug. 1993.

Calic et al., "Flavonoids as Inhibitors of Lck and Fyn Kinases." *Croatica Chemical ACTA.*, 78(3):367-374, 2005.

Cecil, *Textbook of Medicine*, edited by Bennet and Plum, 20th edition, vol. 1, 1996, pp. 1004-1010.

Chattopadhyay et al., "Small Molecule c-Met Inhibitor PHA665752: Effect on Cell Growth and Motility in Papillary Thyroid Carcinoma", DOI: 10.1002/hed.v30:8, pp. 991-1000, Epub Mar. 7, 2008 in WileyInterScience (www.interscience.wiley.com); http://onlinelibrary.wiley.com/doi/10.1002/hed.20816/full.

Christensen et al., "A Selective Small Molecule Inhibitor of c-Met Kinase Inhibits c-Met Dependent Phenotypes In Vitro and Exhibits Cytoreductive Antitumor Activity In Vivo", *Cancer Res.* 63:7345-7355 (2003).

Christiansen et al., "c-Met as a target for human cancer and characterization of inhibitors for therapeutic intervention." *Cancer Letters*, 225:1-26, 2005.

Cohen, "The development and therapeutic potential of protein kinase inhibitors", *Current Opinion in Chemical Biology*, vol. 3, 1999, pp. 459-465.

Corso et al., "Cancer therapy: can the challenge be MET?" *Trends in Molecular Medicine*, 11(6):284-292, Jun. 2005.

Crestani et al., "Differential Role of Neutrophils and Aveolar Macrophages in Hepatocyte Growth Factor Production in Pulmonary Fibrosis." *Laboratory Investigation*, 82(8):1015-1022, Aug. 2002.

Dermer et al, "Another Anniversary for the War on Cancer", *BioTechnology*, vol. 12, Mar. 1994.

Druzhinin et al., "Acid-base Reactions of Imidazo[1,2-b]-1,2,4-Triazines (Imitrines) with Proton Donors." *Russian Journal of General Chemistry*, 63(6):953-958, 1993.

Eguchi et al., "Changes in liver regenerative factors in a case of living-related liver transplantation." *Clinical Transplantation*, 15:536-544, 1999.

Fabbro et al, "Protein kinases as targets for anticancer agents: from inhibitors to useful drugs", *Pharmacology & Therapeutics*, vol. 93, 2002, pp. 79-98.

Floyd, et al., "The Oxidation of Acetophenones to Arylglyoxals with Aqueous Hydrobromic Acid in Dimethyl Sulfoxide," *J. Org. Chem.*, 1985, 50, 5022-5027.

Freshney, "Culture of Animal Cells, A Manual of Basic Technique", Alan R, Liss, Inc., 1983, pp. 1-6.

Fusco, Raffaelo, and Rossi, Silvan, "Ricerche Sulle Triazine Assimetriche Sintesi Di Derivati Tetraziandenici," *Rendiconti*, 88:194-202, 1955, (CA 1956:56946, English abstract provided).

Futamatsu et al., "Autoimmune Myocarditis: A Potential Role for Induction of T Helper 2 Hepatocyte Growth Factor Ameliorates the Progression of Experimental Cytokines." *Circulation Research*, 96:823-830, 2005.

Garcia, et al., "Phase 1 study of ARQ 197, a selective inhibitor of the c-Met RTK in patients with metastatic solid tumors reaches recommended phase 2 dose", *Journal of Clinical Oncology*, 2007 ASCO Annual Meeting Proceedings Part I. vol. 25, No. 18S (Jun. 20 Supplement), 3525 (2007) (abstract only—2 pages).

Golub et al, "Molecular Classification of Cancer: Class Discovery and Class Prediction by Gene Expression Monitoring", *Science*, vol. 286, 1999, pp. 531-537.

Greene et al., *Protective Groups in Organic Synthesis*, 2d. Ed., Wiley & Sons, 1991*.

Greene et al., *Protective Groups in Organic Synthesis*, 4d. Ed., Wiley & Sons, 2007*.

Holla, B. Shivarama; Sarojini, B. K.; Rao, B.,Sooryanarayana; Poojary, Boja, "Synthesis and reactions of new N-bridged heterocycles derived from 3-substituted-4,5-diamino-1,2,4-triazoles," Indian Journal of Chemistry, Section B: Organic Chemistry Including Medicinal Chemistry (2003),42B(9), 2054-2058.

Jin et al., "MetMAb, the One-Armed 5D5 Anti-c-Met Antibody, Inhibits Orthotopic Pancreatic Tumor Growth and Improves Survival", Cancer Res 68(11):4360-68 (2008).

*Journal of Pharmaceutical Science*, 66, 2 (1977).

Kelly et al., "Synthesis of Cyclo-2,2':4',4''':2'',2''':4''',4'''':2'''',2''''':4''''',4-sexipyridine," *J. Org. Chem.* 1997, 62, 2774-2781.

Koblish, H.K. et al., "Preclinical in vivo characteristic of INCB028060, a novel, potent and highly selective c-Met inhibitor," *J. Clinical Oncology*,2008 ASCO Annual Meeting Proceedings (Post-Meeting Edition). vol. 26, No. 15S (May 20 Supplement), 2008: 14561.

Koch et al., "Hepatocyte Growth Factor." *Arthritis and Rheumatism*, 39(9):1566-1575, Sep. 1996.

Kong-Beltran et al., "Somatic Mutations Lead to an Oncogenic Deletion of Met in Lung Cancer", *Cancer Res.* 66(1):283-289 (2006).

Krayushkin, M. M.; Yarovenko, V. N.; Sedishev, I. P.; Zavarzin, I. V.; Vorontsova, L. G.; Starikova, Z. A., "Synthesis and Structure of 5-Indolyl-6-thienyl-1,2,4- Triazines," Russian Journal of Organic Chemistry (2005), 41(6), 875-883, CODEN: RJOCEQ; ISSN: 1070-4280.

Kruglenko et al., "Condensed Imidazo-1,2,4-azines. 28. Synthesis and Transformations of 2-Aroylmethyl-6,7-Diphenylimidazo-[1,2-b]-1,2,4-Triazin-4H-3-Ones." *Chemistry of Heterocyclic Compounds*, 34(2):232-236, 1998 (CA 129:302619, 1998, English abstract provided).

Labouta et al., "Potential Antineoplastics: Some Substituted Imidazo[1,2-b][1,2,4]triazines,[4,3-b][1,2,4]triazines and imidazotriazino-[5,6-b]indoles." *Journal of the Serbian Chemical Society*, 52(9):523-527, 1987. (CA 110-57624, 1989 English Abstract provided).

Labouta, Ibrahim M.; Eshba, Nabil H.; Salama, Hassan M., "Synthesis of some substituted triazolo[4,3-b][1,2,4]triazines as potential anticancer agents," Monatshefte fuer Chemie (1988), 119(5), 591-6, CODEN: MOCMB7; ISSN: 0026-9247.

Littke et al., "A Versatile Catalyst for Heck Reactions of Aryl Chlorides and Aryl Bromides under Mild Conditions," *J. Am. Chem. Soc.* 2001, 123, 6989-7000.

Liu, X. "Discovery and Characterization of INCB028060: A Novel, Potent and Selective MET RTK Inhibitor for Cancer Treatment," presentation at The AACR Annual Meeting, Apr. 12-16, 2008.

Liu, X, "INCB3028060 A Novel, Potent and Selective c-MET RTK Inhibitor for Cancer Treatment" presented at GTC Bio: The 4th Modern Drug Discovery & Development Summit, San Diego, CA, Oct. 15-17, 2008.

Liu, X., "Targeting the c-Met signaling pathway for cancer treatment," Expert Opin. Investig. Drugs (2008) 17(7) 997-1011.

Liu, Youhua, "Hepatocyte growth factor and the kidney." *Current Opinion in Nephrology and Hypertension*, 11:23-30, 2002.

Ma et al., "Hepatocyte growth factor is a survival factor for endothelial cells and is expressed in human atherosclerotic plaques." *Atherosclerosis*, 164:79-87, 2002.

Ma et al., "Functional Expression and Mutations of c-Met and Its Therapeutic Inhibition with SU11274 and Small Interfering RNA in Non-Small Cell Lung Cancer", *Cancer Res* 65(4):1479-88 (2005).

Ma et al., "Downstream signaling and specific inhibition of c-MET/HGF pathway in small cell lung cancer: implications for tumor invasion", *British J. Cancer*, 97:368-77 (2007).

Madhusudan, Srinivasan, and Ganesan, Trivadi, "Tyrosine kinase inhibitors in cancer therapy." *Clinical Biochemistry*, 37:618-635, 2004.

Manning et al., "The Protein Kinase Complement of the Human Genome." *Science*, 298:1912-1916, 1933-1934, Dec. 6, 2002.

Martens et al., "A Novel One-Armed Anti-c-Met Antibody Inhibits Glioblastoma Growth in vivo", *Clin Cancer Res* 12(20):6144-52 (2006).

Mass, "The Her Receptor Family: A Rich Target for Therapeutic Development", *International Journal Radiation Biol. Phys.*, vol. 51, No. 3, 2004, pp. 932-940.

Matsumoto, Kunio, and Nakamura, Toshikazu, "Hepatocyte growth factor: Renotropic role and potential therapeutics for renal diseases." *Kidney International*, 59:2023-2038, 2001.

Melpolder et al., "A Palladium-Catalyzed Arylation of Allylic Alcohols with Aryl Halides," *J. Org. Chem.*1976, 41, 265-272.

Miyaura et al., "Palladium-Catalyzed Cross-Coupling Reactions of Organoboron Compounds," *Chem. Rev.* 1995, 95, 2457-2483.

Miyazawa et al., "Protection of Hippocampal Neurons from Ischemia-induced Delayed Neuronal Death by Hepatocyte Growth Factor: A Novel Neurotrophic Factor." *Journal of Cerebral Blood Flow and Metabolism*, 18:345-348, 1998.

Morishita et al., "Therapeutic Angiogenesis using Hepatocyte Growth Factor (HGF)." *Current Gene Therapy*, 4:199-206, 2004.

Morishita et al., "Hepatocyte Growth Factor as Cardiovascular Hormone: Role of HGF in the Pathogenesis of Cardiovascular Disease." *Endocrine Journal*, 49(3):273-284, 2002.

Morotti et al., "K252a inhibits the oncogenic properties of Met, the HGF receptor", *Oncogene*, (2002) 21, pp. 4885-4893.

Mukohara et al., "Inhibition of the Met Receptor in Mesothelioma", *Clin Cancer Res* 11(22):8122-30 (2005).

Povstyanoi et al., Izvestiya Timiryazevskoi Sel'skokhozyaistvennoi Akademii (1984), (5), 155-9:(CA 102: 45885, 1985 (English Abstract provided).

Powell et al, "Groeth inhibition of psoriatic keratinocytes by quinazoline tyrosine kinase inhibitors", *British Journal of Dermatology*, 1999, vol. 141, pp. 802-810.

Puri et al., "c-Met Is a Potentially New Therapeutic Target for Treatment of Human Melanoma", *Clin Cancer Res* 13(7):2246-53 (2007).

*Remington's Pharmaceutical Sciences*, 17th ed., Mack Publishing Company, Easton, Pa., 1985, p. 1418.

Rossi, Silvano, and Trave, Roberto, "Pigmenti Fluorescenti derivati dall'1,4,7,9—tetraziandene." *La Chimica E L 'Industria*. 40(10):827-830, Oct. 1958. (CA 53-39972, 1959 English Abstract provided).

Sawada et al., "c-Met Overexpression Is a Prognostic Factor in Ovarian Cancer and an Effective Target for Inhibition of Peritoneal Dissemination and Invasion", *Cancer Res* 67(4):1670-79 (2007).

Segura-Flores et al., "Factor de crecimiento de hepatocitos (HGF) y sus aplicaciones terapeuticas." *Revista de Gastroenterologia de Mexico*, 69(4):243-250, Oct.-Dec. 2004.

Seiwert et al., "The MET Receptor Tyrosine Kinase Is a Potential Novel Therapeutic Target for Head and Neck Squamous Cell Carcinoma", *Cancer Res* 69(7):3021-31 (2009).

Smolen et al., "Amplification of MET may identify a subset of cancers with extreme sensitivity to the selective tyrosine kinase inhibitor PHA-665752", *PNAS*, vol. 103( 7):2316-21 (2006).

Soderquist and Negron, "Synthesis through the Interconverion of Methoxyboranes and Boron Hydrides: 9-BBN Systems," *J. Org. Chem.*, 1987, 52, 3441-3442.

Son et al., "Blockage of HGF/c-Met system by gene therapy (adenovirus-mediated NK4 gene) suppresses Hepatocellular carcinoma in mice", *J Hepatol.*, 45(5):688-95 (2006), Epub May 30, 2006.

Suffert et al., "Towards Molecular Electronics: A New Family of Aromatic Polymine Chelates Substituted with Alkyne Groups," *Tetrahedron Lett.* 1991, 32, 757.

T. Higuchi and V. Stella, "Pro-drugs as Novel Delivery Systems," vol. 14 of the A.C.S. Symposium Series Bioreversible Carriers in Drug Design, ed. Edward B. Roche, American Pharmaceutical Association and Pergamon Press, 1987*.

Taulli et al., "Validation of Met as a Therapeutic Target in Alveolar and Embryonal Rhabdomyosarcoma", *Cancer Res* 66(9):4742-49 (2006).

Tomchin A. B., Heterocyclic Semicarbazones and Thiosemicarbazones. XLV. 1,2,4-Triazinoindole Derivatives with a Condensed Imidazole, Thiazole, or Thiazole Ring.*Journal of Organic Chemistry of the USSR*, 18(6):1272-1280, Jun. 1982.

Vidal et al., "Effect of imidazo[1,2-a]pyrimidine derivatives on leukocyte function." *Inflammation Research*, 50:317-320, 2000.

Wang et al., "Potent and selective inhibitors of the Met [hepatocyte growth factor/scatter factor (HGF/SF) receptor] tyrosine kinase block HGF/SF-induced tumor cell growth and invasion." *Molecular Cancer Therapeutics*, 2:1085-1092, 2003.

Wermuth, Camille, "Molecular Variations Based on Isosteric Replacements." *The Practice of Medical Chemistry*, 203-237, 1996. XP002190259, chap. IID.

STN search report (Registry file compounds, Jul. 26, 2006).
STN search dated Oct. 16, 2006.
STN search report (Registry file compounds, Oct. 19, 2006).
STN search report (Registry file compounds, Nov. 1, 2006).
International Preliminary Report on Patentability for PCT/US2007/075254 dated Feb. 10, 2009.
International Search Report for PCT/US2007/075254 by Examiner Fazzi, Raffaella dated Jan. 9, 2008.
International Search Report for PCT/US2007/075254 dated Jan. 9, 2008.
International Preliminary Report on Patentability for PCT/US2007/085100 dated May 26, 2009.
International Search Report for PCT/US2007/085100 dated Apr. 11, 2008.
Office Action dated Mar. 27, 2009 for U.S. Appl. No. 11/942,130 (36 pgs.).
Reply to Office Action dated Mar. 27, 2009 for U.S. Appl. No. 11/942,130, filed on Jun. 26, 2009 (34 pgs.).
Response to Restriction Requirement dated Oct. 15, 2008 for U.S. Appl. No. 11/942,130, filed on Jan. 13, 2009 (27 pgs.).
Restriction Requirement dated Oct. 15, 2008 for U.S. Appl. No. 11/942,130 (6 pgs.).
Cheng, H. L. et al. Overexpression of c-met as a prognostic indicator for transitional cell carcinoma of the urinary bladder: a comparison with p53 nuclear accumulation. J Clin Oncol 20, 1544-50. (2002) (abstract only).
Koga F, Tsutsumi S, Neckers LM. Low dose geldanamycin inhibits hepatocyte growth factor and hypoxia-stimulated invasion of cancer cells. Cell Cycle. 6, 1393-402 (2007) (abstract only).
Arena S, Pisacane A, Mazzone M, Comoglio PM, Bardelli A. Genetic targeting of the kinase activity of the Met receptor in cancer cells. Proc Natl Acad Sci U S A. 104, 11412-7 (2007) (abstract only).
Tsai HW, Chow NH, Lin CP, Chan SH, Chou CY, Ho CL. The significance of prohibitin and c-Met/hepatocyte growth factor receptor in the progression of cervical adenocarcinoma. Hum Pathol. 37, 198-204. Epub Dec. 20, 2005 (2006) (abstract only).

Baykal, C., Ayhan, A., Al, A. & Yuce, K. Overexpression of the c-Met/HGF receptor and its prognostic significance in uterine cervix carcinomas. Gynecol Oncol 88, 123-9. (2003) (abstract only).

Leo C, Horn LC, Einenkel J, Hentschel B, Hockel M. Tumor hypoxia and expression of c-met in cervical cancer. Gynecol Oncol. 104, 181-5 (2007) (abstract only).

Leelawat K, Leelawat S, Tepaksorn P, Rattanasinganchan P, Leungchaweng A, Tohtong R, Sobhon P. Involvement of c-Met/hepatocyte growth factor pathway in cholangiocarcinoma cell invasion and its therapeutic inhibition with small interfering RNA specific for c-Met. J Surg Res. 136, 78-84 (2006) (abstract only).

Herynk, M.H. et al. Down-regulation of c-Met inhibits growth in the liver of human colorectal carcinoma cells. Cancer Res 63:2990-6 (2003) (abstract only).

Watson GA, Zhang X, Stang MT, Levy RM, Queiroz de Oliveira PE, Gooding WE, Christensen JG, Hughes SJ. Inhibition of c-Met as a therapeutic strategy for esophageal *Adenocarcinoma*. Neoplasia. 8, 949-55 (2006) (abstract only).

Tuynman JB, Lagarde SM, Ten Kate FJ, Richel DJ, van Lanschot JJ. Met expression is an independent prognostic risk factor in patients with *Oesophageal adenocarcinoma*. Br J Cancer. 98, 1102-8 (2008) (abstract only).

Knowles LM, Stabile LP, Egloff AM, Rothstein ME, Thomas SM, Gubish CT, Lerner EC, Seethala RR, Suzuki S, Quesnelle KM, Morgan S, Ferris RL, Grandis JR, Siegfried JM. HGF and c-Met participate in paracrine tumorigenic pathways in head and neck squamous cell cancer. Clin Cancer Res. 15, 3740-50 (2009) (abstract only).

Worden B, Yang XP, Lee TL, Bagain L, Yeh NT, Cohen JG, Van Waes C, Chen Z. Hepatocyte growth factor/scatter factor differentially regulates expression of proangiogenic factors through Egr-1 in head and neck squamous cell carcinoma. Cancer Res. 65, 7071-80 (2005) (abstract only).

Wang SY, Chen B, Zhan YQ, Xu WX, Li CY, Yang RF, Zheng H, Yue PB, Larsen SH, Sun HB, Yang X. SU5416 is a potent inhibitor of hepatocyte growth factor receptor (c-Met) and blocks HGF-induced invasiveness of human HepG2 hepatoma cells. J Hepatol 41, 267-73 (2004) (abstract only).

Son G, Hirano T, Seki E, Iimuro Y, Nukiwa T, Matsumoto K, Nakamura T, Fujimoto J. Blockage of HGF/c-Met system by gene therapy (adenovirus-mediated NK4 gene) suppresses hepatocellular carcinoma in mice. J Hepatol. 45, 688-95 (2006) (abstract only).

Qian, C. N. et al. Met protein expression level correlates with survival in patients with late-stage nasopharyngeal carcinoma. Cancer Res 62, 589-96 (2002) (abstract only).

Zhou HY, Wan KF, Ip CK, Wong CK, Mak NK, Lo KW, Wong AS. Hepatocyte growth factor enhances proteolysis and invasiveness of human nasopharyngeal cancer cells through activation of PI3K and JNK. FEBS Lett. 582, 3415-22 (2008) Epub Sep. 18, 2008 (abstract only).

Siraj AK, Bavi P, Abubaker J, Jehan Z, Sultana M, Al-Dayel F, Al-Nuaim A, Alzahrani A, Ahmed M, Al-Sana O, Uddin S, Al-Kuraya KS. Genome-wide expression analysis of Middle Eastern papillary thyroid cancer reveals c-MET as a novel target for cancer therapy. J Pathol. 213, 190-9 (2007) (abstract only).

Chattopadhyay C, El-Naggar AK, Williams MD, Clayman GL. Small molecule c-MET inhibitor PHA665752: effect on cell growth and motility in papillary thyroid carcinoma. Head Neck. 30, 991-1000 (2008) (abstract only).

Patane S, Avnet S, Coltella N, Costa B, Sponza S, Olivero M, Vigna E, Naldini L, Baldini N, Ferracini R, Corso S, Giordano S, Comoglio PM, Di Renzo MF. MET overexpression turns human primary osteoblasts into osteosarcomas. Cancer Res. 66, 4750-7 (2006) (abstract only).

Coltella N, Manara MC, Cerisano V, Trusolino L, Di Renzo MF, Scotlandi K, Ferracini R. Role of the MET/HGF receptor in proliferation and invasive behavior of osteosarcoma. FASEB J. 17, 1162-4 (2003) (abstract only).

Fukuda, T. et al. Coexpression of HGF and c-Met/HGF receptor in human bone and soft tissue tumors. Pathol Int 48, 757-62 (1998) (abstract only).

Kuhnen, C., Tolnay, E., Steinau, H. U., Voss, B. & Muller, K. M. Expression of c-Met receptor and hepatocyte growth factor/scatter factor in synovial sarcoma and epithelioid sarcoma. Virchows Arch 432, 337-42 (1998) (abstract only).

Oda, Y. et al. Expression of hepatocyte growth factor (HGF)/scatter factor and its receptor c-MET correlates with poor prognosis in synovial sarcoma. Hum Pathol 31, 185-92 (2002) (abstract only).

Morotti, A., Mila, S., Accornero, P., Tagliabue, E. & Ponzetto, C. K252a inhibits the oncogenic properties of Met, the HFG receptor. Oncogene 21, 4885-93 (2002) (abstract only).

Liang H, O'Reilly S, Liu Y, Abounader R, Laterra J, Maher VM, McCormick JJ. Sp1 regulates expression of MET, and ribozyme-induced down-regulation of MET in fibrosarcoma-derived human cells reduces or eliminates their tumorigenicity. Int J Oncol. 24, 1057-67 (2004) (abstract only).

Xie Q, Gao CF, Shinomiya N, Sausville E, Hay R, Gustafson M, Shen Y, Wenkert D, Vande Woude GF. Geldanamycins exquisitely inhibit HGF/SF-mediated tumor cell invasion. Oncogene 24, 3697-707 (2005) (abstract only).

Shinomiya N, Gao CF, Xie Q, Gustafson M, Waters DJ, Zhang YW, Vande Woude GF. RNA interference reveals that ligand-independent met activity is required for tumor cell signaling and survival. Cancer Res. 64, 7962-70 (2004) (abstract only).

Gao CF, Xie Q, Zhang YW, Su Y, Zhao P, Cao B, Furge K, Sun J, Rex K, Osgood T, Coxon A, Burgess TL, Vande Woude GF. Therapeutic potential of hepatocyte growth factor/scatter factor neutralizing antibodies: inhibition of tumor growth in both autocrine and paracrine hepatocyte growth factor/scatter factor:c-Met-driven models of leiomyosarcoma. Mol Cancer Ther. 8, 2803-10 (2009) (abstract only).

Montaldo, F. et al. Expression of functional tyrosine kinases on immortalized Kaposi's sarcoma cells. J Cell Physiol 184, 246-54 (2000) (abstract only).

Bardelli C, Sala M, Cavallazzi U, Prat M. Agonist Met antibodies define the signalling threshold required for a full mitogenic and invasive program of Kaposi's Sarcoma cells. Biochem Biophys Res Commun. 334, 1172-9 (2005) (abstract only).

Maier JA, Mariotti M, Albini A, Comi P, Prat M, Comogilio PM, Soria MR. Over-expression of hepatocyte growth factor in human Kaposi's sarcoma. Int J Cancer. 65, 168-72 (1996) (abstract only).

Hov H, Holt RU, Ro TB, Fagerli UM, Hjorth-Hansen H, Baykov V, Christensen JG, Waage A, Sundan A, Borset M. A selective c-met inhibitor blocks an autocrine hepatocyte growth factor growth loop in ANBL-6 cells and prevents migration and adhesion of myeloma cells. Clin Cancer Res 10, 6686-94 (2004) (abstract only).

Accornero P, Lattanzio G, Mangano T, Chiarle R, Taulli R, Bersani F, Forni PE, Miretti S, Scuoppo C, Dastrù W, Christensen JG, Crepaldi T, Ponzetto C. An in vivo model of Met-driven lymphoma as a tool to explore the therapeutic potential of Met inhibitors. Clin Cancer Res. 14, 2220-6 (2008) (abstract only).

Christensen JG, Zou HY, Arango ME, Li Q, Lee JH, McDonnell SR, Yamazaki S, Alton GR, Mroczkowski B, Los G. Cytoreductive antitumor activity of PF-2341066, a novel inhibitor of anaplastic lymphoma kinase and c-Met, in experimental models of anaplastic large-cell lymphoma. Mol Cancer Ther. 6, 3314-22 (2007) (abstract only).

Uddin S, Hussain AR, Ahmed M, Al-Dayel F, Bu R, Bavi P, Al-Kuraya KS. Inhibition of c-MET is a potential therapeutic strategy for treatment of diffuse large B-cell lymphoma. Lab Invest. 90, 1346-56 (2010) (abstract only).

Graveel CR, London CA, Vande Woude GF. A mouse model of activating Met mutations. Cell Cycle. 4, 518-20. Epub 2005 (2005) (abstract only).

Mahtouk K, Tjin EP, Spaargaren M, Pals ST. The HGF/MET pathway as target for the treatment of multiple myeloma and B-cell lymphomas. Biochim Biophys Acta. 1806, 208-19 (2010) (abstract only).

Choi YL, Tsukasaki K, O'Neill MC, Yamada Y, Onimaru Y, Matsumoto K, Ohashi J, Yamashita Y, Tsutsumi S, Kaneda R, Takada S, Aburatani H, Kamihira S, Nakamura T, Tomonaga M, Mano H. A genomic analysis of adult T-cell leukemia. Oncogene. 26, 1245-55 (2007) (abstract only).

Imaizumi, Y. et al. Expression of the c-Met proto-oncogene and its possible involvement in liver invasion in adult T-cell leukemia. Clin Cancer Res 9, 181-7 (2003) (abstract only).

Weimar, I. S. et al. Hepatocyte growth factor/scatter factor (HGF/SF) affects proliferation and migration of myeloid leukemic cells. Leukemia 12, 1195-203 (1998) (abstract only).

Verstovsek, S. et al. Plasma hepatocyte growth factor is a prognostic factor in patients with acute myeloid leukemia but not in patients with myelodysplastic syndrome. Leukemia 15, 1165-70. (2001) (abstract only).

Kim JG, Sohn SK, Kim DH, Baek JH, Lee NY, Suh JS, Chae SC, Lee KS, Lee KB. Clinical implications of angiogenic factors in patients with acute or chronic leukemia: hepatocyte growth factor levels have prognostic impact, especially in patients with acute myeloid leukemia. Leuk Lymphoma. 46, 885-91 (2005) (abstract only).

Zhelyazkova AG, Tonchev AB, Kolova P, Ivanova L, Gercheva L. Prognostic significance of hepatocyte growth factor and microvessel bone marrow density in patients with chronic myeloid leukaemia. Scand J Clin Lab Invest. 68, 492-500 (2008) (abstract only).

Moriyama T, Kataoka H, Koono M, Wakisaka S. Expression of hepatocyte growth factor/scatter factor and its receptor c-Met in brain tumors: evidence for a role in progression of astrocytic tumors (Review). Int J Mol Med. 3, 531-6 (1999) (abstract only).

Kunkel, P. et al. Expression and localization of scatter factor/hepatocyte growth factor in human astrocytomas. Neuro-oncol 3, 82-8 (2001) (abstract only).

Alami, J., Williams, B. R. & Yeger, H. Expression and localization of HGF and met in Wilms' tumours. J Pathol 196, 76-84. (2002) (abstract only).

Vuononvirta R, Sebire NJ, Messahel B, Perusinghe N, Reis-Filho JS, Pritchard-Jones K, Vujanic GM, Jones C. Expression of hepatocyte growth factor and its receptor met in Wilms' tumors and nephrogenic rests reflects their roles in kidney development. Clin Cancer Res. 15, 2723-30 (2009) (abstract only).

* cited by examiner

TRIAZOLOTRIAZINES AS KINASE INHIBITORS

CROSS-REFERENCE TO RELATED APPLICATIONS

This application is a continuation of U.S. Ser. No. 12/695,636, filed Jan. 28, 2010, now U.S. Pat. No. 7,915,408, which is a continuation of U.S. Ser. No. 11/834,226, filed Aug. 6, 2007, now U.S. Pat. No. 7,683,060, which claims the benefit of U.S. Prov. App. Ser. Nos. 60/835,942, filed Aug. 7, 2006 and 60/861,931, filed Nov. 30, 2006, the disclosures of which are incorporated herein by reference in their entireties.

FIELD OF THE INVENTION

The present invention is directed to [1,2,4]triazolo[4,3-b][1,2,4]triazines, and pharmaceutical compositions thereof, which are inhibitors of kinases such as c-Met and are useful in the treatment of cancer and other diseases related to the dysregulation of kinase pathways.

BACKGROUND OF THE INVENTION

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or substrates) and thereby modulating the cellular activities of the substrates in various biological contexts. In addition to the functions in normal tissues/organs, many protein kinases also play more specialized roles in a host of human diseases including cancer. A subset of protein kinases (also referred to as oncogenic protein kinases), when dysregulated, can cause tumor formation and growth, and further contribute to tumor maintenance and progression (Blume-Jensen P et al, Nature 2001, 411(6835):355-365). Thus far, oncogenic protein kinases represent one of the largest and most attractive groups of protein targets for cancer intervention and drug development.

Protein kinases can be categorized as receptor type and non-receptor type. Receptor tyrosine kinases (RTKs) have an extracellular portion, a transmembrane domain, and an intracellular portion, while non-receptor tyrosine kinases are entirely intracellular. RTK mediated signal transduction is typically initiated by extracellular interaction with a specific growth factor (ligand), typically followed by receptor dimerization, stimulation of the intrinsic protein tyrosine kinase activity, and receptor transphosphorylation. Binding sites are thereby created for intracellular signal transduction molecules and lead to the formation of complexes with a spectrum of cytoplasmic signaling molecules that facilitate the appropriate cellular response such as cell division, differentiation, metabolic effects, and changes in the extracellular microenvironment.

At present, at least nineteen (19) distinct RTK subfamilies have been identified. One RTK subfamily, designated the HER subfamily, includes EGFR, HER2, HER3 and HER4, and bind such ligands as epithelial growth factor (EGF), TGF-α, amphiregulin, HB-EGF, betacellulin and heregulin. A second family of RTKs, designated the insulin subfamily, includes the INS-R, the IGF-1R and the IR-R. A third family, the "PDGF" subfamily, includes the PDGF alpha and beta receptors, CSFIR, c-kit and FLK-II. Another subfamily of RTKs, referred to as the FLK subfamily, encompasses the Kinase insert Domain-Receptor fetal liver kinase-1 (KDR/FLK-1), the fetal liver kinase 4 (FLK-4) and the fms-like tyrosine kinase 1 (flt-1). Two other subfamilies of RTKs have been designated as the FGF receptor family (FGFR1, FGFR2, FGFR3 and FGFR4) and the Met subfamily (c-Met, Ron and Sea). For a detailed discussion of protein kinases, see for example, Blume-Jensen, P. et al., Nature. 2001, 411(6835): 355-365, and Manning, G. et al., Science. 2002, 298(5600): 1912-1934.

The non-receptor type of tyrosine kinases is also composed of numerous subfamilies, including Src, Btk, Abl, Fak, and Jak. Each of these subfamilies can be further subdivided into multiple members that have been frequently linked to oncogenesis. The Src family, for example, is the largest and includes Src, Fyn, Lck and Fgr among others. For a detailed discussion of these kinases, see Bolen J B. Nonreceptor tyrosine protein kinases. Oncogene. 1993, 8(8):2025-31.

A significant number of tyrosine kinases (both receptor and nonreceptor) are associated with cancer (see Madhusudan S, Ganesan T S. Tyrosine kinase inhibitors in cancer therapy. Clin Biochem. 2004, 37(7):618-35.). Clinical studies suggest that overexpression or dysregulation of tyrosine kinases may also be of prognostic value. For example, members of the HER family of RTKs have been associated with poor prognosis in breast, colorectal, head and neck and lung cancer. Mutation of c-Kit tyrosine kinase is associated with decreased survival in gastrointestinal stromal tumors. In acute myelogenous leukemia, Flt-3 mutation predicts shorter disease free survival. VEGFR expression, which is important for tumor angiogenesis, is associated with a lower survival rate in lung cancer. Tie-1 kinase expression inversely correlates with survival in gastric cancer. BCR-Abl expression is an important predictor of response in chronic myelogenous leukemia and Src tyrosine kinase is an indicator of poor prognosis in all stages of colorectal cancer.

c-Met, a proto-oncogene, is a member of a distinct subfamily of heterodimeric receptor tyrosine kinases which include Met, Ron, and Sea (Birchmeier, C. et al., Nat. Rev. Mol. Cell. Biol. 2003, 4(12):915-925; Christensen, J. G. et al., Cancer Lett. 2005, 225(1):1-26). The only high affinity ligand for c-Met is the hepatocyte growth factor (HGF), also known as scatter factor (SF). Binding of HGF to c-Met induces activation of the receptor via autophosphorylation resulting in an increase of receptor dependent signaling. Both c-Met and HGF are widely expressed in a variety of organs, but their expression is normally confined to the cells of epithelial and mesenchymal origin, respectively. The biological functions of c-Met (or c-Met signaling pathway) in normal tissues and human malignancies such as cancer have been well documented (Christensen, J. G. et al., Cancer Lett. 2005, 225(1): 1-26; Corso, S. et al., Trends in Mol. Med. 2005, 11(6):284-292).

HGF and c-Met are each required for normal mammalian development, and abnormalities reported in both HGF- and c-Met-null mice are consistent with proximity of embryonic expression and epithelial-mesenchymal transition defects during organ morphogenesis (Christensen, J. G. et al., Cancer Lett. 2005, 225(1):1-26). Consistent with these findings, the transduction of signaling and subsequent biological effects of HGF/c-Met pathway have been shown to be important for epithelial-mesenchymal interaction and regulation of cell migration, invasion, cell proliferation and survival, angiogenesis, morphogenesis and organization of three-dimensional tubular structures (e.g. renal tubular cells, gland formation) during development. The specific consequences of c-Met pathway activation in a given cell/tissue are highly context-dependent.

Dysregulated c-Met pathway plays important and sometimes causative (in the case of genetic alterations) roles in tumor formation, growth, maintenance and progression (Birchmeier, C. et al., Nat. Rev. Mol. Cell. Biol. 2003, 4(12): 915-925; Boccaccio, C. et al., Nat. Rev. Cancer 2006, 6(8): 637-645; Christensen, J. G. et al., Cancer Lett. 2005, 225(1): 1-26). HGF and/or c-Met are overexpressed in significant portions of most human cancers, and are often associated with poor clinical outcomes such as more aggressive disease, disease progression, tumor metastasis and shortened patient survival. Further, patients with high levels of HGF/c-Met proteins are more resistance to chemotherapy and radiotherapy. In addition to the abnormal HGF/c-Met expression, c-Met receptor can also be activated in cancer patients through genetic mutations (both germline and somatic) and gene amplification. Although gene amplification and mutations are the most common genetic alterations that have been reported in patients, the receptor can also be activated by deletions, truncations, gene rearrangement, as well as abnormal receptor processing and defective negative regulatory mechanisms.

The various cancers in which c-Met is implicated include, but are not limited to: carcinomas (e.g., bladder, breast, cervical, cholangiocarcinoma, colorectal, esophageal, gastric, head and neck, kidney, liver, lung, nasopharygeal, ovarian, pancreas, prostate, thyroid); musculoskeletal sarcomas (e.g., osteosarcaoma, synovial sarcoma, rhabdomyosarcoma); soft tissue sarcomas (e.g., MFH/fibrosarcoma, leiomyosarcoma, kaposi's sarcoma); hematopoietic malignancies (e.g., multiple myeloma, lymphomas, adult T cell leukemia, acute myelogenous leukemia, chronic myeloid leukemia); and other neoplasms (e.g., glioblastomas, astrocytomas, melanoma, mesothelioma and Wilm's tumor (www.vai.org/met/; Christensen, J. G. et al., Cancer Lett. 2005, 225(1):1-26).

The notion that the activated c-Met pathway contributes to tumor formation and progression and could be a good target for effective cancer intervention has been further solidified by numerous preclinical studies (Birchmeier, C. et al., Nat. Rev. Mol. Cell. Biol. 2003, 4(12):915-925; Christensen, J. G. et al., Cancer Lett. 2005, 225(1):1-26; Corso, S. et al., Trends in Mol. Med. 2005, 11(6):284-292). For example, studies showed that the tpr-met fusion gene, overexpression of c-met and activated c-met mutations all caused oncogenic transformation of various model cell lines and resulted in tumor formation and metastasis in mice. More importantly, significant anti-tumor (sometimes tumor regression) and anti-metastasis activities have been demonstrated in vitro and in vivo with agents that specifically impair and/or block HGF/c-Met signaling. Those agents include anti-HGF and anti-c-Met antibodies, HGF peptide antagonists, decoy c-Met receptor, c-Met peptide antagonists, dominant negative c-Met mutations, c-Met specific antisense oligonucleotides and ribozymes, and selective small molecule c-Met kinase inhibitors (Christensen, J. G. et al., Cancer Lett. 2005, 225(1):1-26).

In addition to the established role in cancer, abnormal HGF/c-Met signaling is also implicated in atherosclerosis, lung fibrosis, renal fibrosis and regeneration, liver diseases, allergic disorders, inflammatory and autoimmune disorders, cerebrovascular diseases, cardiovascular diseases, conditions associated with organ transplantation (Ma, H. et al., Atherosclerosis. 2002, 164(1):79-87; Crestani, B. et al., Lab. Invest. 2002, 82(8):1015-1022; Sequra-Flores, A. A. et al., Rev. Gastroenterol. Mex. 2004, 69(4)243-250; Morishita, R. et al., Curr. Gene Ther. 2004, 4(2)199-206; Morishita, R. et al., Endocr. J. 2002, 49(3)273-284; Liu, Y., Curr. Opin. Nephrol. Hypertens. 2002, 11(1):23-30; Matsumoto, K. et al., Kidney Int. 2001, 59(6):2023-2038; Balkovetz, D. F. et al., Int. Rev. Cytol. 1999, 186:225-250; Miyazawa, T. et al., J. Cereb. Blood Flow Metab. 1998, 18(4)345-348; Koch, A. E. et al., Arthritis Rheum. 1996, 39(9):1566-1575; Futamatsu, H. et al., Circ. Res. 2005, 96(8)823-830; Eguchi, S. et al., Clin. Transplant. 1999, 13(6)536-544).

Despite the important/causative roles that the c-Met pathway plays in the above described human diseases including cancer, there are no c-Met inhibitors or antagonists that are currently available for treating these human disorders that associate with abnormal HGF/c-Met signaling. Therefore, there is a clear unmet medical need to develop new compounds as inhibitors of c-Met kinase and other kinases. The compounds, compositions, and pharmaceutical methods provided herein help meet this need.

SUMMARY OF THE INVENTION

The present invention provides, inter alia, compounds having Formula I:

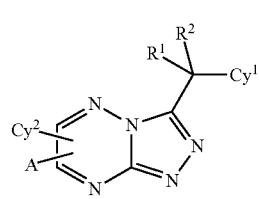

or pharmaceutically acceptable salts or prodrugs thereof, wherein constituent variables are provided herein.

The present invention further provides compositions comprising at least one compound of Formula I and at least one pharmaceutically acceptable carrier.

The present invention further provides methods of inhibiting activity of a receptor or non-receptor tyrosine kinase by contacting the kinase with a compound of Formula I, or pharmaceutically acceptable salt thereof.

The present invention further provides methods of inhibiting the HGF/c-Met kinase signaling pathway in a cell by contacting the cell with a compound of Formula I, or pharmaceutically acceptable salt thereof.

The present invention further provides methods of inhibiting the proliferative activity of a cell by contacting the cell with a compound of Formula I, or pharmaceutically acceptable salt thereof.

The present invention further provides methods of inhibiting tumor growth in a patient by administering to the patient a therapeutically effective amount of a compound of Formula I, or pharmaceutically acceptable salt thereof.

The present invention further provides methods of inhibiting tumor metastasis in a patient comprising administering to the patient a therapeutically effective amount of a compound of Formula I, or pharmaceutically acceptable salt thereof.

The present invention further provides methods of treating a disease in a patient, wherein the disease is associated with dysregulation of the HGF/c-MET signaling pathway, by administering to the patient a therapeutically effective amount of a compound of Formula I, or pharmaceutically acceptable salt thereof.

The present invention further provides methods of treating cancer in a patient by administering to the patient a therapeutically effective amount of a compound of Formula I, or pharmaceutically acceptable salt thereof.

DETAILED DESCRIPTION

The present invention provides, inter alia, compounds that are inhibitors of kinases, including receptor tyrosine kinases such as those of the Met subfamily, having Formula I:

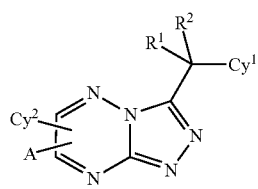

I or pharmaceutically acceptable salts or prodrugs thereof, wherein:

$Cy^1$ is aryl, heteroaryl, cycloalkyl, or heterocycloalkyl, each optionally substituted by 1, 2, 3, 4, or 5 —W—X—Y—Z;

$Cy^2$ is aryl, heteroaryl, cycloalkyl, or heterocycloalkyl, each optionally substituted by 1, 2, 3, 4, or 5 —W'—X'—Y'—Z';

A is H, halo, $C_{1-6}$ alkyl, $C_{2-6}$ alkenyl, $C_{2-6}$ alkynyl, $C_{1-6}$ haloalkyl, CN, $NO_2$, $OR^A$, $SR^A$, $C(O)R^B$, $C(O)NR^CR^D$, $C(O)OR^A$, $OC(O)R^B$, $OC(O)NR^CR^D$, $NR^CR^D$, $NR^CC(O)R^B$, $NR^CC(O)NR^CR^D$, $NR^CC(O)OR^A$, $S(O)R^B$, $S(O)NR^CR^D$, $S(O)_2R^B$, $NR^CS(O)_2R^B$, or $S(O)_2NR^CR^D$;

$R^1$ and $R^2$ together with the carbon atom to which they are attached form a 3- to 7-membered cycloalkyl group or 3- to 7-membered heterocycloalkyl group, each optionally substituted by 1, 2, 3, 4, or 5 substituents independently selected from Q, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$, wherein said $C_{1-6}$ alkyl, $C_{2-6}$ alkenyl, and $C_{2-6}$ alkynyl is optionally substituted with 1, 2, or 3 substituents selected from Q, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$;

Q is aryl, heteroaryl, cycloalkyl, or heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

W and W' are independently absent or independently selected from $C_{1-6}$ alkylene, $C_{2-6}$ alkenylene, $C_{2-6}$ alkynylene, O, S, $NR^h$, CO, COO, $CONR^h$, SO, $SO_2$, $SONR^h$ and $NR^hCONR^i$, wherein each of the $C_{1-6}$ alkylene, $C_{2-6}$ alkenylene, and $C_{2-6}$ alkynylene is optionally substituted by 1, 2 or 3 substituents independently selected from halo, $C_{1-6}$ alkyl, $C_{1-6}$ haloalkyl, OH, $C_{1-6}$ alkoxy, $C_{1-6}$ haloalkoxy, amino, $C_{1-6}$ alkylamino, and $C_{2-8}$ dialkylamino;

X and X' are independently absent or independently selected from $C_{1-6}$ alkylene, $C_{2-6}$ alkenylene, $C_{2-6}$ alkynylene, arylene, cycloalkylene, heteroarylene, and heterocycloalkylene, wherein each of the $C_{1-6}$ alkylene, $C_{2-6}$ alkenylene, $C_{2-6}$ alkynylene, arylene, cycloalkylene, heteroarylene, and heterocycloalkylene is optionally substituted by 1, 2 or 3 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^j$, $C(O)NR^hR^i$, amino, $C_{1-6}$ alkylamino, and $C_{2-8}$ dialkylamino;

Y and Y' are independently absent or independently selected from $C_{1-6}$ alkylene, $C_{2-6}$ alkenylene, $C_{2-6}$ alkynylene, O, S, $NR^h$, CO, COO, $CONR^h$, SO, $SO_2$, $SONR^h$, and $NR^hCONR^i$, wherein each of the $C_{1-6}$ alkylene, $C_{2-6}$ alkenylene, and $C_{2-6}$ alkynylene is optionally substituted by 1, 2 or 3 substituents independently selected from halo, $C_{1-6}$ alkyl, $C_{1-6}$ haloalkyl, OH, $C_{1-6}$ alkoxy, $C_{1-6}$ haloalkoxy, amino, $C_{1-6}$ alkylamino, and $C_{2-8}$ dialkylamino;

Z and Z' are independently selected from H, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $S(O)R^{b2}$, $S(O)NR^{c2}R^{d2}$, $S(O)_2R^{b2}$, $NR^{c2}S(O)_2R^{b2}$, $S(O)_2NR^{c2}R^{d2}$, aryl, cycloalkyl, heteroaryl, and heterocycloalkyl, wherein said $C_{1-6}$ alkyl, $C_{2-6}$ alkenyl, $C_{2-6}$ alkynyl, aryl, cycloalkyl, heteroaryl, and heterocycloalkyl are optionally substituted by 1, 2, 3, 4 or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

wherein two adjacent —W—X—Y—Z, together with the atoms to which they are attached, optionally form a fused 4-, 5-, 6-, or 7-membered cycloalkyl ring or a fused 4-, 5-, 6-, or 7-membered heterocycloalkyl ring, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $S(O)R^{b2}$, $S(O)NR^{c2}R^{d2}$, $S(O)_2R^{b2}$, $NR^{c2}S(O)_2R^{b2}$, $S(O)_2NR^{c2}R^{d2}$, aryl, cycloalkyl, heteroaryl, and heterocycloalkyl;

wherein two adjacent —W'—X'—Y'—Z', together with the atoms to which they are attached, optionally form a fused 4-, 5-, 6-, or 7-membered cycloalkyl ring or a fused 4-, 5-, 6-, or 7-membered heterocycloalkyl ring, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $S(O)R^{b2}$, $S(O)NR^{c2}R^{d2}$, $S(O)_2R^{b2}$, $NR^{c2}S(O)_2R^{b2}$, $S(O)_2NR^{c2}R^{d2}$, aryl, cycloalkyl, heteroaryl, and heterocycloalkyl;

$R^A$ is H, $C_{1-4}$ alkyl, $C_{2-4}$ alkenyl, or $C_{2-4}$ alkynyl, wherein said $C_{1-4}$ alkyl, $C_{2-4}$ alkenyl, or $C_{2-4}$ alkynyl, is optionally substituted with 1, 2, or 3 substituents independently selected from OH, CN, amino, halo, and $C_{1-4}$ alkyl;

$R^B$ is H, $C_{1-4}$ alkyl, $C_{2-4}$ alkenyl, or $C_{2-4}$ alkynyl, wherein said $C_{1-4}$ alkyl, $C_{2-4}$ alkenyl, or $C_{2-4}$ alkynyl, is optionally substituted with 1, 2, or 3 substituents independently selected from OH, CN, amino, halo, and $C_{1-4}$ alkyl;

$R^C$ and $R^D$ are independently selected from H, $C_{1-4}$ alkyl, $C_{2-4}$ alkenyl, or $C_{2-4}$ alkynyl, wherein said $C_{1-4}$ alkyl, $C_{2-4}$ alkenyl, or $C_{2-4}$ alkynyl, is optionally substituted with 1, 2, or 3 substituents independently selected from OH, CN, amino, halo, and $C_{1-4}$ alkyl;

or $R^C$ and $R^D$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, and $C_{1-4}$ alkyl;

$R^a$, $R^{a1}$, $R^{a2}$, are $R^{a3}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^b$, $R^{b1}$, $R^{b2}$, and $R^{b3}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^c$ and $R^d$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^c$ and $R^d$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{c1}$ and $R^{d1}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c1}$ and $R^{d1}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{c2}$ and $R^{d2}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl are each optionally substituted with 1, 2, or 3 substituents independently selected from OH, CN, amino, halo, $C_{1-6}$ alkyl, $C_{1-6}$ alkoxy, $C_{1-6}$ haloalkyl, $C_{1-6}$ haloalkoxy, hydroxyalkyl, cyanoalkyl, aryl, heteroaryl, $C(O)OR^{a3}$, $C(O)R^{b3}$, $S(O)_2R^{b3}$, alkoxyalkyl, and alkoxyalkoxy;

or $R^{c2}$ and $R^{d2}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, $C_{1-6}$ haloalkoxy, hydroxyalkyl, cyanoalkyl, aryl, heteroaryl, $C(O)OR^{a3}$, $C(O)R^{b3}$, $S(O)_2R^{b3}$, alkoxyalkyl, and alkoxyalkoxy.

$R^e$ is H, $C_{1-6}$ alkyl, $C_{1-6}$ haloalkyl, $C_{2-6}$ alkenyl, ($C_{1-6}$ alkoxy)-$C_{1-6}$ alkyl, $C_{2-6}$ alkynyl, aryl, cycloalkyl, heteroaryl, heterocycloalkyl, arylalkyl, cycloalkylalkyl, heteroarylalkyl, or heterocycloalkylalkyl;

$R^f$ is H, $C_{1-6}$ alkyl, $C_{1-6}$ haloalkyl, $C_{2-6}$ alkenyl, $C_{2-6}$ alkynyl, aryl, cycloalkyl, heteroaryl, or heterocycloalkyl;

$R^g$, $R^{g1}$, and $R^{g2}$ are independently selected from H, CN, and $NO_2$;

$R^h$ and $R^i$ are independently selected from H and $C_{1-6}$ alkyl; and $R^j$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl.

In some embodiments, $Cy^1$ is aryl or heteroaryl, each optionally substituted by 1, 2, 3, 4, or 5 —W—X—Y—Z.

In some embodiments, $Cy^1$ is aryl or heteroaryl, each optionally substituted by 1, 2, 3, 4, or 5 —Z.

In some embodiments, $Cy^1$ is aryl or heteroaryl, each optionally substituted by 1, 2, or 3 substituents independently selected from halo, $C_{1-4}$ alkyl, $C_{1-4}$ haloalkyl, OH, and $C_{1-4}$ alkoxy.

In some embodiments, $Cy^1$ is phenyl or quinolinyl, each optionally substituted by 1, 2, 3, 4, or 5 —W—X—Y—Z.

In some embodiments, $Cy^1$ is phenyl optionally substituted by 1, 2, 3, 4, or 5 —W—X—Y—Z.

In some embodiments, $Cy^1$ is quinolinyl optionally substituted by 1, 2, 3, 4, or 5 —W—X—Y—Z.

In some embodiments, $Cy^1$ is quinolinyl.

In some embodiments, $Cy^2$ is aryl or heteroaryl, each optionally substituted by 1, 2, 3, 4, or 5 —W'—X'—Y'—Z'.

In some embodiments, $Cy^2$ is phenyl optionally substituted by 1, 2, 3, 4, or 5 —W'—X'—Y'—Z'.

In some embodiments, $Cy^2$ is phenyl optionally substituted by 1, 2, 3, 4, or 5 —Z'.

In some embodiments, $Cy^2$ is phenyl optionally substituted by 1, 2, 3, 4, or 5 —$CONR^h$—X'—Y'—Z'.

In some embodiments, A is H, halo, $C_{1-6}$ alkyl, $C_{1-6}$ haloalkyl, CN, $NO_2$, $OR^A$, or $NR^CR^D$.

In some embodiments, A is H or $NR^CR^D$.

In some embodiments, $R^1$ and $R^2$ together with the carbon atom to which they are attached form a 3- to 7-membered cycloalkyl group optionally substituted by 1, 2, 3, 4, or 5 substituents independently selected from Q, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$, wherein said $C_{1-6}$ alkyl, $C_{2-6}$ alkenyl, and $C_{2-6}$ alkynyl is optionally substituted with 1, 2, or 3 substituents selected from Q, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, P(R$^f$)$_2$, P(OR$^e$)$_2$, P(O)R$^e$R$^f$, P(O)OR$^e$OR$^f$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, R$^1$ and R$^2$ together with the carbon atom to which they are attached form a cyclopropyl group optionally substituted by 1, 2, 3, 4, or 5 substituents independently selected from Q, halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, P(R$^f$)$_2$, P(OR$^e$)$_2$, P(O)R$^e$R$^f$, P(O)OR$^e$OR$^f$, S(O)R$^b$, S(O)NR$^c$R$^d$, S(O)$_2$R$^b$, NR$^c$S(O)$_2$R$^b$, and S(O)$_2$NR$^c$R$^d$, wherein said C$_{1-6}$ alkyl, C$_{2-6}$ alkenyl, and C$_{2-6}$ alkynyl is optionally substituted with 1, 2, or 3 substituents selected from Q, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, P(R$^f$)$_2$, P(OR$^e$)$_2$, P(O)R$^e$R$^f$, P(O)OR$^e$OR$^f$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, R$^1$ and R$^2$ together with the carbon atom to which they are attached form a 3- to 7-membered cycloalkyl group.

In some embodiments, R$^1$ and R$^2$ together with the carbon atom to which they are attached form a cyclopropyl group.

In some embodiments, Q is aryl, heteroaryl, cycloalkyl, or heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^{g1}$)NR$^{c1}$R$^{d1}$, NR$^{c1}$C(=NR$^{gi}$)NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, and S(O)$_2$NR$^{c1}$R$^{d1}$.

In some embodiments, W is CONR$^h$.

In some embodiments, —W—X—Y—Z is H, halo, C$_{1-6}$ alkyl, C$_{2-6}$ alkenyl, C$_{2-6}$ alkynyl, C$_{1-6}$ haloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^{g2}$)NR$^{c2}$R$^{d2}$, NR$^{c2}$C(=NR$^{g2}$)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, S(O)$_2$NR$^{c2}$R$^{d2}$, aryl, cycloalkyl, heteroaryl, and heterocycloalkyl, wherein said C$_{1-6}$ alkyl, C$_{2-6}$ alkenyl, C$_{2-6}$ alkynyl, aryl, cycloalkyl, heteroaryl, and heterocycloalkyl are optionally substituted by 1, 2, 3, 4 or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^{g2}$)NR$^{c2}$R$^{d2}$, NR$^{c2}$C(=NR$^{g2}$)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$.

In some embodiments, —W—X—Y—Z is H, halo, C$_{1-6}$ alkyl, C$_{1-6}$ haloalkyl, CN, NO$_2$, OR$^{a2}$, C(O)R$^{b2}$, C(O)NR$^{c2}$R$^{d2}$, C(O)OR$^{a2}$, S(O)R$^{b2}$, S(O)NR$^{c2}$R$^{d2}$, S(O)$_2$R$^{b2}$, NR$^{c2}$S(O)$_2$R$^{b2}$, S(O)$_2$NR$^{c2}$R$^{d2}$, aryl, cycloalkyl, heteroaryl, and heterocycloalkyl, wherein said C$_{1-6}$ alkyl, C$_{2-6}$ aryl, cycloalkyl, heteroaryl, and heterocycloalkyl are optionally substituted by 1, 2, 3, 4 or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^{g2}$)NR$^{c2}$R$^{d2}$, NR$^{c2}$C(=NR$^{g2}$)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$.

In some embodiments, —W—X—Y—Z is H, halo, C$_{1-6}$ alkyl, C$_{1-6}$ haloalkyl, CN, NO$_2$, OR$^{a2}$, C(O)R$^{b2}$, C(O)NR$^{c2}$R$^{d2}$, C(O)OR$^{a2}$, S(O)R$^{b2}$, S(O)NR$^{c2}$R$^{d2}$, S(O)$_2$R$^{b2}$, NR$^{c2}$S(O)$_2$R$^{b2}$, S(O)$_2$NR$^{c2}$R$^{d2}$, aryl, cycloalkyl, heteroaryl, and heterocycloalkyl, wherein said C$_{1-6}$ alkyl, C$_{2-6}$ aryl, cycloalkyl, heteroaryl, and heterocycloalkyl are optionally substituted by 1, 2, 3, 4 or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^{g2}$)NR$^{c2}$R$^{d2}$, NR$^{c2}$C(=NR$^{g2}$)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$.

In some embodiments, —W—X—Y—Z is H, halo, C$_{1-6}$ alkyl, C$_{1-6}$ haloalkyl, CN, NO$_2$, OR$^{a2}$, C(O)R$^{b2}$, and C(O)NR$^{c2}$R$^{d2}$, wherein said C$_{1-6}$ alkyl is optionally substituted by 1, 2, 3, 4 or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^{g2}$)NR$^{c2}$R$^{d2}$, NR$^{c2}$C(=NR$^{g2}$)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$.

In some embodiments, —W—X—Y—Z is H, halo, C$_{1-6}$ alkyl, C$_{1-6}$ haloalkyl, CN, NO$_2$, OR$^{a2}$, C(O)R$^{b2}$, and C(O)NR$^{c2}$R$^{d2}$.

In some embodiments, at least one —W—X—Y—Z is C(O)NR$^{c2}$R$^{d2}$.

In some embodiments, —W'—X'—Y'—Z' is H, halo, C$_{1-6}$ alkyl, C$_{2-6}$ alkenyl, C$_{2-6}$ alkynyl, C$_{1-6}$ haloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^{g2}$)NR$^{c2}$R$^{d2}$, NR$^{c2}$C(=NR$^{g2}$)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, S(O)$_2$NR$^{c2}$R$^{d2}$, aryl, cycloalkyl, heteroaryl, and heterocycloalkyl, wherein said C$_{1-6}$ alkyl, C$_{2-6}$ alkenyl, C$_{2-6}$ alkynyl, aryl, cycloalkyl, heteroaryl, and heterocycloalkyl are optionally substituted by 1, 2, 3, 4 or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^{g2}$)NR$^{c2}$R$^{d2}$, NR$^{c2}$C(=NR$^{g2}$)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$.

In some embodiments, —W'—X'—Y'—Z' is H, halo, C$_{1-6}$ alkyl, C$_{1-6}$ haloalkyl, CN, NO$_2$, OR$^{a2}$, C(O)R$^{b2}$, C(O)NR$^{c2}$R$^{d2}$, C(O)OR$^{a2}$, S(O)R$^{b2}$, S(O)NR$^{c2}$R$^{d2}$, S(O)$_2$R$^{b2}$, NR$^{c2}$S(O)$_2$R$^{b2}$, S(O)$_2$NR$^{c2}$R$^{d2}$, aryl, cycloalkyl, heteroaryl, and heterocycloalkyl, wherein said C$_{1-6}$ alkyl, C$_{2-6}$ aryl, cycloalkyl, heteroaryl, and heterocycloalkyl are optionally substituted by 1, 2, 3, 4 or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^{g2}$)NR$^{c2}$R$^{d2}$, NR$^{c2}$C(=NR$^{g2}$)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$.

In some embodiments, —W'—X'—Y'—Z' is H, halo, C$_{1-6}$ alkyl, C$_{1-6}$ haloalkyl, CN, NO$_2$, OR$^{a2}$, C(O)R$^{b2}$, C(O)NR$^{c2}$R$^{d2}$, C(O)OR$^{a2}$, S(O)R$^{b2}$, S(O)NR$^{c2}$R$^{d2}$, S(O)$_2$R$^{b2}$, NR$^{c2}$S(O)$_2$R$^{b2}$, S(O)$_2$NR$^{c2}$R$^{d2}$, aryl, cycloalkyl, heteroaryl, and heterocycloalkyl, wherein said C$_{1-6}$ alkyl, C$_{2-6}$ aryl, cycloalkyl, heteroaryl, and heterocycloalkyl are optionally substituted by 1, 2, 3, 4 or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

In some embodiments, —W'—X'—Y'—Z' is H, halo, $C_{1-6}$ alkyl, $C_{1-6}$ haloalkyl, CN, $NO_2$, $OR^{a2}$, $C(O)R^{b2}$, and $C(O)NR^{c2}R^{d2}$, wherein said $C_{1-6}$ alkyl is optionally substituted by 1, 2, 3, 4 or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

In some embodiments, —W'—X'—Y'—Z' is H, halo, $C_{1-6}$ alkyl, $C_{1-6}$ haloalkyl, CN, $NO_2$, $OR^{a2}$, $C(O)R^{b2}$, and $C(O)NR^{c2}R^{d2}$.

In some embodiments, at least one —W'—X'—Y'—Z' is $C(O)NR^{c2}R^{d2}$.

In some embodiments, $R^{c2}$ and $R^{d2}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c2}$ and $R^{d2}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy.

In some embodiments, Z and Z' are independently selected from H, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $S(O)R^{b2}$, $S(O)NR^{c2}R^{d2}$, $S(O)_2R^{b2}$, $NR^{c2}S(O)_2R^{b2}$, $S(O)_2NR^{c2}R^{d2}$, aryl, cycloalkyl, heteroaryl, and heterocycloalkyl, wherein said $C_{1-6}$ alkyl, $C_{2-6}$ alkenyl, $C_{2-6}$ alkynyl, aryl, cycloalkyl, heteroaryl, and heterocycloalkyl are optionally substituted by 1, 2, 3, 4 or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

In some embodiments, the compounds of the invention have Formula II:

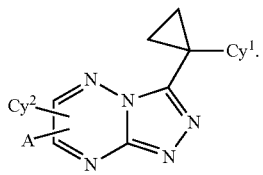

II

In some embodiments, the compounds of the invention have Formula IIIa or IIIb:

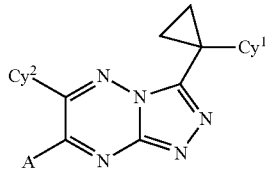

IIIa

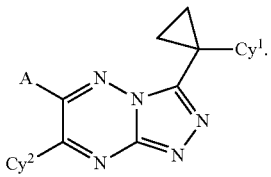

IIIb

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, the term "alkylene" refers to a linking alkyl group.

As used herein, "alkenyl" refers to an alkyl group having one or more double carbon-carbon bonds. Example alkenyl groups include ethenyl, propenyl, and the like.

As used herein, "alkenylene" refers to a linking alkenyl group.

As used herein, "alkynyl" refers to an alkyl group having one or more triple carbon-carbon bonds. Example alkynyl groups include ethynyl, propynyl, and the like.

As used herein, "alkynylene" refers to a linking alkynyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "arylene" refers to a linking aryl group.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of pentane, pentene, hexane, and the like. A cycloalkyl group having one or more fused aromatic rings can be attached though either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like.

As used herein, "cycloalkylene" refers to a linking cycloalkyl group.

As used herein, a "heteroaryl" group refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heteroarylene" refers to a linking heteroaryl group.

As used herein, "heterocycloalkyl" refers to a non-aromatic heterocycle where one or more of the ring-forming atoms is a heteroatom such as an O, N, or S atom. Heterocycloalkyl groups can include mono- or polycyclic (e.g., having 2, 3 or 4 fused rings) ring systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the non-aromatic heterocyclic ring, for example phthalimidyl, naphthalimidyl, and benzo derivatives of heterocycles such as indolene and isoindolene groups. A heterocycloalkyl group having one or more fused aromatic rings can be attached though either the aromatic or non-aromatic portion. In some embodiments, the carbon atoms or heteroatoms in the heterocyclyl or heterocycle ring can be oxidized (to form, e.g., a carbonyl, sulfinyl, sulfonyl, or other oxidized nitrogen or sulfur linkage) or a nitrogen atom can be quaternized. In some embodiments, the heterocycloalkyl group has from 1 to about 20 carbon atoms, and in further embodiments from about 3 to about 20 carbon atoms. In some embodiments, the heterocycloalkyl group contains 3 to about 20, 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "heterocycloalkylene" refers to a linking heterocycloalkyl group.

As used herein, "heterocycloalkylene" refers to a linking heterocycloalkyl group.

As used herein, "arylcycloalkyl" refers to cycloalkyl group substituted by an aryl group.

As used herein, "arylheterocycloalkyl" refers to a heterocycloalkyl group substituted by an aryl group.

As used herein, "arylheteroaryl" refers to a heteroaryl group substituted by an aryl group.

As used herein, "biaryl" refers to an aryl group substituted by another aryl group.

As used herein, "heteroarylcycloalkyl" refers to a cycloalkyl group substituted by a heteroaryl group.

As used herein, "heteroarylheterocycloalkyl" refers to a heterocycloalkyl group substituted by a heteroaryl group.

As used herein, "heteroarylaryl" refers to an aryl group substituted by a heteroaryl group.

As used herein, "biheteroaryl" refers to a heteroaryl group substituted by another heteroaryl group.

As used herein, "halo" or "halogen" includes fluoro, chloro, bromo, and iodo.

As used herein, "hydroxyalkyl" refers to an alkyl group substituted with a hydroxyl group.

As used herein, "alkoxy" refers to an —O-alkyl group. Example alkoxy groups include methoxy, ethoxy, propoxy (e.g., n-propoxy and isopropoxy), t-butoxy, and the like.

As used herein, "alkoxyalkyl" refers to an alkyl group substituted by an alkoxy group.

As used herein, "alkoxyalkoxy" refers to an alkoxy group substituted by alkoxy.

As used herein, "haloalkoxy" refers to an —O-(haloalkyl) group.

As used herein, "arylalkyl" refers to alkyl substituted by aryl and "cycloalkylalkyl" refers to alkyl substituted by cycloalkyl. An example arylalkyl group is benzyl.

As used herein, "heteroarylalkyl" refers to alkyl substituted by heteroaryl and "heterocycloalkylalkyl" refers to alkyl substituted by heterocycloalkyl.

As used herein, "amino" refers to $NH_2$.

As used herein, "alkylamino" refers to an amino group substituted by an alkyl group.

As used herein, "dialkylamino" refers to an amino group substituted by two alkyl groups.

As used herein, "halosulfanyl" refers to a sulfur group having one or more halogen substituents. Example halosulfanyl groups include pentahalosulfanyl groups such as $SF_5$.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term "compound," as used herein, is meant to include all stereoisomers, geometric iosomers, tautomers, and isotopes of the structures depicted.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The compounds of the invention, and salts thereof, can also be prepared in combination with solvent or water molecules to form solvates and hydrates by routine methods.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Synthesis

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

The compounds of the invention can be prepared, for example, using the reaction pathways and techniques as described below.

A series of triazolotriazine derivatives of formulas 3 and 4 can be prepared by the method outlined in Scheme 1. Reaction of oxo-acetaldehyde 1 with 3,4-diaminotriazole 2 can afford the compounds 3 and 4.

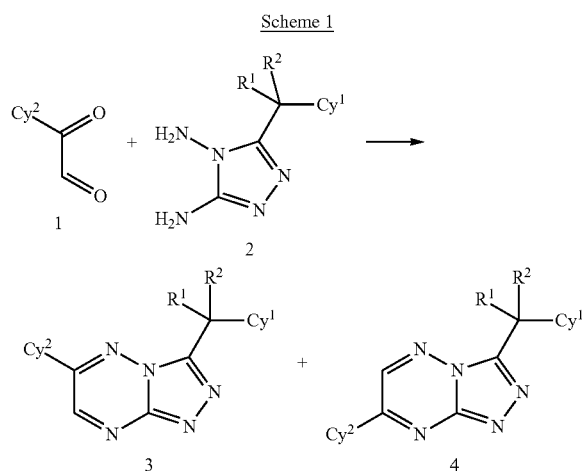

The 3,4-diaminotriazole 2 can be prepared by the method outlined in Scheme 2. For example, a mixture of a carboxylic acid 5 and 1,3-diaminoguanine 6 can be heated to form 2. Alternatively, the carboxylic acid 5 can be converted to the corresponding chloride 7 which reacts with hydrazide HBr salt 8 to give the acid hydrazide 9 which, in turn, can be transformed to the 3,4-diaminotriazole 2 by treatment with hydrazine.

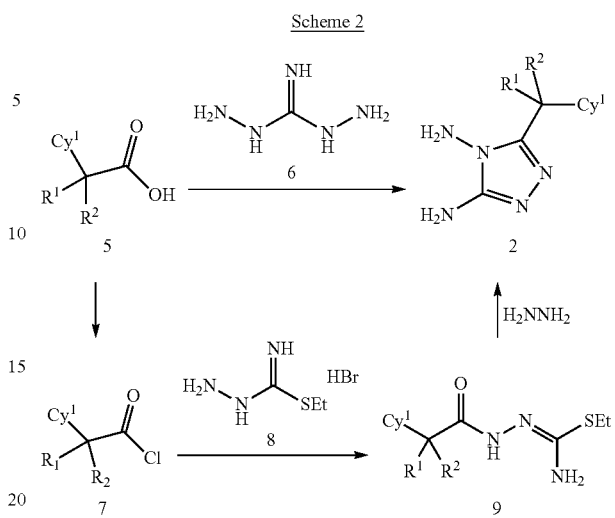

In a further alternative route, 3,4-diaminotriazole 2 can also be prepared by the method outlined in Scheme 3. Treatment of compound 10 with bromocyanide in the presence of a base such as potassium carbonate or sodium carbonate can give the 2-amino-oxadiazole 11 which, in turn, can be converted to the 3,4-diaminotriazole 2 by reaction with hydrazine.

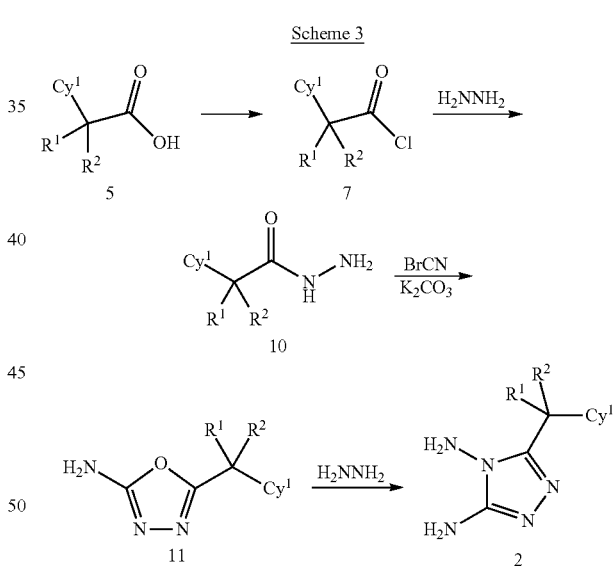

A series of triazolotriazine derivatives of formula 3 could be prepared according to the procedures outlined in Scheme 4. Semicarbazide 13 could be prepared by reaction of the semicarbazide hydrochloride with oxo-acetal 12 which could be obtained from oxo-acetaldehyde 1 by treatment with triethylformate. Intramolecular ring closure of 13 produced the triazinone 14 which could be transferred to the corresponding chloride 15 by reflux with POCl$_3$ in inert solvent such as chloroform, 1,2-dichloroethane or toluene in a presence of a catalytic amount of DMF. Replacement of the chlorine in 15 with hydrazine yield compound 16 which could be converted to the triazine 3 by reaction with the carboxylic acid 5 in presence of POCl$_3$. Alternatively, reaction of 16 with the chloride 7 could produce compound 17. Intramolecular ring closure of 17 in hot POCl₃ affords the triazolotriazine 3.

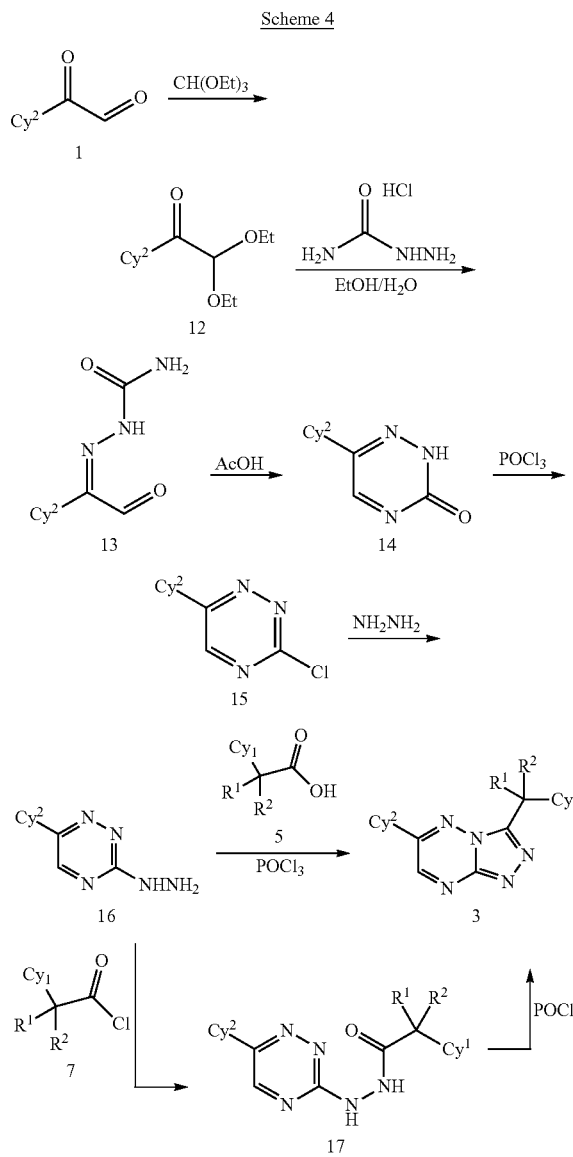

Alternatively, the triazinone 14 can be prepared according to the procedure outlined in Scheme 5. The oxo-acetaldehyde 1 can be transformed to the corresponding oxo-oxime 18. Reaction of 18 with semicarbazide can afford the compound 19. Hydrolysis of the oxime in 19 following intramolecular ring closure can afford the triazinone 14.

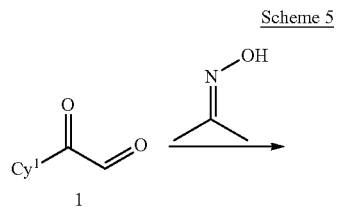

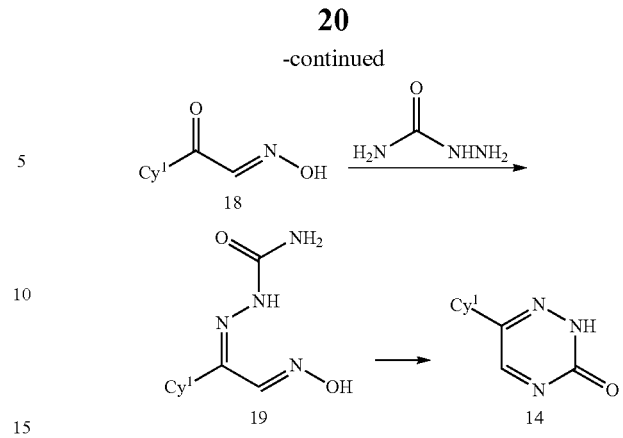

In a similar manner, the triazolotriazine 3 can be prepared by the methods outlined in Scheme 6. Amide 21, obtained by coupling of the acid 20 with N,O-dimethylhydroxylamine in presence of BOP or DCI, can be converted to the corresponding ketone 23 by reaction with lithium agent 22 which, in turn, can be produced by treatment of 1,3-dithiane and n-butyl lithium at low temperature. Reflux of the ketone 23 with thiosemicarbazide in an inert solvent such as ethanol or toluene and in the presence of an acid such as 4-toluenesulfonic acid can afford the compound 24. Alkylation of compound 24 with methyl iodide in the presence of a suitable base such as cesium carbonate, potassium carbonate, sodium carbonate, or sodium hydroxide can give triazine 25 which, in turn, can be transformed to the compound 16. The triazolotriazine 3 can be prepared from 16 as previously described.

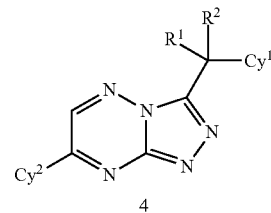

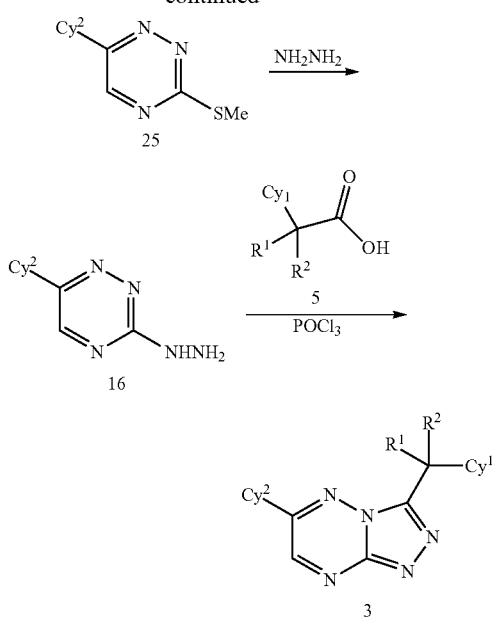

A series of triazolotriazine derivatives of formula 4 can further be prepared according to the procedures outlined in Scheme 7. Compound 26 can be conveniently obtained by reflux of oxo-acetaldehyde 1 with thiosemicarbazide hydrochloride in a solvent mixture of ethanol and water. Alkylation of compound 26 with methyl iodide in the presence of a base such as cesium carbonate, potassium carbonate, sodium carbonate, or sodium hydroxide can produce triazine 27 which can be transformed to compound 28 and the triazolotriazine 4 as previously described.

A series of triazolotriazine derivatives of formula 3 can be further prepared according to the procedures outlined in Scheme 8. Hydrazine derivative 31 can be obtained from the chloride 29 by treatment with ethyl hydrazinecarbimidothioate hydrobromide followed by replacement with hydrazine. Reaction of 31 with acid chloride 7 can produce the triazinone 32 which can be transformed to the corresponding chloride 33. Suzuki Coupling of 33 can afford the triazolotriazine derivative 34.

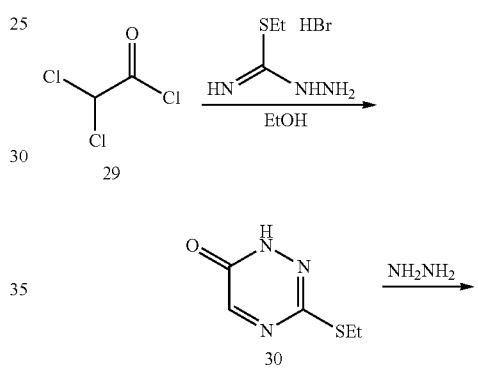

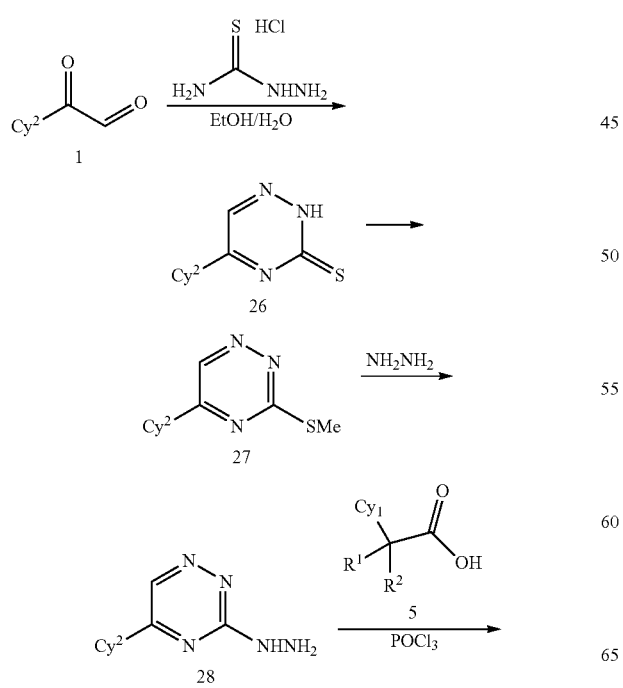

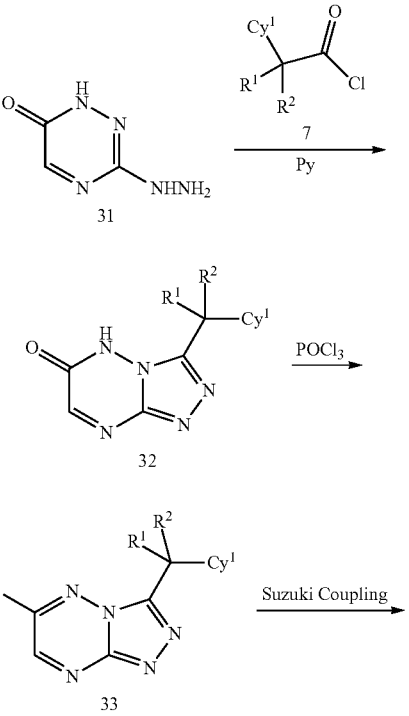

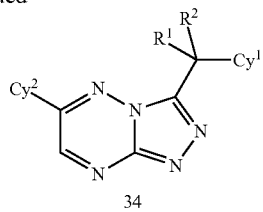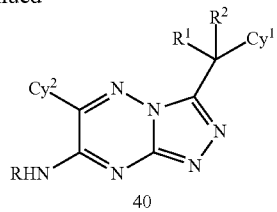

A series of triazolotriazine derivatives of formula 40 can be prepared according to the procedures outlined in Scheme 9. Treatment of the acid 20 with thiosemicarbazide in the presence of a base such as sodium carbonate, potassium carbonate, sodium hydroxide, or potassium hydroxide can give the compound 35 which, in turn, can convert to compound 36 by alkylation with methyl iodide. Triazinone 38 can be obtained from 36 by replacement with hydrazine followed by reaction with the chloride 7. Compound 38 can be transformed to the corresponding chloride 39 by treatment with $POCl_3$ or $SOCl_2$. Reaction of 39 with an appropriate amine can afford the triazolotriazine derivative 40.

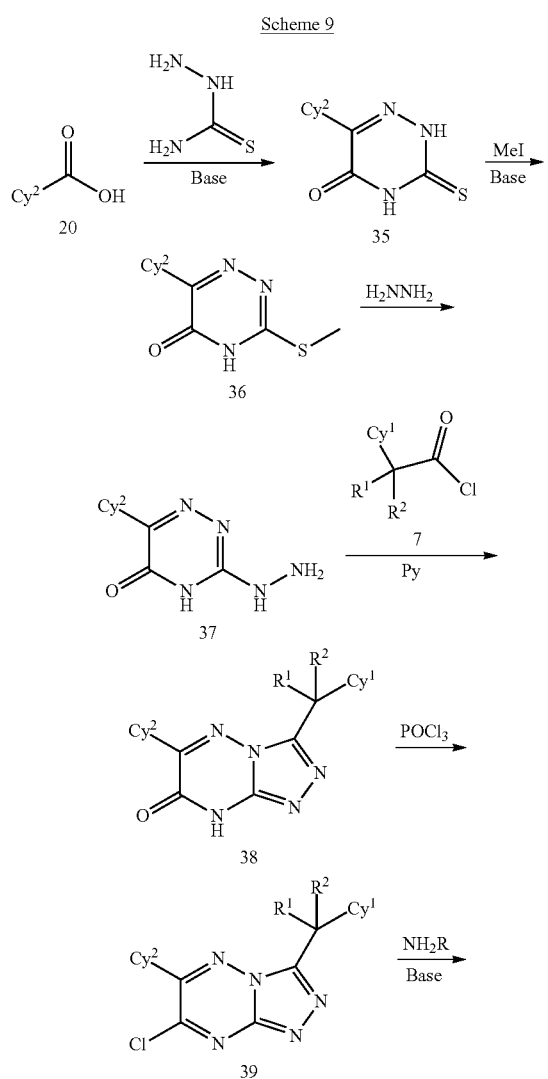

Methods of Use

Compounds of the invention can modulate activity of protein kinases. Example protein kinases modulated by the compounds of the invention include RTKs of the HER subfamily (e.g., EGFR, HER2, HER3 and HER4), of the insulin subfamily (e.g., INS-R, the IGF-1R and the IR-R), of the PDGF subfamily (e.g., the PDGF alpha and beta receptors, CSFIR, c-kit and FLK-II), of the FLK subfamily (e.g., Kinase insert Domain-Receptor fetal liver kinase-1 (KDR/FLK-1), the fetal liver kinase 4 (FLK-4) and the fms-like tyrosine kinases 1 and 3 (flt-1 and flt-3)), of the FGF receptor family (e.g., FGFR1, FGFR2, FGFR3 and FGFR4), of the Met subfamily (e.g., c-Met, Ron and Sea), and of the Src, Abl, and Jak (e.g., Jak1, Jak2, and Jak3) subfamilies. In some embodiments, the compounds of the invention modulate activity of c-Met.

The term "modulate" is meant to refer to an ability to increase or decrease activity of an enzyme or receptor. Modulation can occur in vitro or in vivo. Modulation can further occur in a cell. Accordingly, compounds of the invention can be used in methods of modulating a protein kinase, such as an RTK, by contacting the enzyme (or cell or sample containing the enzyme) with any one or more of the compounds or compositions described herein.

In some embodiments, compounds of the present invention can act as inhibitors of one or more protein kinases. In some further embodiments, compounds of the invention can be used in methods of inhibiting an RTK of the Met or FLK subfamilies. In yet further embodiments, the compounds of the invention can be used in methods of inhibiting c-Met, KDR, or flt-3 kinase. In yet further embodiments, the compounds of the invention can be used as inhibitors c-Met. In yet further embodiments, the compounds of the invention are selective inhibitors of c-Met.

Treatment of a cell (in vitro or in vivo) that expresses a protein kinase with a compound of the invention can result in inhibiting the ligand/kinase signaling pathway and inhibiting downstream events related to the signaling pathway such as cellular proliferation and increased cell motility. For example, the compounds of the invention can block and/or impair the biochemical and biological processes resulting from c-Met pathway activation, including, but not limited to, c-Met kinase activation (e.g. c-Met phosphorylation) and signaling (activation and recruitment of cellular substrates such as Gab1, Grb2, Shc and c-Cbl and subsequent activation of a number of signal transducers including PI-3 kinase, PLC-γ, STATs, ERK1/2 and FAK), cell proliferation and survival, cell motility, migration and invasion, metastasis, angiogenesis, and the like. Thus, the present invention further provides methods of inhibiting a ligand/kinase signaling pathway such as the HGF/c-Met kinase signaling pathway in a cell by contacting the cell with a compound of the invention. The present invention further provides methods of inhibiting proliferative activity of a cell or inhibiting cell motility by contacting the cell with a compound of the invention.

The present invention further provides methods of treating diseases associated with a dysregulated kinase signaling pathway, including abnormal activity and/or overexpression of the protein kinase, in an individual (e.g., patient) by administering to the individual in need of such treatment a therapeutically effective amount or dose of a compound of the present invention or a pharmaceutical composition thereof. In some embodiments, the dysregulated kinase is of the Met family (e.g., c-Met, Ron, or Sea). In some embodiments, the dysregulated kinase is overexpressed in the diseased tissue of the patient. In some embodiments, the dysregulated kinase is abnormally active in the diseased tissue of the patient. Dysregulation of c-Met and the HGF/c-Met signaling pathway is meant to include activation of the enzyme through various mechanisms including, but not limited to, HGF-dependent autocrine and paracrine activation, c-met gene overexpression and amplification, point mutations, deletions, truncations, rearrangement, as well as abnormal c-Met receptor processing and defective negative regulatory mechanisms.

In some embodiments, the compounds of the invention are useful in treating diseases such as cancer, atherosclerosis, lung fibrosis, renal fibrosis and regeneration, liver disease, allergic disorder, inflammatory disease, autoimmune disorder, cerebrovascular disease, cardiovascular disease, or condition associated with organ transplantation. In further embodiments, the compounds of the invention can be useful in methods of inhibiting tumor growth or metastasis of a tumor in a patient.

Example cancers treatable by the methods herein include bladder cancer, breast cancer, cervical cancer, cholangiocarcinoma cancer, colorectal cancer, esophageal cancer, gastric cancer, head and neck cancer, cancer of the kidney, liver cancer, lung cancer, nasopharygeal cancer, ovarian cancer, pancreatic cancer, prostate cancer, thyroid cancer, osteosarcoma, synovial sarcoma, rhabdomyosarcoma, MFH/fibrosarcoma, leiomyosarcoma, Kaposi's sarcoma, multiple myeloma, lymphoma, adult T cell leukemia, acute myelogenous leukemia, chronic myeloid leukemia, glioblastoma, astrocytoma, melanoma, mesothelioma, or Wilm's tumor, and the like.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" a compound of the invention with a protein kinase includes the administration of a compound of the present invention to an individual or patient, such as a human as well as, for example, introducing a compound of the invention into a sample containing a cellular or purified preparation of the protein kinase.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapy

One or more additional pharmaceutical agents or treatment methods such as, for example, chemotherapeutics, anti-cancer agents, cytotoxic agents, or anti-cancer therapies (e.g., radiation, hormone, etc.), can be used in combination with the compounds of the present invention for treatment of the diseases, disorders or conditions described herein. The agents or therapies can be administered together with the compounds of the invention (e.g., combined into a single dosage form), or the agents or therapies can be administered simultaneously or sequentially by separate routes of administration.

Suitable anti-cancer agents include kinase inhibiting agents including trastuzumab (Herceptin), imatinib (Gleevec), gefitinib (Iressa), erlotinib hydrochloride (Tarceva), cetuximab (Erbitux), bevacizumab (Avastin), sorafenib (Nexavar), sunitinib (Sutent), and RTK inhibitors described in, for example, WO 2005/004808, WO 2005/004607, WO 2005/005378, WO 2004/076412, WO 2005/121125, WO 2005/039586, WO 2005/028475, WO 2005/040345, WO 2005/039586, WO 2003/097641, WO 2003/087026, WO 2005/040154, WO 2005/030140, WO 2006/014325, WO 2005/070891, WO 2005/073224, WO 2005/113494, and US Pat. App. Pub. Nos. 2005/0085473, 2006/0046991, and 2005/0075340.

Suitable chemotherapeutic or other anti-cancer agents further include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Suitable chemotherapeutic or other anti-cancer agents further include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol™), mithramycin, deoxyco-formycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor;

procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-β, etc.). Further antibody therapeutics include antibodies to tyrosine kinases and/or their ligands such as anti-HGF antibodies and/or anti-c-Met antibodies. The term "antibody" is meant to include whole antibodies (e.g., monoclonal, polyclonal, chimeric, humanized, human, etc.) as well as antigen-binding fragments thereof.

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Other anti-cancer agents include anti-cancer vaccines such as dendritic cells, synthetic peptides, DNA vaccines and recombinant viruses.

Methods for the safe and effective administration of most of the above agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions which is a combination of a compound of the invention and a pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as anti-viral agents, vaccines, antibodies, immune enhancers, immune suppressants, anti-inflammatory agents and the like.

Labeled Compounds and Assay Methods

Another aspect of the present invention relates to fluorescent dye, spin label, heavy metal or radio-labeled compounds of the invention that would be useful not only in imaging but also in assays, both in vitro and in vivo, for localizing and quantitating the protein kinase target in tissue samples, including human, and for identifying kinase ligands by inhibition binding of a labeled compound. Accordingly, the present invention includes kinase enzyme assays that contain such labeled compounds.

The present invention further includes isotopically-labeled compounds of the compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and a $^{131}I$. The radionuclide that is incorporated in the instant radio-labeled compounds will depend on the specific application of that radio-labeled compound. For example, for in vitro IDO enzyme labeling and competition assays, compounds that incorporate $^{3}H$, $^{14}C$, $^{82}Br$, $^{125}I$, $^{131}I$, $^{35}S$ or will generally be most useful. For radio imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the enzyme. Accordingly, the ability of a test compound to compete with the radio-labeled compound for binding to the enzyme directly correlates to its binding affinity.

Kits

The present invention also includes pharmaceutical kits useful, for example, in the treatment or prevention of diseases, such as cancer and other diseases referred to herein, which include one or more containers containing a pharmaceutical composition comprising a therapeutically effective amount of a compound of the invention, or pharmaceutically acceptable salt thereof. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. The compounds of the Examples were found to be inhibitors of c-Met according to one or more of the assays provided herein.

EXAMPLES

Preparations for compounds of the invention are provided below. In some instances, the crude product was a mixture of regioisomers. Typically, these isomers were separated on a preparative scale by HPLC or flash chromatography (silica gel) as indicated in the Examples. Typical preparative RP-HPLC column conditions were as follows:

pH=2 purifications: Waters Sunfire™ C$_{18}$ 5 µm, 19×100 mm column, eluting with mobile phase A: 0.1% TFA (trifluoroacetic acid) in water and mobile phase B: 0.1% TFA in acetonitrile; the flow rate was 30 ml/m, the separating gradient was optimized for each compound using the Compound Specific Method Optimization protocol as described in literature ["Preparative LC-MS Purification: Improved Compound Specific Method Optimization", K. Blom, B. Glass, R. Sparks, A. Combs, *J. Combi. Chem.*, 6, 874-883 (2004)].

pH=10 purifications: Waters XBridge C$_{18}$ 5 µm, 19×100 mm column, eluting with mobile phase A: 0.15% NH$_4$OH in water and mobile phase B: 0.15% NH$_4$OH in acetonitrile; the flow rate was 30 ml/m, the separating gradient was optimized for each compound using the Compound Specific Method Optimization protocol as described in literature ["Preparative LC-MS Purification: Improved Compound Specific Method Optimization", K. Blom, B. Glass, R. Sparks, A. Combs, *J. Combi. Chem.*, 6, 874-883 (2004)].

The separated isomers were then typically subjected to analytical LC/MS for purity check under the following conditions: Instrument; Agilent 1100 series, LC/MSD, Column. Waters Sunfire™ C$_{18}$ 5 µm, 2.1×5.0 mm, Buffers: mobile phase A: 0.025% TFA in water and mobile phase B: 0.025% TFA in acetonitrile; gradient 2% to 80% of B in 3 min with flow rate 1.5 mL/min. Retention time (Rt) data in the Examples refer to these analytical LC/MS conditions unless otherwise specified.

Example 1

3-[1-(4-Methoxyphenyl)cyclopropyl]-6-phenyl[1,2,4]triazolo[4,3-b][1,2,4]triazine and 3-[1-(4-Methoxyphenyl)cyclopropyl]-7-phenyl[1,2,4]triazolo[4,3-b][1,2,4]triazine

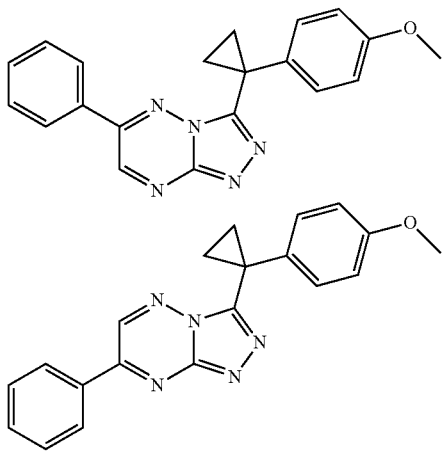

Step 1. Methyl 1-(4-methoxyphenyl)cyclopropanecarboxylate

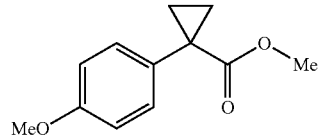

1-(4-Methoxyphenyl)cyclopropanecarboxylic acid (0.970 g, 5.05 mmol) in dichloromethane (DCM; 5 mL) was mixed with oxalyl chloride (1.28 mL, 15.1 mmol) followed by addition of a drop of N,N-dimethylformamide (DMF; 20 µL). The mixture was stirred at room temperature (RT) for 2 h. The solvent was evaporated. The residue was co-evaporated with toluene (2×), and dissolved in DCM (10 mL). The solution was cooled at −10° C., and then methanol (3 mL) was carefully added to the solution. The resulting mixture was allowed to warm to RT. The volatiles were evaporated under reduced pressure to afford the desired product (1.03 g, 99%).

Step 2. 1-(4-Methoxyphenyl)cyclopropanecarbohydrazide

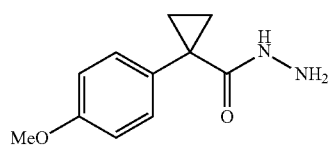

A mixture of methyl 1-(4-methoxyphenyl)cyclopropanecarboxylate (0.90 g, 4.4 mmol) and hydrazine (0.65 mL, 21 mmol) was heated at 120° C. for 2 h. After cooling, the excess hydrazine was removed under reduced pressure. The residue was treated with water, filtered and washed with water to give the desired product (750 mg, 83%). Analytical LCMS: (M+H)+=207.1.

Step 3. 5-[1-(4-Methoxyphenyl)cyclopropyl]-1,3,4-oxadiazol-2-amine

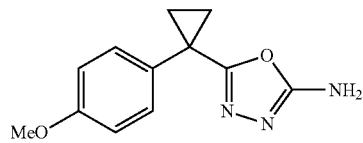

Cyanogen bromide (0.424 g, 4.0 mmol) was added to an ice-cooled slurry of 1-(4-methoxyphenyl)cyclopropanecarbohydrazide (0.750 g, 3.64 mmol) and potassium bicarbonate (0.50 g, 5.0 mmol) in methanol (8 mL). The mixture was stirred at 0° C. for 1 h. the ice bath was allowed to warm slowly and stirred at RT for overnight. The reaction mixture was diluted with water (10 mL), stirred for 1 h. The precipitate was collected by filtration and washed with water, and dried on high vacuum to afford the desired product (600 mg, 71.3%). Analytical LCMS: (M+H)+=232.1.

Step 4. 5-[1-(4-Methoxyphenyl)cyclopropyl]-4H-1,2,4-triazole-3,4-diamine

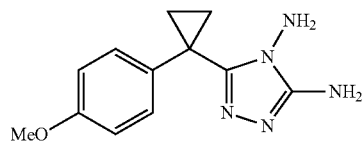

A mixture of 5-[1-(4-methoxyphenyl)cyclopropyl]-1,3,4-oxadiazol-2-amine (0.60 g, 2.6 mmol), and hydrazine (0.64 mL, 20 mmol) in water (2.0 mL) was heated at 190° C. for 3 h. After cooling to RT, the mixture was further cooled with ice-water. The crystalline solid formed was collected by filtration, washed with water, and dried under high vacuum to yield the desired product (300 mg, 47.1%). Analytical LCMS: (M+H)+=246.1.

Step 5. 3-[1-(4-methoxyphenyl)cyclopropyl]-6-phenyl[1,2,4]triazolo[4,3-b][1,2,4]triazine and 3-[1-(4-methoxyphenyl)cyclopropyl]-7-phenyl[1,2,4]triazolo[4,3-b][1,2,4]triazine A mixture of 5-[1-(4-methoxyphenyl)cyclopropyl]-4H-1,2,4-triazole-3,4-diamine (70.2 mg, 0.286 mmol) and oxo(phenyl)acetaldehyde hydrate (0.0435 g, 0.286 mmol) in acetic acid (1.2 mL) was stirred at RT overnight. The mixture was diluted with methanol (3.0 mL) and subject to preparative RP-HPLC to afford the two regioisomers.

Retention times for analytical LC/MS were as follows: Isomer-I: Rt=1.763 min; Isomer-II: Rt=1.784 min. Analytical LCMS: (M+H)+=344.1.

Example 2

4-[1-(6-Phenyl[1,2,4]triazolo[4,3-b][1,2,4]triazin-3-yl)cyclopropyl]phenol and 4-[1-(7-Phenyl[1,2,4]triazolo[4,3-b][1,2,4]triazin-3-yl)cyclopropyl]phenol

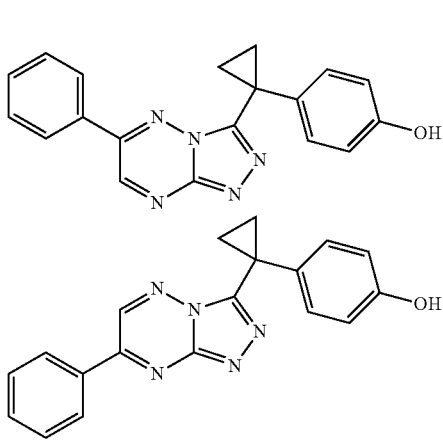

To a mixture of 3-[1-(4-methoxyphenyl)cyclopropyl]-6-phenyl[1,2,4]triazolo[4,3-b][1,2,4]triazine (17.0 mg, 0.0495 mmol) and 3-[1-(4-methoxyphenyl)cyclopropyl]-7-phenyl[1,2,4]triazolo[4,3-b][1,2,4]triazine (17.0 mg, 0.0495 mmol) in DCM (3.0 mL) was added 1.00 M of boron tribromide in DCM (0.5 mL). The mixture was stirred at RT for 3 h. The solvent was evaporated. The residue was diluted with methanol (5 mL). The resulting mixture was subject to preparative RP-HPLC to give the two regioisomers. Analytical LCMS: (M+H)+=330.1. Isomer-I: Rt=1.451 min; Isomer-II: Rt=1.450 min.

Example 3

6-(4-Fluorophenyl)-3-[1-(4-methoxyphenyl)cyclopropyl][1,2,4]triazolo[4,3-b][1,2,4]triazine and 7-(4-Fluorophenyl)-3-[1-(4-methoxyphenyl)cyclopropyl][1,2,4]triazolo[4,3-b][1,2,4]triazine

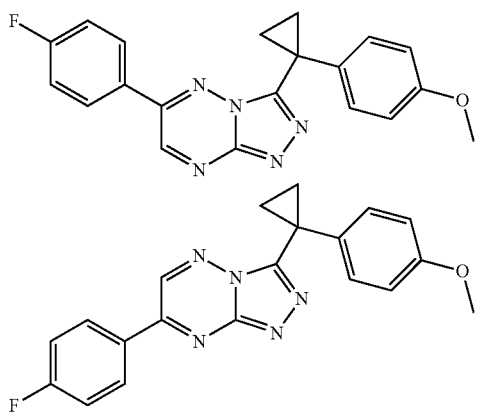

The above two compounds were prepared using procedures analogous to those for Example 1. Analytical LCMS: (M+H)+=362.1. Isomer-I: Rt=1.832 min; Isomer-II: Rt=1.801 min.

Example 4

3-[1-(4-Methoxyphenyl)cyclopropyl]-6-(4-morpholin-4-ylphenyl)[1,2,4]triazolo[4,3-b][1,2,4]triazine and 3-[1-(4-Methoxyphenyl)cyclopropyl]-7-(4-morpholin-4-ylphenyl)[1,2,4]triazolo[4,3-b][1,2,4]triazine

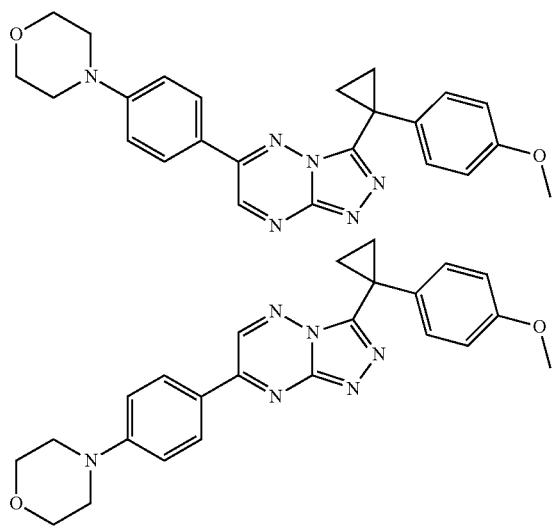

The above two compounds were prepared using procedures analogous to those for Example 1. Analytical LCMS: (M+H)+=429.1. Isomer-I: Rt=1.744 min; Isomer-II: Rt=1.753 min.

Example 5

6-(4-Chlorophenyl)-3-[1-(4-methoxyphenyl)cyclopropyl][1,2,4]triazolo[4,3-b][1,2,4]triazine and 7-(4-Chlorophenyl)-3-[1-(4-methoxyphenyl)cyclopropyl][1,2,4]triazolo[4,3-b][1,2,4]triazine

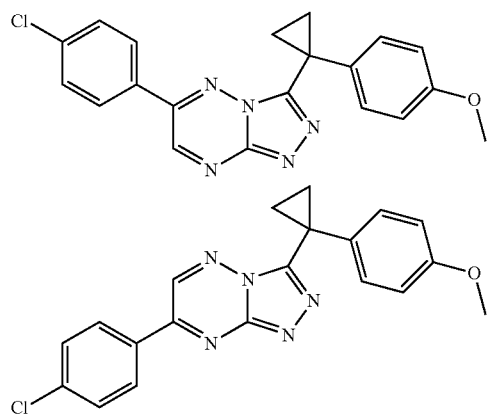

The above two compounds were prepared using procedures analogous to those for Example 1. Analytical LCMS: (M+H)+=378.0/380.1. Isomer-I: Rt=2.044 min; Isomer-II: Rt=2.012 min.

Example 6

4-{3-[1-(4-Methoxyphenyl)cyclopropyl][1,2,4]triazolo[4,3-b][1,2,4]triazin-6-yl}phenol and 4-{3-[1-(4-Methoxyphenyl)cyclopropyl][1,2,4]triazolo[4,3-b][1,2,4]triazin-7-yl}phenol

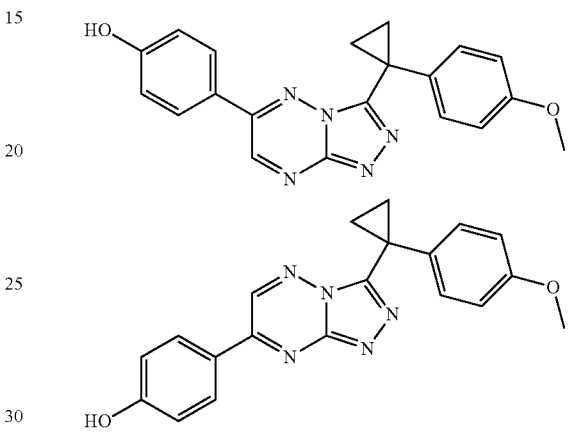

The above two compounds were prepared using procedures analogous to those for Example 1. Analytical LCMS: (M+H)+=360.1. Isomer-I: Rt=1.550 min; Isomer-II: Rt=1.602 min.

Example 7

4-3-[1-(4-Methoxyphenyl)cyclopropyl][1,2,4]triazolo[4,3-b][1,2,4]triazin-6-ylbenzonitrile and 4-{3-[1-(4-Methoxyphenyl)cyclopropyl][1,2,4]triazolo[4,3-b][1,2,4]triazin-7-yl}benzonitrile

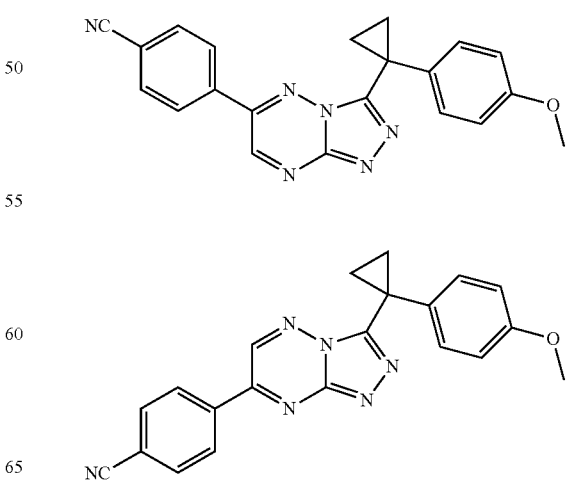

The above two compounds were prepared using procedures analogous to those for Example 1. Analytical LCMS: (M+H)$^+$=369.1. Isomer-I: Rt=1.780 min; Isomer-II: Rt=1.772 min.

Example 8

N-(4-{3-[1-(4-Methoxyphenyl)cyclopropyl][1,2,4]triazolo[4,3-b][1,2,4]triazin-6-yl}phenyl)acetamide and N-(4-{3-[1-(4-Methoxyphenyl)cyclopropyl][1,2,4]triazolo[4,3-b][1,2,4]triazin-7-yl}phenyl)acetamide

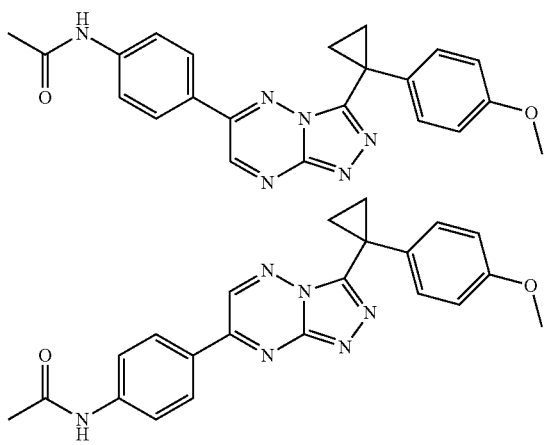

The above two compounds were prepared using procedures analogous to those for Example 1. Analytical LCMS: (M+H)$^+$=401.1. Isomer-I: Rt=1.505 min; Isomer-II: Rt=1.565 min.

Example 9

6-(4-Methoxyphenyl)-3-[1-(4-methoxyphenyl)cyclopropyl][1,2,4]triazolo[4,3-b][1,2,4]triazine and 7-(4-Methoxyphenyl)-3-[1-(4-methoxyphenyl)cyclopropyl][1,2,4]triazolo[4,3-b][1,2,4]triazine

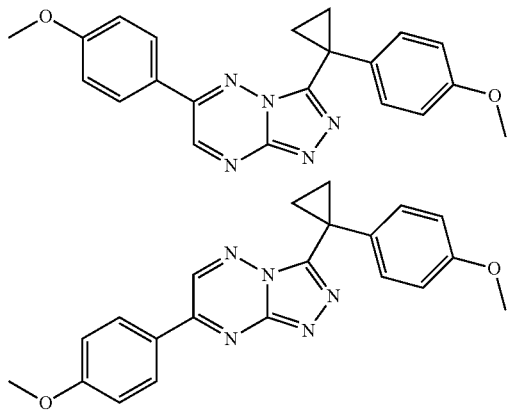

Example 10

6-(2,4-Difluorophenyl)-3-[1-(4-methoxyphenyl)cyclopropyl][1,2,4]triazolo[4,3-b][1,2,4]triazine and 7-(2,4-Difluorophenyl)-3-[1-(4-methoxyphenyl)cyclopropyl][1,2,4]triazolo[4,3-b][1,2,4]triazine

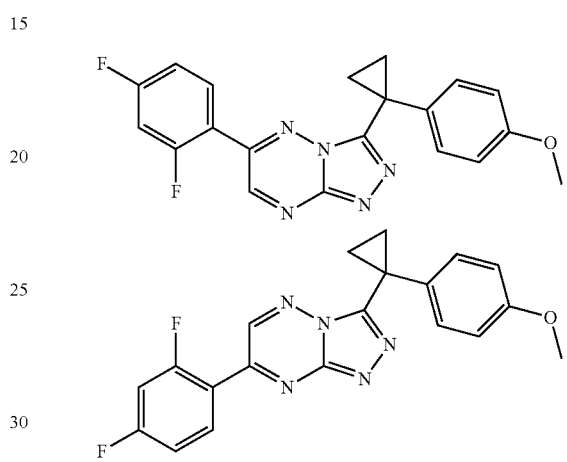

These two compounds were prepared using procedures analogous to those for Example 1. Analytical LCMS: (M+H)$^+$=380.1. Isomer-I: Rt=1.971 min; Isomer-II: Rt=1.989 min.

Example 11

6-(3,4-Dichlorophenyl)-3-[1-(4-methoxyphenyl)cyclopropyl][1,2,4]triazolo[4,3-b][1,2,4]triazine and 7-(3,4-Dichlorophenyl)-3-[1-(4-methoxyphenyl)cyclopropyl][1,2,4]triazolo[4,3-b][1,2,4]triazine

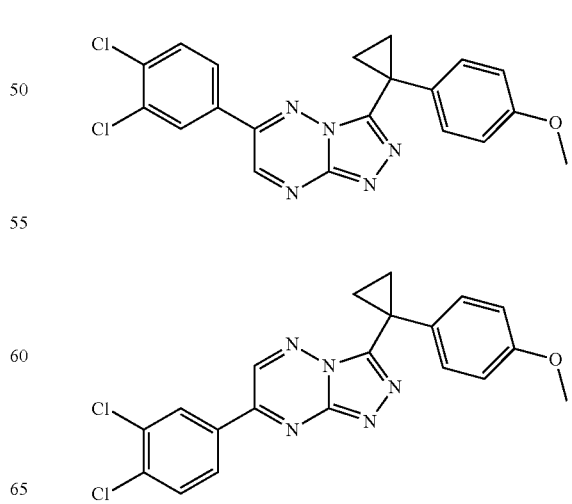

The above two compounds were prepared using procedures analogous to those for Example 1. Analytical LCMS: (M+H)⁺=412.0/414.0. Isomer-I: Rt=2.261 min; Isomer-II: Rt=2.230 min.

Example 12

6-(3,4-Difluorophenyl)-3-[1-(4-methoxyphenyl)cyclopropyl][1,2,4]triazolo[4,3-b][1,2,4]triazine and 7-(3,4-Difluorophenyl)-3-[1-(4-methoxyphenyl)cyclopropyl][1,2,4]triazolo[4,3-b][1,2,4]triazine

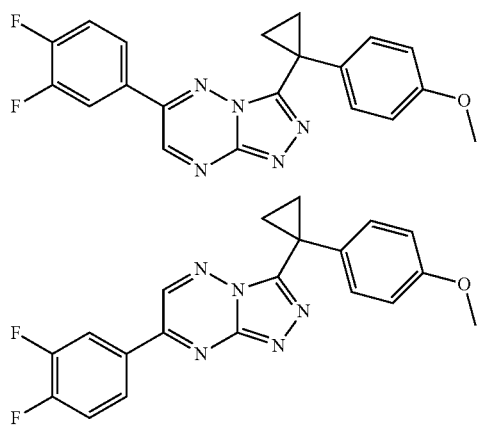

The above two compounds were prepared using procedures analogous to those for Example 1. Analytical LCMS: (M+H)⁺=380.1. Isomer-I: Rt=1.988 min; Isomer-II: Rt=2.013 min.

Example 13

6-(3-Methoxyphenyl)-3-[1-(4-methoxyphenyl)cyclopropyl][1,2,4]triazolo[4,3-b][1,2,4]triazine and 7-(3-Methoxyphenyl)-3-[1-(4-methoxyphenyl)cyclopropyl][1,2,4]triazolo[4,3-b][1,2,4]triazine

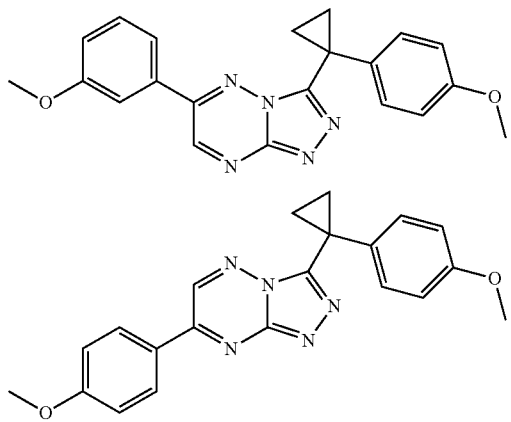

The above two compounds were prepared using procedures analogous to those for Example 1. Analytical LCMS: (M+H)⁺=374.1. Isomer-I: Rt=1.936 min; isomer-II: Rt=1.941 min.

Example 14

6-(3-Bromophenyl)-3-[1-(4-methoxyphenyl)cyclopropyl][1,2,4]triazolo[4,3-b][1,2,4]triazine and 7-(3-Bromophenyl)-3-[1-(4-methoxyphenyl)cyclopropyl][1,2,4]triazolo[4,3-b][1,2,4]triazine

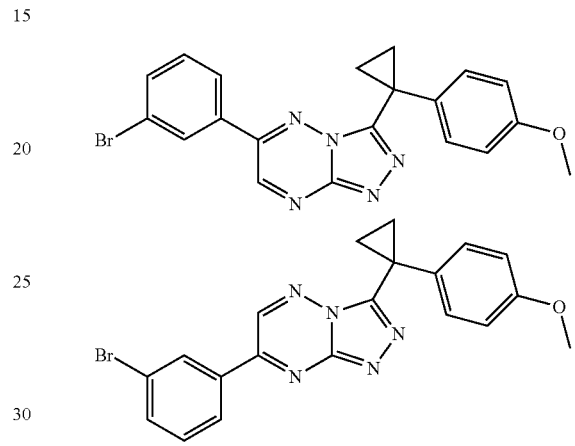

The above two compounds were prepared using procedures analogous to those for Example 1. Analytical LCMS: (M+H)⁺=422.0/424.0. Isomer-I: Rt=2.054 min; isomer-II: Rt=2.036 min.

Example 15

6-(5-Bromo-2-thienyl)-3-[1-(4-methoxyphenyl)cyclopropyl][1,2,4]triazolo[4,3-b][1,2,4]triazine and 7-(5-Bromo-2-thienyl)-3-[1-(4-methoxyphenyl)cyclopropyl][1,2,4]triazolo[4,3-b][1,2,4]triazine

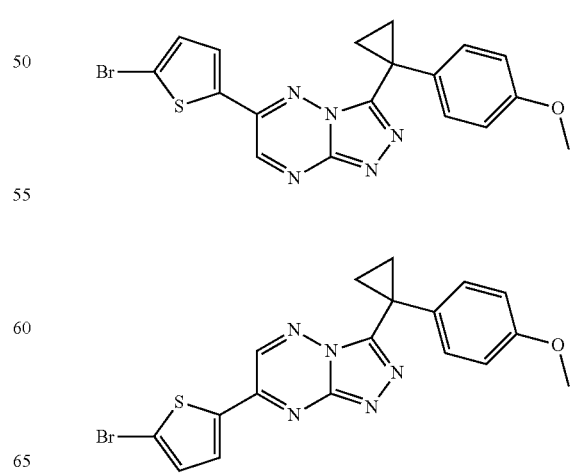

The above two compounds were prepared using procedures analogous to those for Example 1. Analytical LCMS: (M+H)⁺=428.0/430.0.

Example 16

3-[1-(4-Methoxyphenyl)cyclopropyl]-6-(4-nitrophenyl)[1,2,4]triazolo[4,3-b][1,2,4]triazine and 3-[1-(4-Methoxyphenyl)cyclopropyl]-7-(4-nitrophenyl)[1,2,4]triazolo[4,3-b][1,2,4]triazine

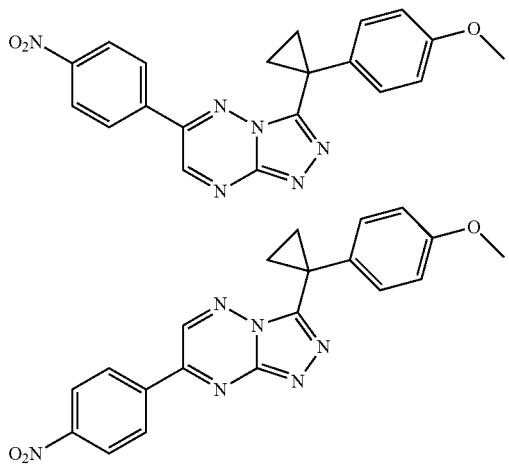

Step 1. Ethyl hydrazinecarbimidothioate hydrobromide

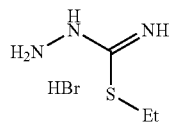

A mixture of thiosemicarbazide (18.2 g, 0.200 mol) and ethyl bromide (32.0 g, 0.294 mol) in ethanol (250 mL) was heated under reflux overnight. The solvent was evaporated under reduced pressure. The residue was triturated with ether, filtered, and dried under high vacuum to afford the desired product (38 g, 95%). Analytical LCMS: (M+H)⁺=120.1.

Step 2. Ethyl N'-[1-(4-methoxyphenyl)cyclopropyl]carbonylhydrazonothio-carbamate hydrobromide

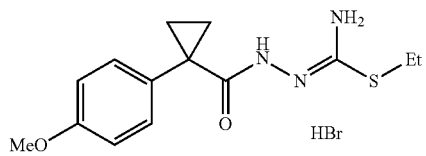

Oxalyl chloride (10.0 mL, 0.118 mol) was added to a solution of 1-(4-methoxyphenyl)cyclopropanecarboxylic acid (8.10 g, 0.0421 mol) in methylene chloride (50.0 mL), followed by the addition of DMF (0.1 mL). The mixture was stirred at RT for 2 h. The volatiles were evaporated. The residue was co-evaporated with toluene. The residue was dissolved in tetrahydrofuran (160.0 mL), followed by the addition of ethyl hydrazinecarbimidothioate hydrobromide (8.43 g, 0.0421 mol). The mixture was stirred at RT overnight. The solvent was evaporated. The residue was triturated with ether, filtered, and dried under high vacuum to give the desired product (15 g, 95.1%). Analytical LCMS: (M+H)⁺=294.1.

Step 3. 5-[1-(4-Methoxyphenyl)cyclopropyl]-4H-1,2,4-triazole-3,4-diamine

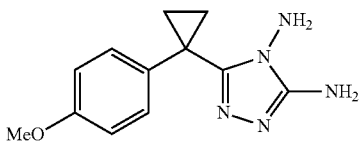

A mixture of ethyl N'-[1-(4-methoxyphenyl)-cyclopropyl]-carbonylhydrazonothio-carbamate (3.51 g, 0.012 mol) and hydrazine (3.0 mL, 0.0956 mol) in methanol (20.0 mL) and water (20.0 mL) was heated under reflux overnight. The mixture was diluted with methanol and water. The resulting solution was purified by RP-HPLC (pH=10.0 conditions) to give the desired product (1.23 g, 41.9%). Analytical LCMS: (M+H)⁺=246.1.

Step 4. 3-[1-(4-Methoxyphenyl)cyclopropyl]-6-(4-nitrophenyl) [1,2,4]triazolo[4,3-b][1,2,4]triazine and 3-[1-(4-Methoxyphenyl)cyclopropyl]-7-(4-nitrophenyl) [1,2,4]triazolo[4,3-b][1,2,4]triazine A mixture of 5-[1-(4-methoxyphenyl)cyclopropyl]-4H-1,2,4-triazole-3,4-diamine (307 mg, 1.25 mmol) and (4-nitrophenyl)(oxo)acetaldehyde hydrate (246 mg, 1.25 mmol) in acetic acid (10.0 mL) was stirred at RT overnight. The mixture was concentrated under reduced pressure. The residue was flash chromatographed on a silica gel column with 5% methanol-DCM to afford two regioisomers.

Isomer-I (210 mg, 43%), TLC $R_f$=0.63 (plate: silica gel 60 F254, EMD Chemicals Inc.; solvent: 10% methanol in DCM); Analytical LCMS: (M+H)⁺=389.1. Rt=1.962 min. ¹H-NMR (500 MHz, CDCl₃): 8.88 (s, 1H), 8.40-8.48 (m, 2H), 8.36-8.39 (m, 2H), 7.39-7.43 (m, 2H), 6.79-6.83 (m, 2H), 3.76 (s, 3H), 1.70-1.73 (m, 2H), 1.49-1.52 (m, 2H).

Isomer-II (200 mg, 41%), TLC $R_f$=0.47 (plate: silica gel 60 F254, EMD Chemicals Inc.; solvent: 10% methanol in DCM); Analytical LCMS: (M+H)⁺=389.1. Rt=1.973 min. ¹H-NMR (500 MHz, CDCl₃): 8.96 (s, 1H), 8.41-8.45 (m, 2H), 8.06-8.10 (m, 2H), 7.45-7.49 (m, 2H), 6.84-6.88 (m, 2H), 3.78 (s, 3H), 1.75-1.79 (m, 2H), 1.52-1.55 (m, 2H).

Example 17

6-(4-Bromophenyl)-3-[1-(4-methoxyphenyl)cyclopropyl][1,2,4]triazolo[4,3-b][1,2,4]triazine and 7-(4-Bromophenyl)-3-[1-(4-methoxyphenyl)cyclopropyl][1,2,4]triazolo[4,3-b][1,2,4]triazine

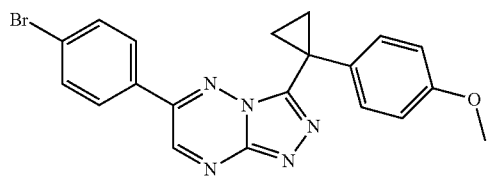

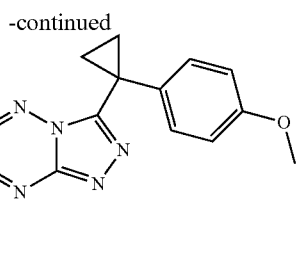

The above two compounds were prepared using procedures analogous to those for Example 16. Analytical LCMS: (M+H)⁺=422.0/424.0. Isomer-I: Rt=2.138 min; Isomer-II: Rt=2.108 min.

Example 18

4-{3-[1-(4-Methoxyphenyl)cyclopropyl][1,2,4]triazolo[4,3-b][1,2,4]triazin-6-yl}aniline and 4-{3-[1-(4-Methoxyphenyl)cyclopropyl][1,2,4]triazolo[4,3-b][1,2,4]triazin-7-yl}aniline

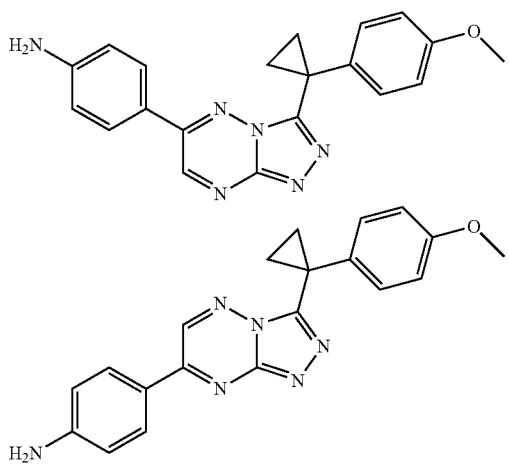

Platinum (5.0 mg) on carbon (5%) was added to a 140 mg mixture of the two regioisomers: 3-[1-(4-methoxyphenyl)cyclopropyl]-6-(4-nitrophenyl)-[1,2,4]triazolo[4,3-b][1,2,4]triazine and 3-[1-(4-methoxyphenyl)cyclopropyl]-7-(4-nitrophenyl)-[1,2,4]-triazolo[4,3-b][1,2,4]triazine in methanol (5.0 mL, 0.12 mol) under nitrogen. The mixture was stirred at RT under an atmosphere of hydrogen for 3 h, and was filtered. The filtrate was concentrated and subject to preparative RP-HPLC to afford two regioisomers. Analytical LCMS: (M+H)⁺=359.1. Isomer-I: Rt=1.565 min; Isomer-II: Rt=1.619 min.

Example 19

3-[1-(4-Methoxyphenyl)cyclopropyl]-6-[3-(1-methyl-1H-pyrazol-4-yl)phenyl][1,2,4]triazolo[4,3-b][1,2,4]triazine and 3-[1-(4-Methoxyphenyl)cyclopropyl]-7-[3-(1-methyl-1H-pyrazol-4-yl)phenyl][1,2,4]triazolo[4,3-b][1,2,4]triazine

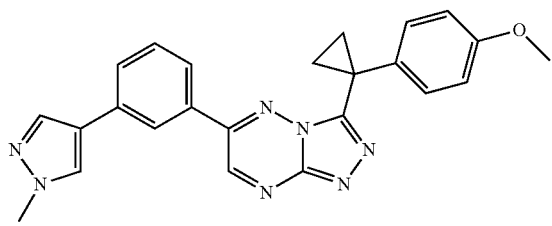

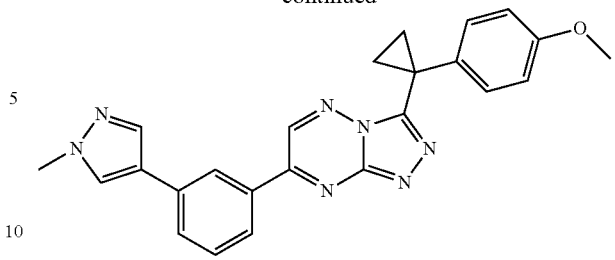

Sodium carbonate (19.1 mg, 0.180 mmol) in water (0.10 mL) was added to a mixture of 1-methyl-4-(4,4,5,5-tetramethyl-1,3,2-dioxaborolan-2-yl)-1H-pyrazole (18.7 mg, 0.0900 mmol), tetrakis(triphenylphosphine)palladium(0) (2.0 mg) and a 25.4 mg of a mixture of two regioisomers: 6-(3-bromophenyl)-3-[1-(4-methoxyphenyl)cyclopropyl][1,2,4]triazolo[4,3-b][1,2,4]triazine and 7-(3-bromophenyl)-3-[1-(4-methoxyphenyl)cyclopropyl][1,2,4]-triazolo[4,3-b][1,2,4]triazine in ethanol (300 μL) and toluene (300 μL). The resulting mixture was heated at 150° C. for 1 h. After cooling, the mixture was concentrated and diluted with methanol. The resulting solution was filtered, and the filtrate was subject to preparative RP-HPLC to give the two regioisomers. Analytical LCMS: (M+H)⁺=424.1. Isomer-I: Rt=1.732 min; Isomer-II: Rt=1.764 min.

Example 20

3-[1-(4-Methoxyphenyl)cyclopropyl]-6-[3-(1H-pyrazol-4-yl)phenyl][1,2,4]triazolo[4,3-b][1,2,4]triazine and 3-[1-(4-Methoxyphenyl)cyclopropyl]-7-[3-(1H-pyrazol-4-yl)phenyl][1,2,4]triazolo[4,3-b][1,2,4]triazine

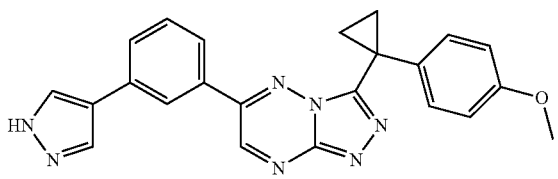

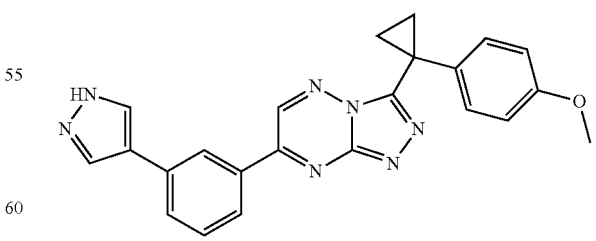

The above two regioisomers were prepared using procedures analogous to those for Example 19. Analytical LCMS: (M+H)⁺=410.1. Isomer-I: Rt=1.606 min; Isomer-II: Rt=1.655 min.

Example 21 tert-Butyl (3'-3-[1-(4-methoxyphenyl)cyclopropyl]
[1,2,4]triazolo[4,3-b][1,2,4]triazin-6-ylbiphenyl-4-
yl)carbamate and tert-Butyl (3'-{3-[1-(4-methox-
yphenyl)cyclopropyl][1,2,4]triazolo[4,3-b][1,2,4]
triazin-7-yl}biphenyl-4-yl)carbamate

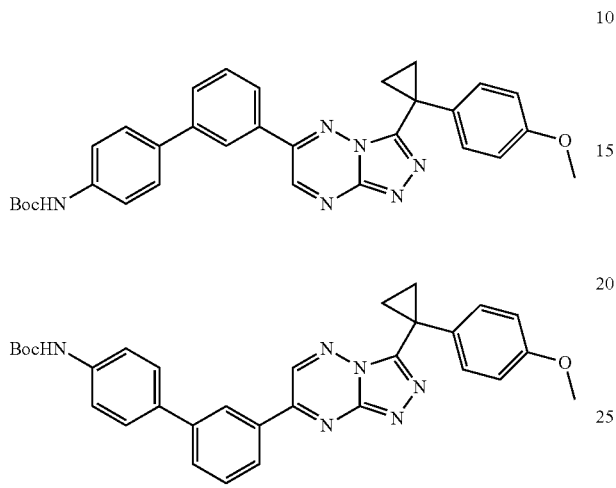

The above two regioisomers were prepared using procedures analogous to those for Example 19. Analytical LCMS: (M+H)$^+$=535.1. Isomer-I: Rt=2.421 min; Isomer-II: Rt=2.430 min.

Example 22

3-[1-(4-Methoxyphenyl)cyclopropyl]-(6 or 7)-[4-
(1H-pyrazol-4-yl)phenyl][1,2,4]-triazolo[4,3-b][1,2,
4]triazine

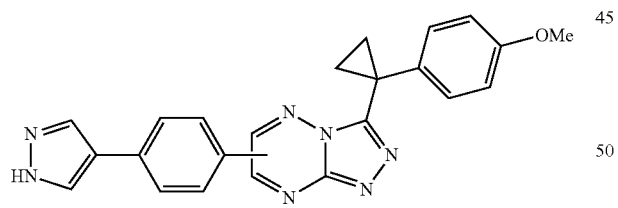

Sodium carbonate (25.4 mg, 0.240 mmol) in water (0.10 mL) was added to a mixture of Isomer-II from Example 17 (16.9 mg, 0.0400 mmol), 4-(4,4,5,5-tetramethyl-1,3,2-dioxaborolan-2-yl)-1H-pyrazole (11.6 mg, 0.060 mmol) and tetrakis(triphenylphosphine)-palladium(0) (2.7 mg, 0.0023 mmol) in ethanol (400 μL) and toluene (400 μL). The resulting mixture was heated at 150° C. for 2 h. The mixture was concentrated and the residue diluted with methanol. The resulting solution was filtered and the filtrate was purified by preparative RP-HPLC to give the desired product. Analytical LCMS: (M+H)$^+$=410.1. Rt=1.622 min.

Example 23

3-[1-(4-Methoxyphenyl)cyclopropyl]-(6 or 7)-[4-(1-
methyl-1H-pyrazol-4-yl)phenyl][1,2,4]triazolo[4,3-
b][1,2,4]triazine

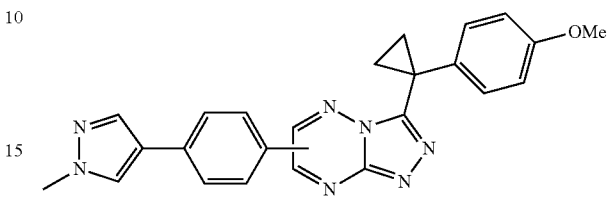

The above compound was prepared using procedures analogous to those for Example 22. Analytical LCMS: (M+H)$^+$=424.2. Rt=1.766 min.

Example 24

3-[1-(4-Bromophenyl)cyclopropyl]-6-phenyl[1,2,4]
triazolo[4,3-b][1,2,4]triazine

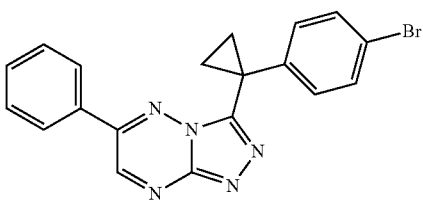

Step 1.
[(Aminocarbonyl)hydrazono](phenyl)acetaldehyde

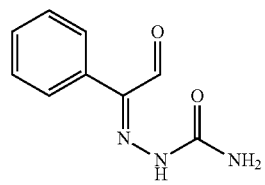

A mixture of 2,2-diethoxy-1-phenylethanone (6.25 g, 0.0300 mol) and semicarbazide hydrochloride (3.34 g, 0.0300 mol) in ethanol-water (1:1 v/v, 50 mL) was heated at 120° C. for 3 h. The mixture was concentrated under reduced pressure. The residue was treated with methanol, filtered, and washed with methanol to give the desired product (3.40 g, 59.3%). Analytical LCMS: (M+H)$^+$=192.1. $^1$H-NMR (400 MHz, DMSO-D$_6$): δ 11.03 (s, 1H), 7.97-8.01 (m, 2H), 7.61-7.67 (m, 1H), 7.50-7.56 (m, 2H), 7.34 (b, 1H), 6.54 (b, 2H).

Step 2. 6-Phenyl-1,2,4-triazin-3(2H)-one

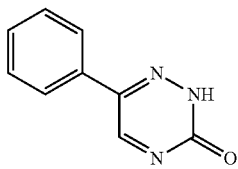

[(Aminocarbonyl)hydrazono](phenyl)acetaldehyde (3.00 g, 0.0157 mol) in acetic acid (15.0 mL) was heated at 130° C. for 6 h. After cooling, the solvent was removed under reduced pressure. The residue was triturated with ether, filtered, washed with ether, and dried under high vacuum to give the desired product (2.45 g, 90.1%). Analytical LCMS: (M+H)$^+$= 174.0.

Step 3. 3-Chloro-6-phenyl-1,2,4-triazine

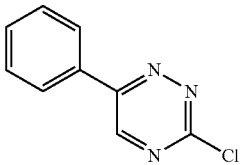

A mixture of 6-phenyl-1,2,4-triazin-3(2H)-one (2.45 g, 0.0141 mol) and DMF (0.5 mL) in phosphoryl chloride (20.0 mL, 0.214 mol) and chloroform (20.0 mL) was heated under reflux overnight. After cooling, the volatiles were removed under reduced pressure. The residue was dissolved in DCM (60 mL) and was poured into ice with stirring. The mixture was neutralized with NaOH (1N), and filtered through a pad of celite to remove a small amount of insoluble residue. The organic layer was separated. The aqueous layer was extracted with DCM (3×20 mL). The combined organic layers were dried over Na$_2$SO$_4$, filtered, and concentrated. The residue was flash chromatographed on a silica gel column to give the desired product (2.20 g, 81.1%). Analytical LCMS: (M+H)$^+$= 192.1/194.1.

Step 4. 3-Hydrazino-6-phenyl-1,2,4-triazine

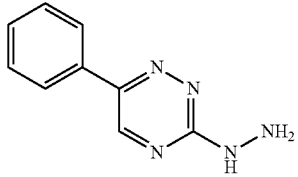

Hydrazine hydrate (1.50 mL, 0.0308 mol) was added to suspension of 3-chloro-6-phenyl-1,2,4-triazine (2.20 g, 0.0115 mol) in pyridine (12.0 mL) at 0° C. and stirred at 0° C. until a precipitate formed. The mixture was then heated at 65° C. for 30 min. The solvent was evaporated under reduced pressure. The residue was triturated with water, filtered, and washed with water. The crystalline formed was collected and dried under high vacuum to give the desired product (2.0 g, 93%). Analytical LCMS: (M+H)$^+$=188.1.

Step 5. 3-[1-(4-Bromophenyl)cyclopropyl]-6-phenyl[1,2,4]triazolo[4,3-b][1,2,4]triazine A mixture of 3-hydrazino-6-phenyl-1,2,4-triazine (18.7 mg, 0.10 mmol) and 1-(4-bromophenyl)cyclopropanecarboxylic acid (24.1 mg, 0.10 mmol) in phosphoryl chloride (0.50 mL) was heated at 120° C. for 3 h. Excess phosphoryl chloride was removed under reduced pressure. The residue was treated with water and methanol. The resulting solution was subject to preparative RP-HPLC (pH=2) to give the desired product as a TFA salt. Analytical LCMS: (M+H)$^+$=392.0/394.0

Example 25

3-[1-(3-Bromophenyl)cyclopropyl]-6-phenyl[1,2,4]triazolo[4,3-b][1,2,4]triazine

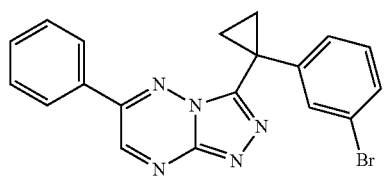

This compound was prepared as a TFA salt using procedures analogous to those for Example 24. Analytical LCMS: (M+H)$^+$=392.0/394.0.

Example 26

3-[1-(4-Methoxyphenyl)cyclopropyl]-6-phenyl[1,2,4]triazolo[4,3-b][1,2,4]triazine

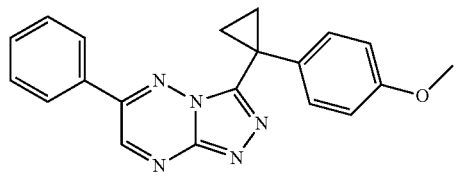

This compound was prepared as a TFA salt using procedures analogous to those for Example 24. Analytical LCMS: (M+H)$^+$=344.1.

Example 27

6-[1-(6-Phenyl[1,2,4]triazolo[4,3-b][1,2,4]triazin-3-yl)cyclopropyl]quinoline

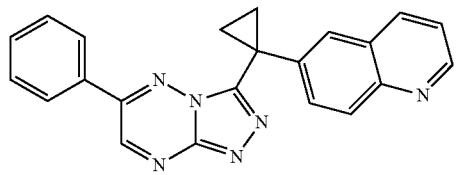

This compound was prepared using procedures analogous to those for Example 24. Analytical LCMS: (M+H)$^+$=365.1.

Example 28

3-[1-(4-Chlorophenyl)cyclopropyl]-6-(4-fluorophenyl)[1,2,4]triazolo[4,3-b][1,2,4]triazine

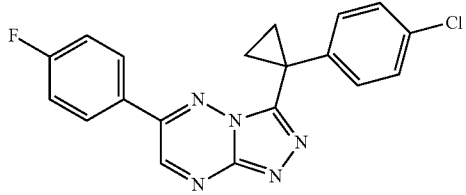

Step 1. 2,2-Diethoxy-1-(4-fluorophenyl)ethanone

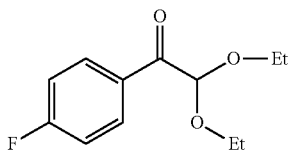

A mixture of 1-(4-fluorophenyl)-2,2-dihydroxyethanone (4.0 g, 0.024 mol), ethyl orthoformate (7.3 g, 0.049 mol), p-toluenesulfonic acid monohydrate (0.2 g, 0.001 mol) in methylene chloride (50 mL) was heated at reflux for 40 min. After cooling, the mixture was concentrated. The residue was flash chromatographed on a silica gel column eluting with DCM to give 5.15 g of the desired product. $^1$H-NMR (300 MHz, CDCl$_3$): 8.18-8.25 (m, 2H), 7.08-7.16 (m, 2H), 5.18 (s, 1H), 3.58-3.82 (m, 4H), 1.25 (t, J=7.0 Hz, 6H).

Step 2. 6-(4-Fluorophenyl)-1,2,4-triazin-3(2H)-one

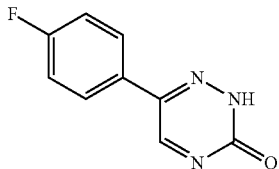

A mixture of 2,2-diethoxy-1-(4-fluorophenyl)ethanone (5.15 g, 0.0228 mol), semicarbazide hydrochloride (2.6 g, 0.024 mol) in ethanol (50 mL) was stirred at RT overnight, and then heated at 80° C. for 5 h. The mixture was concentrated. The residue was dissolved in acetic acid (50 mL), and heated at 130° C. for 6 h. After cooling, the mixture was concentrated, and the residue was triturated with ethyl ether, filtered, and washed with ether and then hexane. The crystalline solid was collected and dried under high vacuum to the desired product (4.18 g, 96.1%). Analytical LCMS: (M+H)$^+$= 192.1.

Step 3. 6-(4-Fluorophenyl)-3-hydrazino-1,2,4-triazine

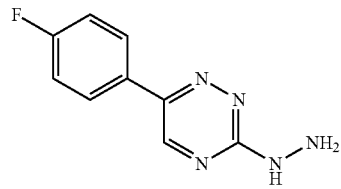

Hydrazine hydrate (0.28 mL, 0.0057 mol) was added to a suspension of 3-chloro-6-(4-fluorophenyl)-1,2,4-triazine (400 mg, 0.002 mol) in pyridine (4 mL) at 0° C. and stirred at 0° C. until a precipitate formed. The mixture was then heated at 65° C. for 30 min. The solvent was evaporated under reduced pressure. The residue was triturated with water, filtered, and washed with water. The crystalline solid was collected and dried under high vacuum to give the desired product (360 mg, 91.9%). Analytical LCMS: (M+H)$^+$=206.1.

Step 4. 3-[1-(4-Chlorophenyl)cyclopropyl]-6-(4-fluorophenyl)[1,2,4]triazolo[4,3-b][1,2,4]triazine A mixture of 6-(4-fluorophenyl)-3-hydrazino-1,2,4-triazine (20.5 mg, 0.10 mmol) and 1-(4-chlorophenyl)cyclopropanecarboxylic acid (19.6 mg, 0.10 mmol) in phosphoryl chloride (0.50 mL) was heated at 120° C. for 3 h. Excess phosphoryl chloride was removed under reduced pressure. The residue was treated with water and methanol. The resulting solution was subject to RP-HPLC (pH=2) to give the desired product as a TFA salt. Analytical LCMS: (M+H)$^+$= 366.0.

Example 29

3-[1-(2,4-Dichlorophenyl)cyclopropyl]-6-(4-fluorophenyl)[1,2,4]triazolo[4,3-b][1,2,4]triazine

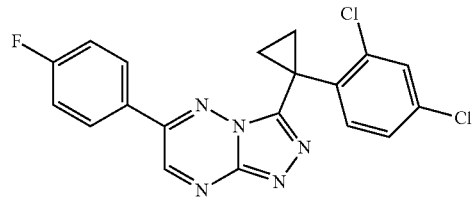

This compound was prepared as a TFA salt using procedures analogous to those for Example 28. Analytical LCMS: (M+H)$^+$=400.0.

Example 30

3-[1-(3-Bromophenyl)cyclopropyl]-6-(4-fluorophenyl)[1,2,4]triazolo[4,3-b][1,2,4]triazine

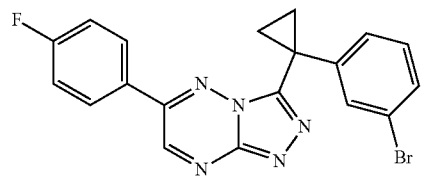

This compound was prepared as a TFA salt using procedures analogous to those for Example 28. Analytical LCMS: (M+H)⁺=409.9/411.9.

Example 31

3-[1-(4-Bromophenyl)cyclopropyl]-6-(4-fluorophenyl)[1,2,4]triazolo[4,3-b][1,2,4]triazine

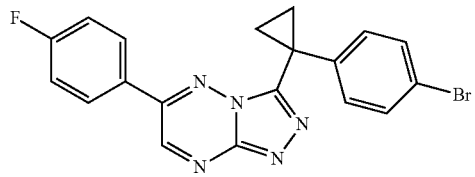

This compound was prepared as a TFA salt using procedures analogous to those for Example 28. Analytical LCMS: (M+H)⁺=409.9/411.9.

Example 32

3-[1-(2-Chlorophenyl)cyclopropyl]-6-(4-fluorophenyl)[1,2,4]triazolo[4,3-b][1,2,4]triazine

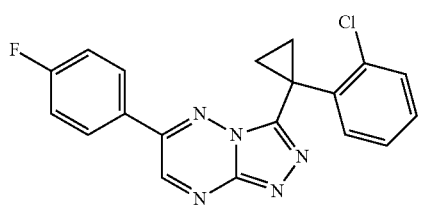

This compound was prepared as a TFA salt using procedures analogous to those for Example 28. Analytical LCMS: (M+H)⁺=366.1.

Example 33

6-(4-Fluorophenyl)-3-[1-(2-methoxyphenyl)cyclopropyl][1,2,4]triazolo[4,3-b][1,2,4]triazine

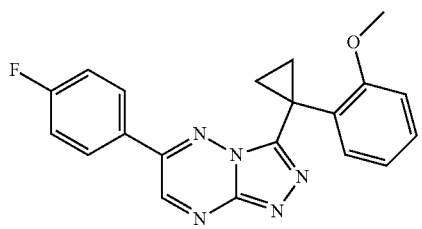

This compound was prepared as a TFA salt using procedures analogous to those for Example 28. Analytical LCMS: (M+H)⁺=362.0.

Example 34

6-(4-Fluorophenyl)-3-[1-(3-fluorophenyl)cyclopropyl][1,2,4]triazolo[4,3-b][1,2,4]triazine

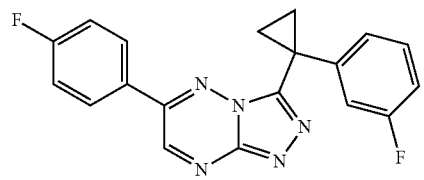

This compound was prepared as a TFA salt using procedures analogous to those for Example 28. Analytical LCMS: (M+H)⁺=350.0.

Example 35

6-(4-Fluorophenyl)-3-{1-[3-(trifluoromethyl)phenyl]cyclopropyl}[1,2,4]triazolo[4,3-b][1,2,4]triazine

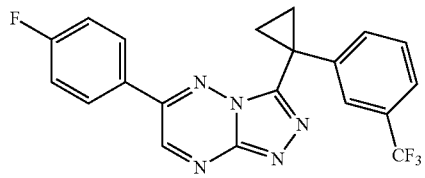

This compound was prepared as a TFA salt using procedures analogous to those for Example 28. Analytical LCMS: (M+H)⁺=400.0.

Example 36

3-[1-(2-Chloro-6-fluorophenyl)cyclopropyl]-6-(4-fluorophenyl)[1,2,4]triazolo[4,3-b][1,2,4]triazine

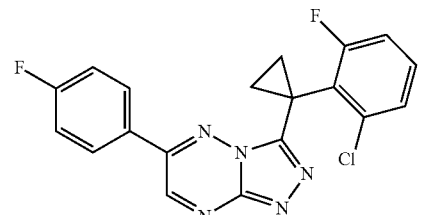

This compound was prepared as a TFA salt using procedures analogous to those for Example 28. Analytical LCMS: (M+H)⁺=384.0.

Example 37

3-[1-(1,3-Benzodioxol-5-yl)cyclopropyl]-6-(4-fluorophenyl)[1,2,4]triazolo[4,3-b][1,2,4]triazine

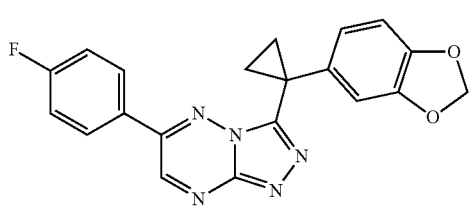

This compound was prepared as a TFA salt using procedures analogous to those for Example 28. Analytical LCMS: (M+H)$^+$=376.1.

Example 38

4-{1-[6-(4-Fluorophenyl)[1,2,4]triazolo[4,3-b][1,2,4]triazin-3-yl]cyclopropyl}quinoline

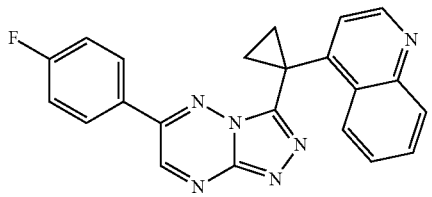

This compound was prepared as a TFA salt using procedures analogous to those for Example 28. Analytical LCMS: (M+H)$^+$=383.0.

Example 39

6-{1-[6-(4-Fluorophenyl) [1,2,4]triazolo[4,3-b][1,2,4]triazin-3-yl]cyclopropyl}quinoline

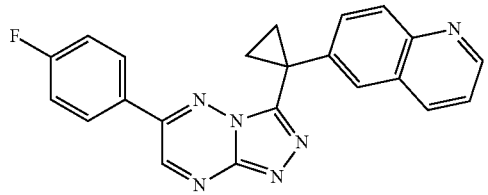

This compound was prepared as a TFA salt using procedures analogous to those for Example 28. Analytical LCMS: (M+H)$^+$=383.0.

Example 40

6-{1-[6-(3-Bromophenyl) [1,2,4]triazolo[4,3-b][1,2,4]triazin-3-yl]cyclopropyl}quinoline

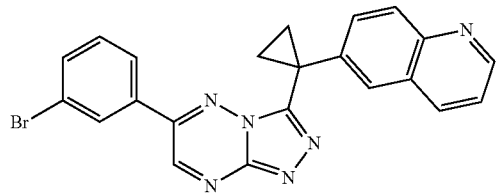

This compound was prepared as a TFA salt using procedures analogous to those for Example 28. Analytical LCMS: (M+H)$^+$=443.0/445.0.

Example 41

6-{1-[6-(4-Bromophenyl)[1,2,4]triazolo[4,3-b][1,2,4]triazin-3-yl]cyclopropyl}quinoline

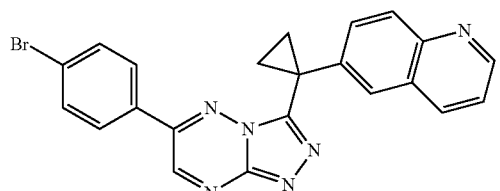

This compound was prepared as a TFA salt using procedures analogous to those for Example 28. Analytical LCMS: (M+H)$^+$=443.0/445.0.

Example 42

3-[3-(1-Quinolin-6-ylcyclopropyl)[1,2,4]triazolo[4,3-b][1,2,4]triazin-6-yl]benzonitrile

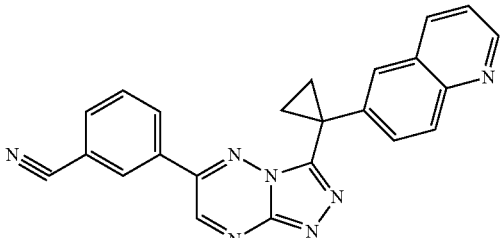

A mixture of 6-{1-[6-(3-bromophenyl)[1,2,4]triazolo[4,3-b][1,2,4]triazin-3-yl]cyclopropyl}quinoline (Example 40, 10 mg, 0.02 mmol), zinc cyanide (3.24 mg, 0.0271 mmol), bis(tri-t-butylphosphine)palladium (7 mg, 0.01 mmol), and zinc powder (1.77 mg, 0.0271 mmol) in DMF (0.6 mL) was heated at 170° C. for 20 min under microwave. After cooling to ambient temperature, the mixture was filtered. The filtrate was diluted with methanol and subject to preparative RP-HPLC (pH=10) to afford the desired product. Analytical LCMS: (M+H)$^+$=390.2.

Example 43

4-[3-(1-Quinolin-6-ylcyclopropyl)[1,2,4]triazolo[4,3-b][1,2,4]triazin-6-yl]benzonitrile

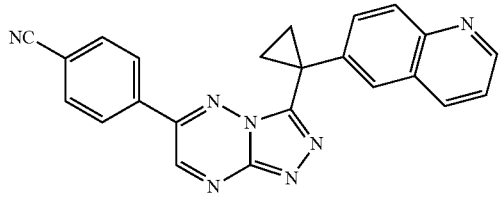

This compound was prepared using procedures analogous to those for Example 42. Analytical LCMS: (M+H)⁺=390.2.

Example 44

3-[1-(4-Methoxyphenyl)cyclopropyl]-6-phenyl[1,2,4]triazolo[4,3-b][1,2,4]triazin-7-amine

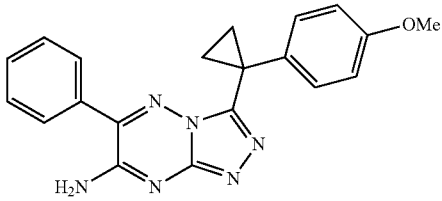

Step 1. 3-(Methylthio)-6-phenyl-1,2,4-triazin-5(4H)-one

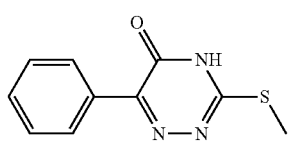

A mixture of thiosemicarbazide (1.8 g, 0.020 mol) and benzoylformic acid (3.0 g, 0.020 mol) in water (50 mL) was heated under reflux for 15 min. Then potassium hydroxide (1.5 g, 0.027 mol) in methanol (50 mL) was added at 80° C. The reaction mixture was stirred and heated at 80° C. for 2 days. After cooling to 35° C., methyl iodide (1.4 mL, 0.022 mol) was added. The reaction mixture was stirred at 40° C. for 30 min. The mixture was concentrated. The precipitate formed was collected by filtration, washed with water, and dried under vacuum to afford the desired product (4.3 g, 97.7%). Analytical LCMS: (M+H)⁺=220.1.

Step 2. 3-Hydrazino-6-phenyl-1,2,4-triazin-5(4H)-one

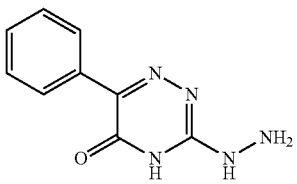

To 3-(methylthio)-6-phenyl-1,2,4-triazin-5(4H)-one (4.3 g) in isopropyl alcohol (40 mL) was added hydrazine (6.41 g, 0.200 mol). The reaction mixture was refluxed for 10 h. After cooling, the crystalline solid formed was filtered and washed with isopropyl alcohol. The crystalline solid was collected and dried in vacuo to afford the desired product. Analytical LCMS: (M+H)⁺=204.1.

Step 3. 3-[1-(4-Methoxyphenyl)cyclopropyl]-6-phenyl[1,2,4]triazolo[4,3-b][1,2,4]triazin-7(8H)-one

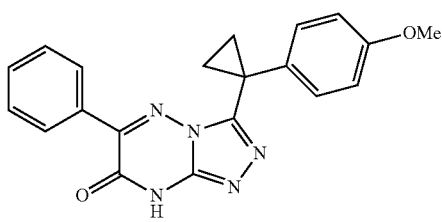

To a solution of 3-hydrazino-6-phenyl-1,2,4-triazin-5(4H)-one (40.0 mg, 0.197 mmol) in pyridine (0.5 mL) was added 1-(4-methoxyphenyl)cyclopropanecarbonyl chloride (0.062 g, 0.30 mmol) and the resulting mixture was irradiated under microwave at 150° C. for 15 min. The reaction mixture was diluted with methanol and purified by RP-HPLC to afford the desired product (50 mg, 70%). Analytical LCMS: (M+H)⁺=360.2.

Step 4. 3-[1-(4-Methoxyphenyl)cyclopropyl]-6-phenyl[1,2,4]triazolo[4,3-b][1,2,4]triazin-7-amine A mixture of 3-[1-(4-methoxyphenyl)cyclopropyl]-6-phenyl[1,2,4]triazolo[4,3-b][1,2,4]triazin-7(8H)-one (43.1 mg, 0.120 mmol) and phosphoryl chloride (1.0 mL, 0.011 mol) was stirred and heated at 120° C. for 4 h. Excess phosphoryl chloride was removed under reduced pressure. The residue was dissolved in acetonitrile (0.5 mL). To the solution was added ammonium hydroxide (20.0 μL). The mixture was stirred at RT for 30 min, and was diluted with methanol. The resulting solution was subject to preparative RP-HPLC (pH=10) to give the desired product. Analytical LCMS: (M+H)⁺=359.1.

Example 45

6-(4-Fluorophenyl)-3-[1-(4-methoxyphenyl)cyclopropyl][1,2,4]triazolo[4,3-b][1,2,4]triazin-7-amine

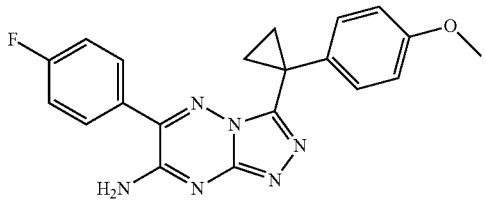

Step 1. Methyl (4-fluorophenyl)(oxo)acetate

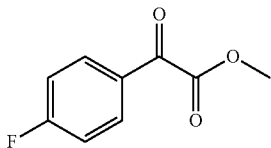

A mixture of 4-fluorobenzoyl chloride (3 g, 0.02 mol) and copper cyanide (2.3 g, 0.026 mol) in acetonitrile (2 mL) and in toluene (4 mL) was heated under reflux for 3 h. After cooling, the mixture was filtered. The filtrate was diluted with ethyl acetate, washed with water, brine, and dried over $MgSO_4$. The mixture was filtered and concentrated. The residue was dissolved in ether-methanol. The solution was saturated with hydrogen chloride gas, and stirred at RT for 2 h. The precipitate formed was collected by filtration, washed with ether, and dried under high vacuum to give the desired product (2.1 g, 61%). $^1$H-NMR (300 MHz, $CDCl_3$): 8.06-8.13 (m, 2H), 7.15-7.23 (m, 2H), 3.98 (s, 3H).

Step 2. 6-(4-Fluorophenyl)-3-(methylthio)-1,2,4-triazin-5(4H)-one

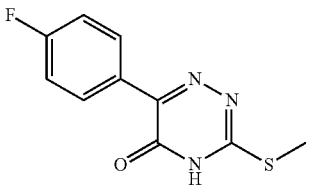

A mixture of methyl (4-fluorophenyl)(oxo)acetate (1.1 g, 0.0059 mol), thiosemicarbazide (0.54 g, 0.0059 mol) in water (10 mL) was heated at reflux for 15 min. Then methanol (10 mL) was added, followed by potassium hydroxide (0.43 g, 0.0077 mol). The mixture was stirred at 90° C. overnight. After cooling, methyl iodide (4 mL, 0.06 mol) was added. The mixture was stirred at RT for 30 min. The precipitate formed was collected by filtration, washed with ether, and dried under high vacuum to give the desired product (1.2 g, 77%). Analytical LCMS: $(M+H)^+$=238.1.

Step 3. 6-(4-Fluorophenyl)-3-[1-(4-methoxyphenyl)cyclopropyl][1,2,4]triazolo[4,3-b][1,2,4]triazin-7-amine This compound was prepared using procedures analogous to Steps 2-4 of Example 44. Analytical LCMS: $(M+H)^+$=377.1.

Example 46

6-{3-[1-(4-Methoxyphenyl)cyclopropyl][1,2,4]triazolo[4,3-b][1,2,4]triazin-6-yl}-1,3-benzothiazol-2-amine

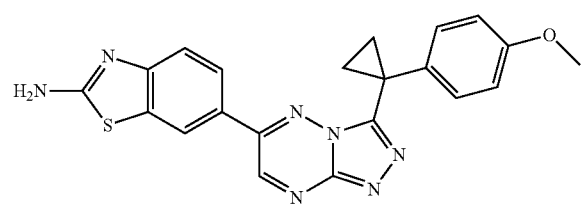

4-{3-[1-(4-methoxyphenyl)cyclopropyl][1,2,4]triazolo[4,3-b][1,2,4]triazin-6-yl}aniline (preparation in Example 18, isomer-I, 35.8 mg, 0.10 mmol) was dissolved in acetic acid (1.00 mL). To the solution was added potassium thiocyanate (38.8 mg, 0.400 mmol) and bromine (5.14 μL, 0.10 mmol) in acetic acid (0.10 mL). The mixture was stirred at RT overnight, and was diluted with DMSO (1.0 mL). The resulting solution was purified by RP-HPLC (pH=2) to give the desired product as a TFA salt. Analytical LCMS: $(M+H)^+$=416.0.

Example 47

1-(4-{3-[1-(4-Methoxyphenyl)cyclopropyl][1,2,4]triazolo[4,3-b][1,2,4]triazin-6-yl}phenyl)pyrrolidin-2-one

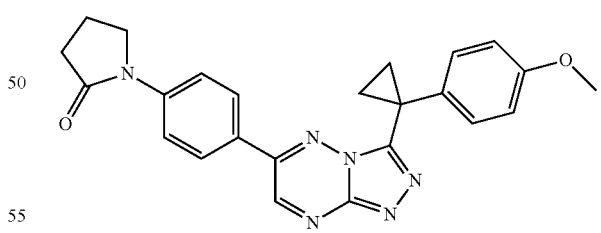

A mixture of 6-(4-bromophenyl)-3-[1-(4-methoxyphenyl)cyclopropyl][1,2,4]-triazolo[4,3-b][1,2,4]triazine (Example 17, isomer-I, 25.3 mg, 0.0600 mmol), 2-Pyrrolidinone (5.47 μL, 0.0720 mmol), (1S,2S)—N,N'-dimethylcyclohexane-1,2-diamine (1.9 μL, 0.012 mmol), copper(I) iodide (1.14 mg, 0.00600 mmol), and potassium carbonate (17.4 mg, 0.126 mmol) in 1,4-dioxane (0.75 mL) was cooled (dry-ice acetone bath), purged in vacuo, and charged with nitrogen. Then the mixture was heated at 150° C. for 4 h. After cooling, the mixture was diluted with methanol. The resulting solution was purified by RP-HPLC (pH=10) to give the desired product. Analytical LCMS: (M+H)+=427.1.

Example 48

N-Cyclopropyl-4-{3-[1-(4-methoxyphenyl)cyclopropyl][1,2,4]triazolo[4,3-b][1,2,4]triazin-6-yl}benzamide

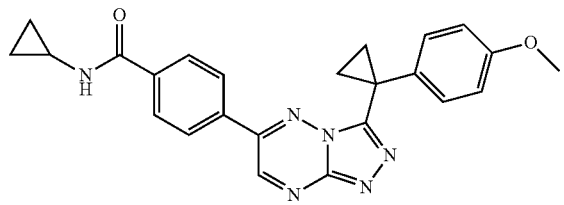

Step 1. 4-(dihydroxyacetyl)benzoic acid

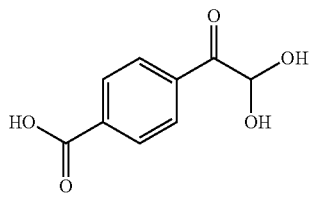

To a solution of 4-acetylbenzoic acid (4.3 g, 0.026 mol) in dimethyl sulfoxide (60 mL) was added slowly an aqueous solution of hydrogen bromide (48%, 8.9 mL) at RT with stirring. Then the mixture was heated at 60° C. overnight. After cooling, the mixture was diluted with ice-water. The precipitate formed was collected by filtration, washed with water, and dried in-vacuo to afford the desired product (4.65 g, 91.1%) which was directly used in next reaction step without further purification.

Step 2. 4-{3-[1-(4-methoxyphenyl)cyclopropyl][1,2,4]triazolo[4,3-b][1,2,4]triazin-6-yl}benzoic acid

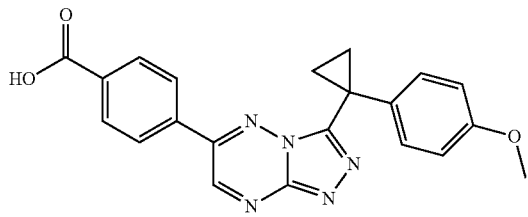

A mixture of 4-(dihydroxyacetyl)benzoic acid hydrate (0.350 g, 1.63 mmol) and 5-[1-(4-methoxyphenyl)cyclopropyl]-4H-1,2,4-triazole-3,4-diamine (0.245 g, 1.00 mmol, prepared as in Example 16, Steps 1-3) in acetic acid (5.00 mL) was stirred at RT overnight. The solvent was evaporated. The residue was purified by RP-HPLC (pH=10) to give the desired product (isomer I: 33 mg, Rt=1.672 min) and 4-{3-[1-(4-methoxyphenyl)cyclopropyl][1,2,4]triazolo[4,3-b][1,2,4]triazin-7-yl}benzoic acid (isomer II: 166 mg, Rt=1.747 min.). Analytical LCMS: (M+H)+=388.3.

Step 3. N-cyclopropyl-4-{3-[1-(4-methoxyphenyl)cyclopropyl][1,2,4]triazolo[4,3-b][1,2,4]-triazin-6-yl}benzamide

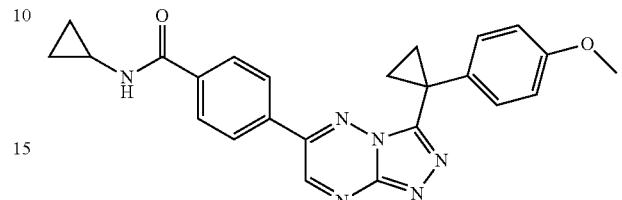

A mixture of 4-{3-[1-(4-methoxyphenyl)cyclopropyl][1,2,4]triazolo[4,3-b][1,2,4]triazin-6-yl}benzoic acid (isomer-I from step 2, 14.0 mg, 0.0361 mmol), cyclopropylamine (3.76 μL, 0.0542 mmol), benzotriazol-1-yloxytris(dimethylamino)phosphonium hexafluorophosphate (16.0 mg, 0.0361 mmol) and N,N-diisopropylethylamine (25.2 μL, 0.145 mmol) in DMF (1.0 mL) was stirred at RT for 3 h. The mixture was diluted with methanol and purified by RP-HPLC (pH=10) to give the desired product. Analytical LCMS: (M+H)+=427.3.

Example 49

4-{3-[1-(4-Methoxyphenyl)cyclopropyl][1,2,4]triazolo[4,3-b][1,2,4]triazin-6-yl}-N-(tetrahydro-2H-pyran-4-yl)benzamide

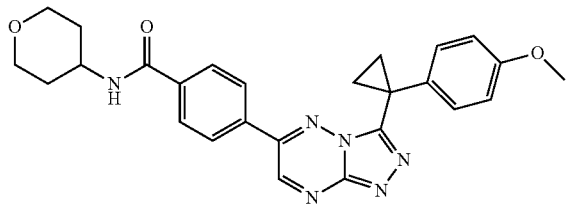

This compound was prepared using procedures analogous to those for Example 48. Analytical LCMS: (M+H)+=471.4.

Example 50

N-(trans-4-Hydroxycyclohexyl)-4-{3-[1-(4-methoxyphenyl)cyclopropyl][1,2,4]triazolo[4,3-b][1,2,4]triazin-6-yl}benzamide

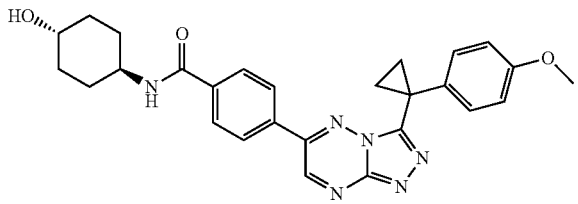

This compound was prepared using procedures analogous to those for Example 48. Analytical LCMS: (M+H)⁺=485.4.

Example 51

Ethyl 4-[(4-{3-[1-(4-methoxyphenyl)cyclopropyl][1,2,4]triazolo[4,3-b][1,2,4]triazin-6-yl}benzoyl)amino]piperidine-1-carboxylate

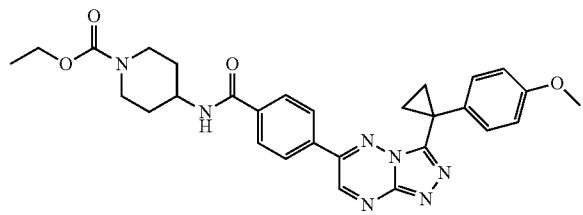

This compound was prepared using procedures analogous to those for Example 48. Analytical LCMS: (M+H)⁺=542.3.

Example 52

4-{3-[1-(4-Methoxyphenyl)cyclopropyl][1,2,4]triazolo[4,3-b][1,2,4]triazin-6-yl}-N-(pyridin-2-ylmethyl)benzamide

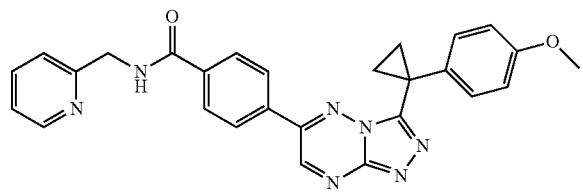

This compound was prepared using procedures analogous to those for Example 48. Analytical LCMS: (M+H)⁺=478.3.

Example 53

Ethyl 1-[(4-{3-[1-(4-methoxyphenyl)cyclopropyl][1,2,4]triazolo[4,3-b][1,2,4]triazin-6-yl}benzoyl)amino]cyclopropanecarboxylate

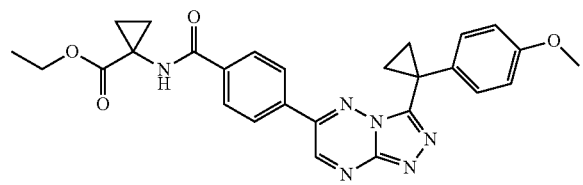

This compound was prepared using procedures analogous to those for Example 48. Analytical LCMS: (M+H)⁺=499.4.

Example 54

N-[1-(6-Fluoropyridin-2-yl)pyrrolidin-3-yl]-4-{3-[1-(4-methoxyphenyl)cyclopropyl][1,2,4]triazolo[4,3-b][1,2,4]triazin-6-yl}benzamide

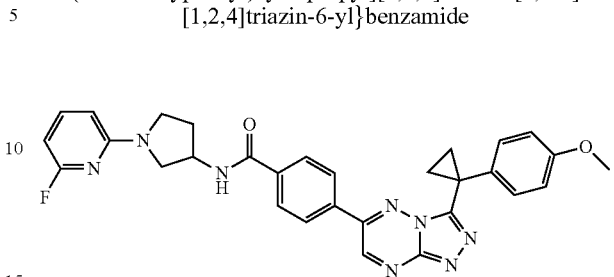

This compound was prepared using procedures analogous to those for Example 48. Analytical LCMS: (M+H)⁺=551.0.

Example 55

4-{3-[1-(4-Methoxyphenyl)cyclopropyl][1,2,4]triazolo[4,3-b][1,2,4]triazin-6-yl-N'-pyridin-2-yl}benzohydrazide

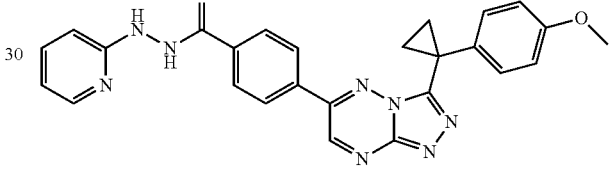

This compound was prepared using procedures analogous to those for Example 48. Analytical LCMS: (M+H)⁺=479.2.

Example 56

6-(1-{6-[3-(1H-imidazol-1-yl)phenyl][1,2,4]triazolo[4,3-b][1,2,4]triazin-3-yl}cyclopropyl)quinoline

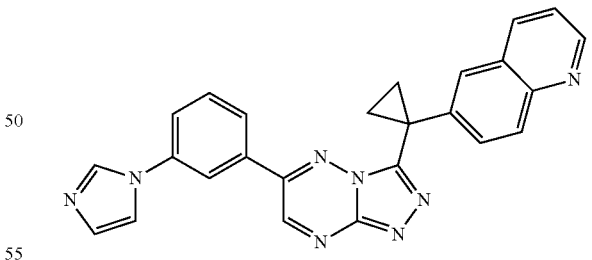

To a solution of 6-{1-[6-(3-bromophenyl)[1,2,4]triazolo[4,3-b][1,2,4]triazin-3-yl]cyclopropyl}quinoline (20 mg, 0.04 mmol) in 1,4-dioxane (1 mL) was added 1H-imidazole (4.61 mg, 0.0677 mmol), sodium iodide (14 mg, 0.090 mmol), (1S,2S)—N,N'-dimethylcyclohexane-1,2-diamine (1 mg, 0.009 mmol), copper(I) iodide (0.8 mg, 0.004 mmol), and cesium carbonate (31 mg, 0.095 mmol), then the mixture was heated at 120° C. overnight. The reaction mixture was cooled to RT and filtered. The filtrate was diluted with MeOH and purified by RP-HPLC (pH=10) to afford the desired compound 8 mg (40%) LCMS: (M+H)⁺=431.1.

Example 57

6-(1-{6-[4-(1H-imidazol-1-yl)phenyl][1,2,4]triazolo[4,3-b][1,2,4]triazin-3-yl}cyclopropyl)quinoline

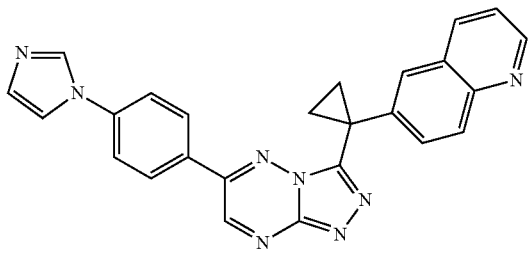

This compound was prepared by using procedures analogous to those for Example 56. Analytical LCMS: (M+H)$^+$=431.1

Example 58

3-{4-[3-(1-Quinolin-6-ylcyclopropyl)[1,2,4]triazolo[4,3-b][1,2,4]triazin-6-yl]phenyl}-1,3-oxazolidin-2-one

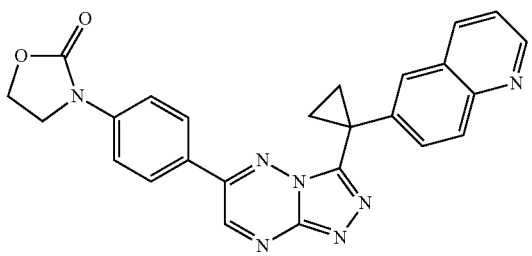

This compound was prepared using procedures analogous to those for Example 56. Analytical LCMS: (M+H)$^+$=450.1

Example 59

6-(1-{6-[3-(6-Methoxypyridin-3-yl)phenyl][1,2,4]triazolo[4,3-b][1,2,4]triazin-3-yl}cyclopropyl)quinoline

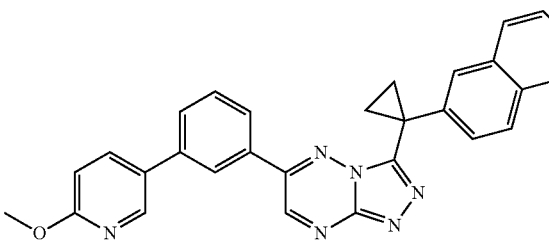

To a mixture of 6-{1-[6-(3-bromophenyl)[1,2,4]triazolo[4,3-b][1,2,4]triazin-3-yl]cyclopropyl}quinoline (16 mg, 0.036 mmol), 2-methoxy-5-(4,4,5,5-tetramethyl-1,3,2-dioxaborolan-2-yl)pyridine (10 mg, 0.043 mmol), and potassium phosphate (30 mg, 0.14 mmol) in 1,4-dioxane (0.5 mL) was added tetrakis(triphenylphosphine)palladium(0) (3 mg) and water (0.1 mL). The resulting mixture was heated at 120° C. overnight. The reaction mixture was cooled to RT and concentrated. The residue was dissolved in MeOH and purified by RP-HPLC (pH=10) to afford the desired compound 10 mg (60%). Analytical LCMS: (M+H)$^+$=472.2.

Example 60

N,N-Dimethyl-5-{3-[3-(1-quinolin-6-ylcyclopropyl)[1,2,4]triazolo[4,3-b][1,2,4]triazin-6-yl]phenyl}pyridine-2-carboxamide

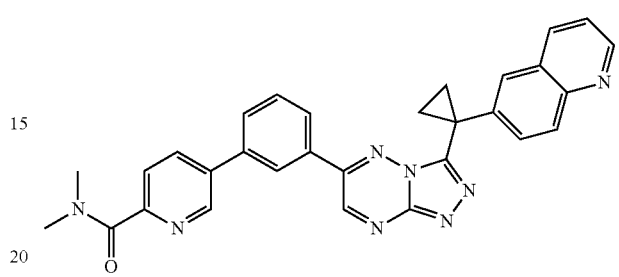

This compound was prepared using procedures analogous to those for Example 59. Analytical LCMS: (M+H)$^+$=513.3.

Example 61

N-Ethyl-5-{3-[3-(1-quinolin-6-ylcyclopropyl)[1,2,4]triazolo[4,3-b][1,2,4]triazin-6-yl]phenyl}pyridine-2-carboxamide

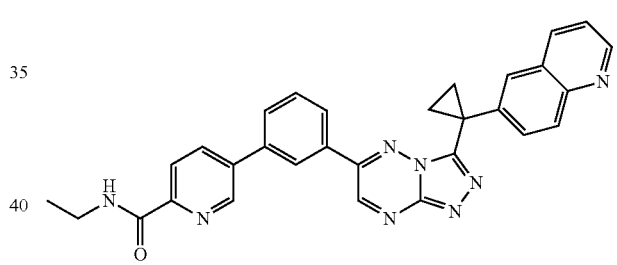

This compound was prepared using procedures analogous to those for Example 59. Analytical LCMS: (M+H)$^+$=513.3

Example 62

N-Methyl-2-(4-{3-[3-(1-quinolin-6-ylcyclopropyl)[1,2,4]triazolo[4,3-b][1,2,4]triazin-6-yl]phenyl}-1H-pyrazol-1-yl)acetamide

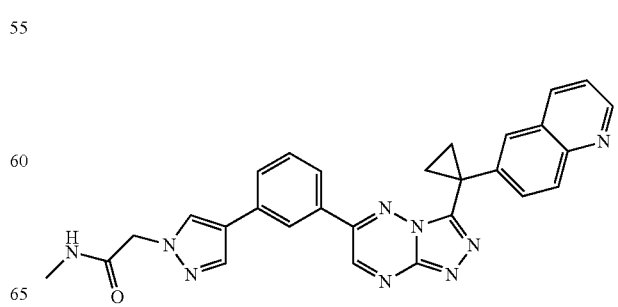

Step 1. Tert-butyl[4-(4,4,5,5-tetramethyl-1,3,2-dioxaborolan-2-yl)-1H-pyrazol-1-yl]acetate

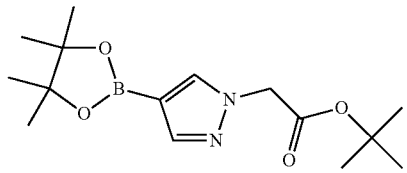

To a solution of 4-(4,4,5,5-tetramethyl-1,3,2-dioxaborolan-2-yl)-1H-pyrazole (1.5 g, 0.0077 mol) in DMF (25 mL) was added 2-bromoacetic acid 1,1-dimethylethyl ester (1.2 mL, 0.0085 mol) and cesium carbonate (3.8 g, 0.012 mol). The suspension was stirred at 90° C. overnight. The reaction mixture was cooled to RT and partitioned with ethyl acetate and water. The organic layer was washed with water, brine, and dried over MgSO$_4$. The solution was concentrated to afford the desired compound (2.0 g, 84%). Analytical LC/MS: (M+H)$^+$=309.4.

Step 2. Tert-butyl (4-{3-[3-(1-quinolin-6-ylcyclopropyl)[1,2,4]triazolo[4,3-b][1,2,4]triazin-6-yl]phenyl}-1H-pyrazol-1-yl)acetate

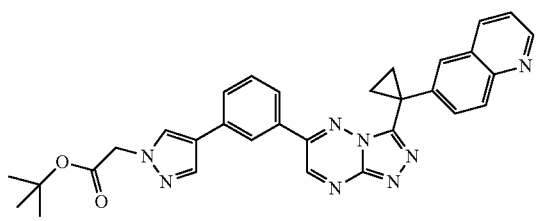

This compound was prepared using procedures analogous to those for Example 59. Analytical LCMS: (M+H)$^+$=545.2.

Step 3. N-Methyl-2-(4-{3-[3-(1-quinolin-6-ylcyclopropyl)[1,2,4]triazolo[4,3-b][1,2,4]triazin-6-yl]phenyl}-1H-pyrazol-1-yl)acetamide

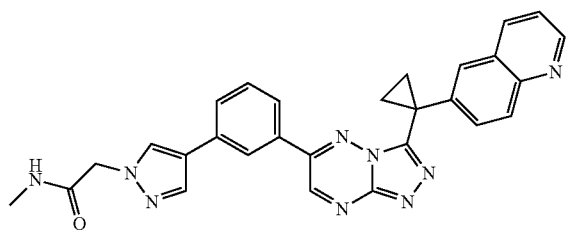

To a solution of tert-butyl (4-{3-[3-(1-quinolin-6-ylcyclopropyl)[1,2,4]triazolo[4,3-b][1,2,4]triazin-6-yl]phenyl}-1H-pyrazol-1-yl)acetate (11 mg, 0.020 mmol) in DCM (2 mL) was added TFA (1 mL). The solution was stirred at RT for 2 h. The volatiles were evaporated under reduced pressure. The residue was co-evaporated with toluene three times.

The above residue was dissolved in DMF (0.5 mL), to this solution was added benzotriazol-1-yloxytris(dimethylamino) phosphonium hexafluorophosphate (10.7 mg, 0.0242 mmol), 2.0 M of methylamine in tetrahydrofuran (20 µL) and N,N-diisopropylethylamine (7.0 µL, 0.040 mmol). The mixture was stirred at RT for 3 h, diluted with methanol, and purified by RP-HPLC (pH=2) to afford the desired compound as a TFA salt. Analytical LCMS: (M+H)+=502.2

Example 63

2-(4-{3-[3-(1-Quinolin-6-ylcyclopropyl)[1,2,4]triazolo[4,3-b][1,2,4]triazin-6-yl]phenyl}-1H-pyrazol-1-yl)-N-(tetrahydrofuran-3-yl)acetamide

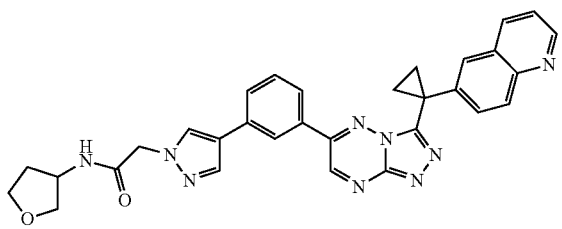

This compound was prepared as a TFA salt using procedures analogous to those for Example 62. Analytical LCMS: (M+H)$^+$=558.2.

Example 64

N-(1-Pyridin-2-ylethyl)-2-(4-{3-[3-(1-quinolin-6-ylcyclopropyl)[1,2,4]triazolo[4,3-b][1,2,4]triazin-6-yl]phenyl}-1H-pyrazol-1-yl)acetamide

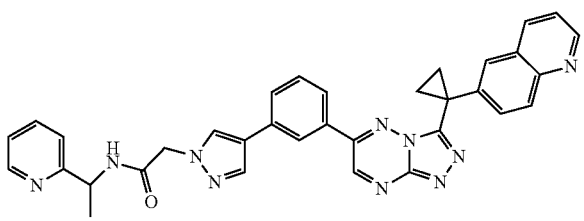

This compound was prepared as a TFA salt using procedures analogous to those for Example 62. Analytical LCMS: (M+H)$^+$=593.2.

Example 65

N,N-Dimethyl-2-(4-{3-[3-(1-quinolin-6-ylcyclopropyl) [1,2,4]triazolo[4,3-b][1,2,4]triazin-6-yl]phenyl}-1H-pyrazol-1-yl)acetamide

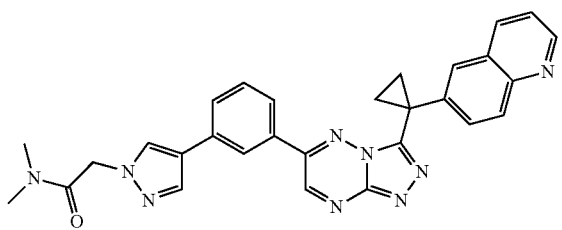

This compound was prepared using procedures analogous to those for Example 62. Analytical LCMS: (M+H)⁺=516.1.

Example 66

N-Methyl-2-(4-{4-[3-(1-quinolin-6-ylcyclopropyl)[1,2,4]triazolo[4,3-b][1,2,4]triazin-6-yl]phenyl}-1H-pyrazol-1-yl)acetamide

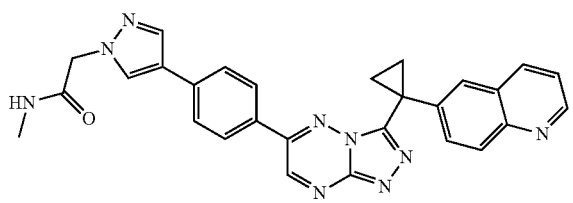

This compound was prepared as a TFA salt using procedures analogous to those for Example 62. Analytical LCMS: (M+H)⁺=502.1.

Example 67

N-Isopropyl-2-(4-{4-[3-(1-quinolin-6-ylcyclopropyl)[1,2,4]triazolo[4,3-b][1,2,4]triazin-6-yl]phenyl}-1H-pyrazol-1-yl)acetamide

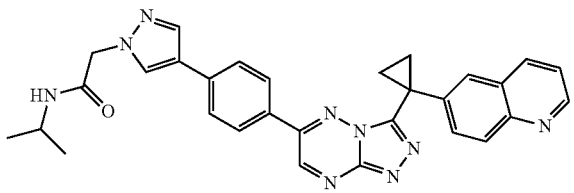

This compound was prepared as a TFA salt using procedures analogous to those for Example 62. Analytical LCMS: (M+H)⁺=530.2.

Example 68

N-(Cyclopropylmethyl)-2-(4-{4-[3-(1-quinolin-6-ylcyclopropyl)[1,2,4]triazolo[4,3-b][1,2,4]triazin-6-yl]phenyl}-1H-pyrazol-1-yl)acetamide

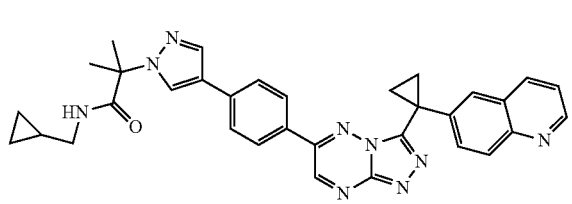

This compound was prepared as a TFA salt using procedures analogous to those for Example 62. Analytical LCMS: (M+H)⁺=570.2.

Example 69

N-Isopropyl-2-methyl-2-(4-{4-[3-(1-quinolin-6-ylcyclopropyl)[1,2,4]triazolo[4,3-b][1,2,4]triazin-6-yl]phenyl}-1H-pyrazol-1-yl)propanamide

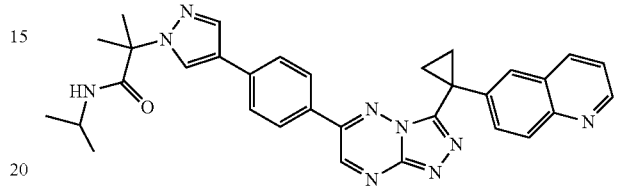

This compound was prepared as a TFA salt using procedures analogous to those for Example 62. Analytical LCMS: (M+H)⁺=558.2

Example 70

6-[1-(6-{4-[1-(1,1-Dimethyl-2-oxo-2-pyrrolidin-1-ylethyl)-1H-pyrazol-4-yl]phenyl}[1,2,4]triazolo[4,3-b][1,2,4]triazin-3-yl)cyclopropyl]quinoline

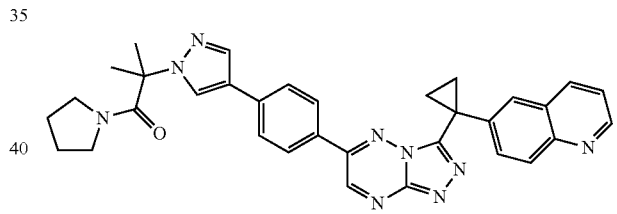

This compound was prepared as a TFA salt using procedures analogous to those for Example 62. Analytical LCMS: (M+H)⁺=570.2.

Example 71

(2R)—N,N-Dimethyl-2-(4-{4-[3-(1-quinolin-6-ylcyclopropyl)[1,2,4]triazolo[4,3-b][1,2,4]triazin-6-yl]phenyl}-1H-pyrazol-1-yl)propanamide

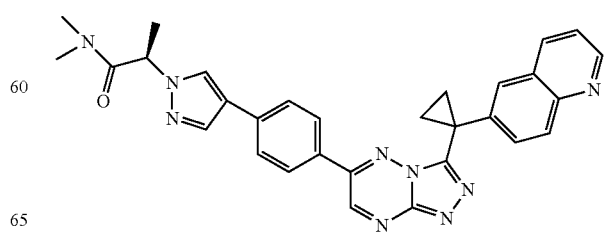

This compound was prepared as a TFA salt using procedures analogous to those for Example 62. Analytical LCMS: (M+H)+=530.1.

Example 72

(2S)—N,N-Dimethyl-2-(4-{4-[3-(1-quinolin-6-ylcyclopropyl)[1,2,4]triazolo[4,3-b][1,2,4]triazin-6-yl]phenyl}-1H-pyrazol-1-yl)propanamide

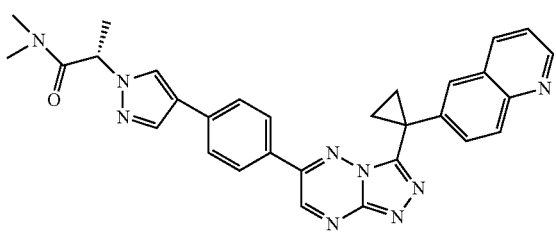

This compound was prepared as a TFA salt using procedures analogous to those for Example 62. Analytical LCMS: (M+H)+=530.2.

Example 73

6-(3-Bromophenyl)-3-[1-(3-methyl[1,2,4]triazolo[4,3-a]pyridin-6-yl)cyclopropyl][1,2,4]triazolo[4,3-b][1,2,4]triazine

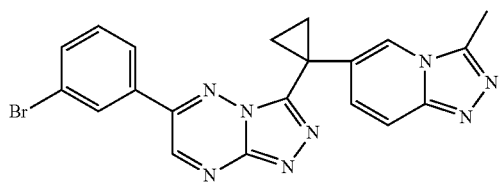

Step 1. (6-Chloropyridin-3-yl)acetonitrile

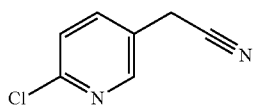

To a solution of 2-chloro-5-(chloromethyl)pyridine (5.0 g, 0.031 mol) in ethanol (38 mL) and water (19 mL) was added potassium cyanide (2.41 g, 0.0370 mol) at RT under nitrogen atmosphere. The reaction mixture was stirred at 50° C. overnight. The reaction was diluted with water and extracted with DCM. The organic layer was washed with brine and dried over sodium sulfate. The solution was filtered and the filtrate was concentrated to afford the desired compound (4.2 g, 89%). Analytical LCMS: (M+H)+=153.1.

Step 2. 1-(6-Chloropyridin-3-yl)cyclopropanecarboxylic acid

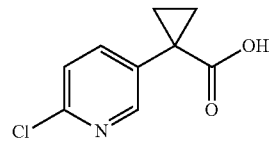

To a stirred mixture of (6-chloropyridin-3-yl)acetonitrile (2.00 g, 0.0131 mol), benzyltriethylammonium chloride (0.2 g, 0.0008 mol), and 1-bromo-2-chloroethane (3.26 mL, 0.0393 mol), was added sodium hydroxide aqueous solution (50%, 3 mL, 0.08 mol) drop-wise at 50° C. The mixture was stirred at 50° C. for 5 h. 1,2-ethanediol (4 mL) was added to the above mixture and stirred at 100° C. overnight. The aqueous layer was acidified to pH ~1, and extracted with ethyl acetate. The organic layer was washed with water and brine, dried with sodium sulfate, filtered, and concentrated to afford the desired compound (2.2 g, 85%). Analytical LCMS: (M+H)+=198.0.

Step 3. Methyl 1-(6-chloropyridin-3-yl)cyclopropanecarboxylate

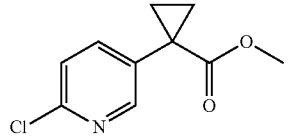

A mixture of 1-(6-chloropyridin-3-yl)cyclopropanecarboxylic acid (2.0 g, 0.010 mol) and sulfuric acid (0.42 mL, 0.0079 mol) in methanol (30 mL) was stirred at 80° C. for 6 h. The mixture was cooled to RT and concentrated. The residue was dissolved in saturated sodium bicarbonate and extracted with ethyl acetate. The organic layers were washed with brine, dried with Na₂SO₄, filtered, and concentrated under reduced pressure to give a crude product (2.0 g, 93%). Analytical LCMS: (M+H)+=212.0.

Step 4. Methyl 1-(6-hydrazinopyridin-3-yl)cyclopropanecarboxylate

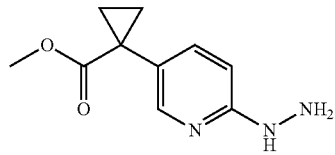

To a solution of methyl 1-(6-chloropyridin-3-yl)cyclopropanecarboxylate (1 g, 0.005 mol) in pyridine (2 mL) was added hydrazine (0.30 mL, 0.0094 mol). The solution was heated at 90° C. overnight. The reaction solution was cooled to RT, and then diluted with a small amount of ice-water. The precipitate was collected by filtration, and dried under vacuum to afford the desired compound (0.9 g, 90%). Analytical LCMS: (M+H)+=208.0.

Step 5. 1-(3-Methyl[1,2,4]triazolo[4,3-a]pyridin-6-yl)cyclopropanecarboxylic acid

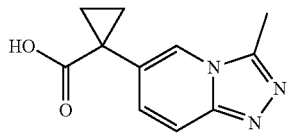

To a solution of methyl 1-(6-hydrazinopyridin-3-yl)cyclopropanecarboxylate (150 mg, 0.72 mol) in ethanol (3 mL) was added acetaldehyde (33.5 mg, 0.760 mmol) and acetic acid (41 µL, 0.72 mmol). The mixture was stirred at RT for 2 h, and then concentrated to dryness. The residue was dissolved in methylene chloride (3 mL), and iodobenzene diacetate (256 mg, 0.796 mmol) was added dropwise. The reaction mixture was stirred at RT overnight. The reaction solution was concentrated to dryness. The residue was purified through silica gel chromatograph using 10% MeOH in $CH_2Cl_2$ to afford the desired compound (50 mg, 30%). Analytical LCMS: $(M+H)^+=218.0$.

Step 6. 6-(3-Bromophenyl)-3-[1-(3-methyl[1,2,4]triazolo[4,3-a]pyridin-6-yl)cyclopropyl][1,2,4]triazolo[4,3-b][1,2,4]triazine

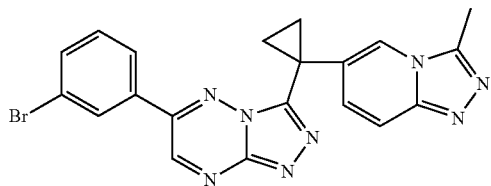

This compound was prepared as a TFA salt using procedures analogous to those for Example 28. Analytical LCMS: $(M+H)^+=447.0$.

Example 74

6-{1-[6-(4-Bromo-3-fluorophenyl)[1,2,4]triazolo[4,3-b][1,2,4]triazin-3-yl]cyclopropyl}quinoline

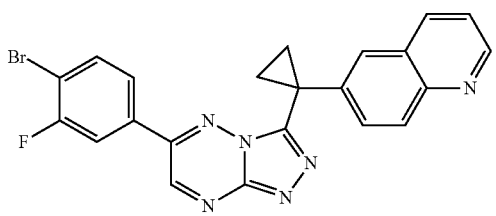

Step 1. 4-Bromo-3-fluoro-N-methoxy-N-methylbenzamide

Oxalyl chloride (38.1 mL, 0.450 mol) was slowly added to a mixture of 4-bromo-3-fluorobenzoic acid (49.3 g, 0.225 mol) in methylene chloride (300 mL), then DMF (1.0 mL) was added and the reaction was stirred at RT for 2 h. The volatiles were removed under reduced pressure and co-evaporated with toluene for 3 times. The residue was then dissolved in methylene chloride (100 mL). The solution was added dropwise to a mixture of N,O-dimethyl-hydroxylamine hydrochloride (30.7 g, 0.315 mol) and potassium carbonate (120 g, 0.90 mol) in methylene chloride (300 mL) and water (300 mL). The reaction was stirred at RT for 2 h. The organic layer was separated. The aqueous layer was extracted with methylene chloride (2×50 mL). The combined organic layers were washed with brine, dried over $MgSO_4$, filtered, and concentrated under reduced pressure to give the product (58.5 g, 99%). Analytical LCMS: $(M+H)^+=261.9/263.9$.

Step 2. 1-(4-Bromo-3-fluorophenyl)ethanone

To a solution of 4-bromo-3-fluoro-N-methoxy-N-methylbenzamide (58.5 g, 0.223 mol) in tetrahydrofuran (500 mL) was added 3.00 M of methylmagnesium chloride in tetrahydrofuran (125 mL, 0.38 mol) at 0° C. The mixture was stirred for 1 h at 0° C., and was quenched with cold saturated $NH_4Cl$ solution (150 mL). The organic layer was separated and concentrated under reduced pressure. The residue was diluted with ethyl acetate (100 mL). The aqueous layer was diluted with water (100 mL) and was extract with ethyl acetate (3×50 mL). The organic solution and extracts were combined, washed with brine, dried over $MgSO_4$, filtered, and concentrated under reduced pressure to give product (48.4 g, 99%) which was directly used in next step without further purification.

Step 3. 1-(4-bromo-3-fluorophenyl)-2,2-dihydroxyethanone

To a solution of 1-(4-bromo-3-fluorophenyl)ethanone (9.0 g, 0.041 mol) in dimethyl sulfoxide (40 mL) was added slowly 48% of hydrogen bromide aqueous solution (14 mL). The reaction was stirred at 60° C. overnight and then cooled to RT, poured into ice-water, the precipitate was filtered and washed with water, and the solid was dried under vacuum overnight (8.1 g was obtained). The aqueous portion was extracted with ethyl acetate three times. The combined extracts were washed with water and brine, dried, filtered, and concentrated to give an additional 2.2 g of the product.

Step 4. 1-(4-bromo-3-fluorophenyl)-2,2-diethoxyethanone

To a solution of 1-(4-bromo-3-fluorophenyl)-2,2-dihydroxyethanone (3.5 g, 0.014 mol) in toluene (30 mL) was added ethyl orthoformate (5.8 mL, 0.035 mol) and p-toluenesulfonic acid (100 mg). The reaction was refluxed for 4 h. After cooled to RT, the mixture was diluted with ethyl acetate, washed with saturated $NaHCO_3$ solution, water, and brine, dried over $MgSO_4$, filtered and concentrated to give the product (4.0 g, 93%) which was used in the next step without further purification.

Step 5. 6-(4-bromo-3-fluorophenyl)-3-(methylthio)-1,2,4-triazine

A solution of 1-(4-bromo-3-fluorophenyl)-2,2-diethoxyethanone (2.24 g, 0.00734 mol), thiosemicarbazide (0.702 g, 0.00771 mol), and p-toluenesulfonic acid monohydrate (70 mg) in ethanol (50 mL) was heated at 90° C. for 2 h. LCMS showed that the starting material was consumed. After cooled to RT, to the mixture was added methyl iodide (2.3 mL, 0.037 mol). The mixture was stirred at RT for 2 h, and concentrated.

To the residue was added acetic acid (15 mL). The mixture was heated at 60° C. for 4 h. The volatiles were evaporated under reduced pressure. The residue was treated with methanol. The formed precipitate was collected by filtration, and dried in-vacuo to afford the desired product (1.15 g, 51%) which was directly used in next step without further purification.

Step 6. 6-(4-bromo-3-fluorophenyl)-3-hydrazino-1,2,4-triazine

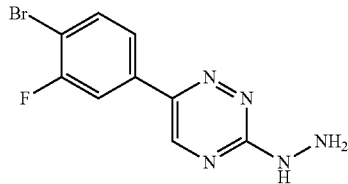

A mixture of 6-(4-bromo-3-fluorophenyl)-3-(methylthio)-1,2,4-triazine (1.15 g, 0.00383 mol) and hydrazine hydrate (0.74 mL, 0.015 mol) in ethanol (50 mL) was heated at 90° C. for 20 h. After cooling, the formed precipitate was collected by filtration, and dried in-vacuo to afford the desired product (0.845 g, 77.6%).

Step 7. quinolin-6-ylacetonitrile

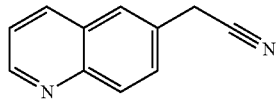

To a mixture of (9,9-dimethyl-9H-xanthene-4,5-diyl)bis(diphenylphosphine) (6.7 g, 0.012 mol), tris(dibenzylideneacetone)dipalladium(0) (10.0 g, 0.012 mol), 6-bromoquinoline (120.0 g, 0.577 mol) in DMF (360 mL) in a 3-neck round bottom flask with stirring under an atmosphere of nitrogen was added (trimethylsilyl)acetonitrile (98.7 mL, 0.721 mol), followed by zinc difluoride (42 g, 0.40 mol). The flask was sealed under an atmosphere of nitrogen. The reaction was stirred at 105° C. for 20 h. After cooling the solution to RT, the reaction mixture was quenched with aqueous ammonia solution and extracted with ethyl acetate (3×500 mL). The combined organic layers were washed with brine, dried over anhydrous Na$_2$SO$_4$, filtered, and concentrated under reduced pressure. The residue was chromatographed on a silica gel column (ethyl acetate in hexanes: 0-65%) to afford the desired product quinolin-6-ylacetonitrile (70 g, 72.1%). Analytical LCMS: (M+H)$^+$=168.9.

Step 8. 1-quinolin-6-ylcyclopropanecarbonitrile

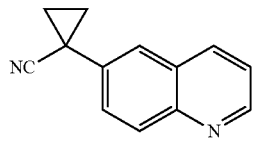

60 mL of 50% aqueous NaOH was added to a mixture of 1-bromo-2-chloroethane (22.0 mL, 0.265 mol), quinolin-6-ylacetonitrile (16.0 g, 0.0666 mol), and benzyltriethylammonium chloride (0.99 g, 0.0043 mol) at 50° C. The mixture was stirred at 50° C. for 3 h. After cooling to RT, the reaction mixture was poured into 100 ml of water, and extracted with DCM (3×100 mL). The combined organic layers were dried over anhydrous Na$_2$SO$_4$, filtered through a pad of silica gel and washed with ethyl acetate in DCM (20%). The filtrate was concentrated to give the crude product 1-quinolin-6-ylcyclopropanecarbonitrile (12.4 g, 96%) which was directly used in the next step without further purification.

Step 9. 1-quinolin-6-ylcyclopropanecarbaldehyde

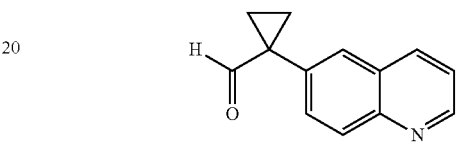

Diisobutylaluminum hydride in THF (1.0 M, 96 mL, 0.096 mol) was added to a solution of 1-quinolin-6-ylcyclopropanecarbonitrile (12.4 g, 0.0639 mol) in toluene (120 mL) at −78° C. under an atmosphere of nitrogen. The reaction mixture was allowed to warm to −5 to 0° C., and stirred at that temperature for 3 h. The mixture was re-cooled to −60° C. Isopropyl alcohol (10 mL) was carefully added dropwise. After stirring for 30 min, the mixture was warmed to −5 to 0° C. The mixture was diluted with ethyl acetate, quenched with water and extracted with ethyl acetate. The combined organic layers were washed with water and brine, dried over anhydrous Na$_2$SO$_4$, filtered through a pad of silica gel and washed with ethyl acetate in hexanes (40%). The filtrate was concentrated to yield the desired 1-quinolin-6-ylcyclopropanecarbaldehyde (12 g, 95.1%).

Step 10. 6-1-[6-(4-bromo-3-fluorophenyl)[1,2,4]triazolo[4,3-b][1,2,4]triazin-3-yl]cyclopropylquinoline

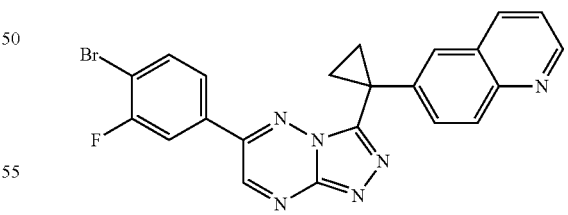

A mixture of 6-(4-bromo-3-fluorophenyl)-3-hydrazino-1,2,4-triazine (0.50 g, 0.0018 mol), 1-quinolin-6-ylcyclopropanecarbaldehyde (0.35 g, 0.0018 mol) in a solution of ethanol (10 mL) and acetic acid (2 mL) was stirred at RT for 4 h. The mixture was concentrated. The residue was suspended in methylene chloride (20 mL). To the suspension was added iodobenzene diacetate (0.62 g, 0.0019 mol) with stirring at RT. The mixture was stirred at RT overnight and concentrated. The residue was purified by flash chromatography on a silica gel column to afford the desired product (579 mg, 71.3%). Analytical LCMS: (M+H)⁺=460.9/462.9.

Example 75

6-(1-{6-[3-Fluoro-4-(1H-imidazol-1-yl)phenyl][1,2,4]triazolo[4,3-b][1,2,4]triazin-3-yl}cyclopropyl)quinoline

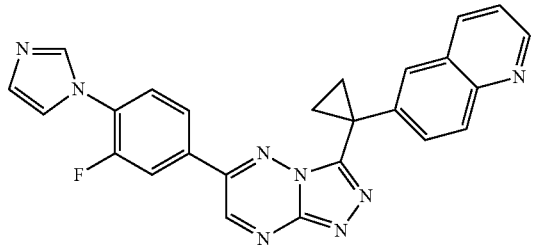

To a solution of 6-1-[6-(4-bromo-3-fluorophenyl) [1,2,4]triazolo[4,3-b][1,2,4]triazin-3-yl]cyclopropylquinoline (20 mg) in 1,4-dioxane (1 mL) was added 1H-imidazole (4.61 mg), sodium iodide (14 mg), (1S,2S)—N,N'-dimethylcyclohexane-1,2-diamine (1 mg), copper(I) iodide (0.8 mg), and cesium carbonate (31 mg). The mixture was heated at 120° C. overnight. The reaction mixture was cooled to RT and filtered. The filtrate was diluted with methanol and purified by RP-HPLC (pH=10) to afford the desired compound. Analytical LCMS: (M+H)⁺=449.1.

Example 76

5-{2-Fluoro-4-[3-(1-quinolin-6-ylcyclopropyl)[1,2,4]triazolo[4,3-b][1,2,4]triazin-6-yl]phenyl}-N,N-dimethylpyridine-2-carboxamide

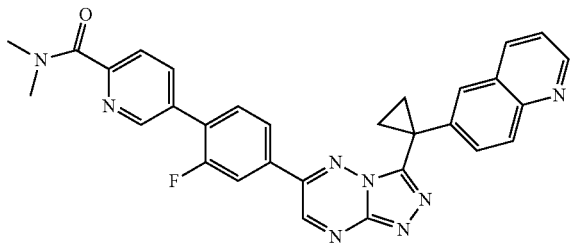

To a mixture of 6-1-[6-(4-bromo-3-fluorophenyl)[1,2,4]triazolo[4,3-b][1,2,4]triazin-3-yl]cyclopropylquinoline (20 mg, 0.04 mmol), 6-[(dimethylamino)carbonyl]pyridin-3-ylboronic acid (13 mg, 0.065 mmol) in 1,4-dioxane (0.5 mL) and water (0.1 mL), was added tetrakis(triphenylphosphine)palladium(0) (3 mg) and potassium phosphate (28 mg). The resulting mixture was heated at 120° C. overnight. The reaction mixture was cooled to RT and concentrated. The residue was dissolved in MeOH and purified by RP-HPLC (pH=10) to afford the desired compound. Analytical LCMS: (M+H)⁺=531.1

Example 77

5-{2-Fluoro-4-[3-(1-quinolin-6-ylcyclopropyl)[1,2,4]triazolo[4,3-b][1,2,4]triazin-6-yl]phenyl}pyridin-2-amine

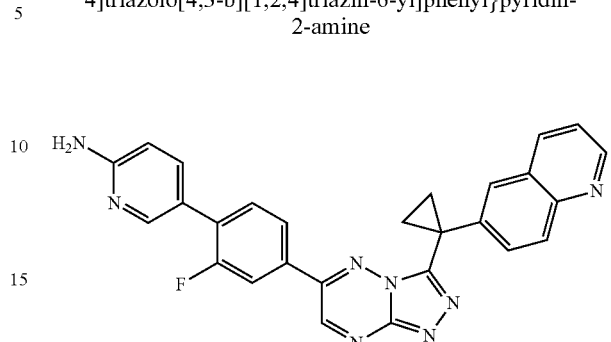

This compound was prepared using procedures analogous to those for Example 76. Analytical LCMS: (M+H)⁺=475.0

Example 78

Methyl (5-{2-fluoro-4-[3-(1-quinolin-6-ylcyclopropyl)[1,2,4]triazolo[4,3-b][1,2,4]triazin-6-yl]phenyl}pyridin-2-yl)carbamate

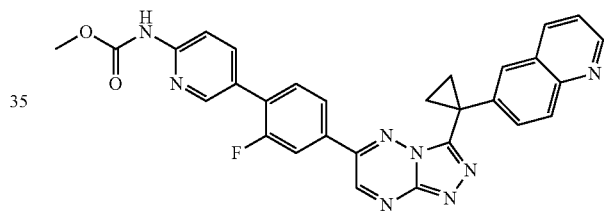

To a solution of 5-{2-fluoro-4-[3-(1-quinolin-6-ylcyclopropyl)[1,2,4]triazolo[4,3-b][1,2,4]triazin-6-yl]phenyl}pyridin-2-amine (20.0 mg, 0.0422 mmol) (Example 77) in DMF (1 mL) was added methyl chloroformate (3.25 µL, 0.0421 mmol) and N,N-diisopropylethylamine (15 µL, 0.084 mmol). The solution was stirred at RT overnight. The reaction solution was diluted with methanol and purified by RP-HPLC (pH=2) to afford the desired compound as a TFA salt (7 mg, 30%). Analytical LCMS: (M+H)⁺=533.1

Example 79

3-[1-(1,3-Benzothiazol-6-yl)cyclopropyl]-6-(4-bromophenyl)[1,2,4]triazolo[4,3-b][1,2,4]triazine

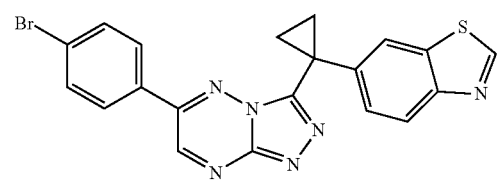

Step 1. 1,3-Benzothiazol-6-ylmethyl methanesulfonate

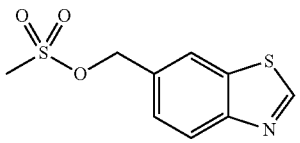

1,3-benzothiazol-6-ylmethanol (1.56 g, 0.00944 mol) and N,N-diisopropylethylamine (2.47 mL, 0.0142 mol) were stirred in methylene chloride (16 mL). The reaction mixture was cooled in an ethylene glycol/water (4/1)/dry ice bath. To the solution was added dropwise a solution of methanesulfonyl chloride (1.10 mL, 0.0142 mol) in DCM (2 mL). After 30 min, the reaction mixture was quenched by adding water, and extracted with ethyl acetate. The combined organic layers were washed with brine, dried over $Na_2SO_4$, filtered, and concentrated under reduced pressure to give the desired product which was directly used in the next step without purification. LCMC: $(M+H)^+=244.2$.

Step 2. 1,3-Benzothiazol-6-ylacetonitrile

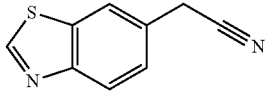

A solution of potassium cyanide (0.68 g, 0.010 mol) in water (3.0 mL) was added under nitrogen to a cooled (with an ethylene glycol/water (4/1)/dry ice bath) solution of 1,3-benzothiazol-6-ylmethanol in DMF (30 mL). The reaction mixture was warmed to 0° C., and stirred for 30 min. Water was added and the reaction mixture was extracted with DCM. The organic layer was washed with brine, dried over $Na_2SO_4$, filtered, and concentrated under reduced pressure. The residue was flash chromatographed on a silica gel column with ethyl acetate in hexane from 10-30% to afford the desired product (1.07 g). Analytical LCMS: $(M+H)^+=175.2$.

Step 3. 1-(1,3-Benzothiazol-6-yl)cyclopropanecarbonitrile

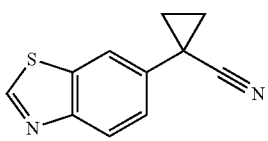

50% aqueous sodium hydroxide (1.51 mL) was added to a mixture of 1,3-benzothiazol-6-ylacetonitrile (586 mg, 3.36 mmol), 1-bromo-2-chloroethane (335 mg, 4.04 mmol), benzyltriethylammonium chloride (76.6 mg, 3.36 mmol) at 50° C. The reaction mixture was stirred at 50° C. for 3 h. Water was added and the mixture was extracted with ethyl acetate. The combined organic layer was washed with brine, dried over $MgSO_4$, filtered, and concentrated under reduced pressure. The residue was flash chromatographed on a silica gel column with ethyl acetate in hexane from 0-30% to afford the desired product (157 mg, 24%). Analytical LCMS: $(M+H)^+=201.2$.

Step 4. 1-(1,3-benzothiazol-6-yl)cyclopropanecarboxylic acid

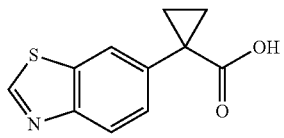

1-(1,3-benzothiazol-6-yl)cyclopropanecarbonitrile (133 mg, 0.664 mmol) was refluxed with 11.3 M of hydrogen chloride in water (5 mL) for 1 h. After cooled to RT, the mixture was extracted with ethyl acetate. The combined organic layers were washed with brine, dried over $NaSO_4$, filtered, and concentrated under reduced pressure to give the desired product. LCMC: $(M+H)^+=219.9$.

Step 5. 3-[1-(1,3-benzothiazol-6-yl)cyclopropyl]-6-(4-bromophenyl)[1,2,4]triazolo[4,3-b][1,2,4]triazine

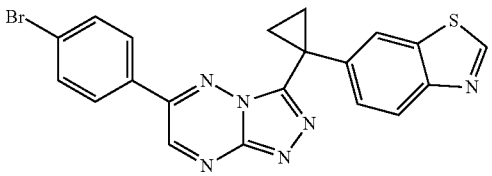

A mixture of 6-(4-bromophenyl)-3-hydrazino-1,2,4-triazine (20.0 mg, 0.0752 mmol) and 1-(1,3-benzothiazol-6-yl)cyclopropanecarboxylic acid (16.5 mg, 0.0752 mmol) in phosphoryl chloride (1 mL) was heated at 130° C. for 8 h. The volatiles were removed under reduced pressure. The residue was dissolved in methanol, and purified by RP-HPLC (pH=10) to give the desired product. LCMC: $(M+H)^+=448.9/451.0$.

Example 80

4-{3-[1-(1,3-Benzothiazol-6-yl)cyclopropyl][1,2,4]triazolo[4,3-b][1,2,4]triazin-6-yl}-N-{(1S)-1-[(dimethylamino)carbonyl]propyl}benzamide

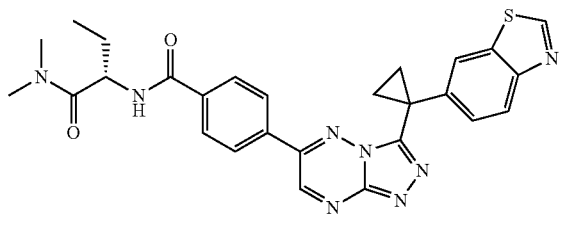

Step 1. 1-(1,3-benzothiazol-6-yl)cyclopropanecarbaldehyde

A solution of diisobutylaluminum hydride in toluene (1.00 M, 2.10 mL, 0.0021 mol) was slowly added to a solution of 1-(1,3-benzothiazol-6-yl)cyclopropanecarbonitrile (0.28 g, 0.0014 mol, prepared in Example 79, Steps 1-3) in toluene (2 mL) at −78° C. The mixture was slowly warmed to RT and stirred overnight. After cooling to −60° C., isopropyl alcohol (0.32 mL) was carefully added. The mixture was warmed to 0° C., and saturated potassium sodium tartrate (50 mL) was added, and stirred at RT for 30 min. The mixture was extracted with ethyl acetate (3×40 mL). The organic layers were washed with brine, dried over anhydrous $Na_2SO_4$, filtered, and concentrated under reduced pressure. The residue was flash chromatographed on a silica gel column with 40% ethyl acetate in hexanes to afford 1-(1,3-benzothiazol-6-yl)cyclopropanecarbaldehyde. Analytical LCMS: (M+H)+= 204.0.

Step 2. methyl 4-{3-[1-(1,3-benzothiazol-6-yl)cyclopropyl][1,2,4]triazolo[4,3-b][1,2,4]triazin-6-yl}benzoate A mixture of 1-(1,3-benzothiazol-6-yl)cyclopropanecarbaldehyde (80.0 mg, 0.39 mmol) and methyl 4-(3-hydrazino-1,2,4-triazin-6-yl)benzoate (96.5 mg, 0.394 mol) in ethanol (2.7 mL) and acetic acid (0.53 mL) was stirred at RT for 3 h. The mixture was concentrated. The residue was dissolved in DCM (5 mL), followed by addition iodobenzene diacetate (150 mg, 0.47 mmol). The mixture was stirred at RT for 6 h, and quenched with saturated sodium bicarbonate (25 mL). The mixture was extracted with ethyl acetate (3×40 mL). The combined organic layers were washed with brine, dried over $Na_2SO_4$, filtered, and concentrated under reduced pressure. The residue was flash chromatographed on a silica gel column with 40% ethyl acetate in DCM to afford the desired product. Analytical LCMS: (M+H)+=429.0.

Step 3. 4-{3-[1-(1,3-benzothiazol-6-yl)cyclopropyl][1,2,4]triazolo[4,3-b][1,2,4]triazin-6-yl}benzoic acid A mixture of methyl 4-{3-[1-(1,3-benzothiazol-6-yl)cyclopropyl][1,2,4]triazolo[4,3-b][1,2,4]triazin-6-yl}benzoate (80.0 mg, 0.19 mmol) and lithium hydroxide monohydrate (16.0 mg, 0.37 mmol) in methanol (3.0 mL) and water (1.0 mL) was stirred at RT for 4 h. The mixture was adjusted with 1N HCl to pH=5. The volatiles were removed under reduced pressure, and dried in-vacuo to give a crude product which was directly used in the next step without further purification. Analytical LCMS: (M+H)+=415.0.

Step 4. (2S)-2-amino-N,N-dimethylbutanamide hydrochloride

Triethylamine (201.9 μL, 1.500 mmol) was added to a solution of (2S)-2-[(tert-butoxycarbonyl)amino]butanoic acid (101.6 mg, 0.500 mmol) and benzotriazol-1-yloxytris (dimethylamino)phosphonium hexafluorophosphate (221.1 mg, 0.500 mmol) in DCM (5 mL), followed by addition of 2.0 M of dimethylamine in tetrahydrofuran (0.500 mL). The mixture was stirred at RT for 4 h. The organic layer was separated. The aqueous layer was extracted with DCM (3×5 mL). The combined organic layers were washed with $NaHCO_3$ (7.5%), and brine, dried over $Na_2SO_4$, filtered, and concentrated. The residue was treated with HCl in dioxane (4 M, 1.0 mL) at RT for 4 h. The volatiles were evaporated under reduced pressure. The residue was washed with ether and dried in-vacuo to give the desired product which was directly used in the next step without further purification. Analytical LCMS: (M+H)+= 131.1.

Step 5. 4-{3-[1-(1,3-benzothiazol-6-yl)cyclopropyl][1,2,4]triazolo[4,3-b][1,2,4]triazin-6-yl}-N-{(1S)-1-[(dimethylamino)carbonyl]propyl}benzamide N,N-Diisopropylethylamine (14 μL, 0.080 mmol) was added to a mixture of 4-{3-[1-(1,3-benzothiazol-6-yl)cyclopropyl][1,2,4]triazolo[4,3-b][1,2,4]triazin-6-yl}benzoic acid (11 mg, 0.026 mmol), (2S)-2-amino-N,N-dimethylbutanamide hydrochloride (5.8 mg, 0.034 mmol) and benzotriazol-1-yloxytris(dimethylamino)phosphonium hexafluorophosphate (14 mg, 0.032 mmol) in DMF (0.4 mL). The mixture was stirred at RT overnight. The residue was diluted with methanol, and purified by RP-HPLC (pH=10) to afford the desired product. Analytical LCMS: (M+H)+=527.0

Example 81

4-{3-[1-(1,3-Benzothiazol-6-yl)cyclopropyl][1,2,4]triazolo[4,3-b][1,2,4]triazin-6-yl}-N-{(1S)-1-[(dimethylamino)carbonyl]-2-methylpropyl}benzamide

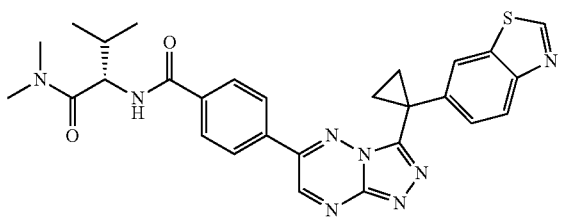

This compound was prepared using procedures analogous to those for Example 80. Analytical LCMS: (M+H)+=541.1.

Example 82

4-{3-[1-(1,3-Benzothiazol-6-yl)cyclopropyl][1,2,4]triazolo[4,3-b][1,2,4]triazin-6-yl}-N-{(1S)-1-[(dimethylamino)carbonyl]-2,2-dimethylpropyl}benzamide

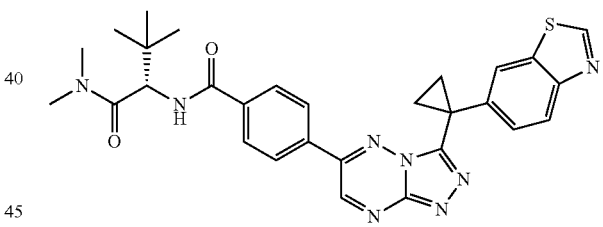

Step 1. Tert-butyl(2S)-2-[(4-{3-[1-(1,3-benzothiazol-6-yl)cyclopropyl][1,2,4]triazolo[4,3-b][1,2,4]triazin-6-yl}benzoyl)amino]-3,3-dimethylbutanoate N,N-Diisopropylethylamine (42 μL, 0.24 mmol) was added to a mixture of 4-{3-[1-(1,3-benzothiazol-6-yl)cyclopropyl][1,2,4]triazolo[4,3-b][1,2,4]triazin-6-yl}benzoic acid (33 mg, 0.080 mmol), tert-butyl (2S)-2-amino-3,3-dimethylbutanoate hydrochloride (23 mg, 0.10 mmol) and benzotriazol-1-yloxytris(dimethylamino)phosphonium hexafluorophosphate (42 mg, 0.096 mmol) in DMF (1 mL). The mixture was stirred at RT overnight, and quenched with saturated sodium bicarbonate (5 mL). The reaction mixture was extracted with ethyl acetate (3×5 mL). The combined organic layers were washed with brine, dried over anhydrous $Na_2SO_4$, filtered, and concentrated under reduced pressure. The residue was flash chromatographed on a silica gel column with ethyl acetate in hexanes (40%) to afford the desired product. Analytical LCMS: (M+H)+=584.2

Step 2. (2S)-2-[(4-{3-[1-(1,3-Benzothiazol-6-yl)cyclopropyl][1,2,4]triazolo[4,3-b][1,2,4]triazin-6-yl}benzoyl)amino]-3,3-dimethylbutanoic acid A mixture of tert-butyl (2S)-2-[(4-{3-[1-(1,3-benzothiazol-6-yl)cyclopropyl][1,2,4]-triazolo[4,3-b][1,2,4]triazin-6-yl}benzoyl)amino]-3,3-dimethylbutanoate (33.0 mg, 0.056 mmol) in trifluoroacetic acid (1.0 mL) and methylene chloride (1.0 mL) was stirred at RT for 2 h. The volatiles were evaporated under reduced pressure to afford the desired product which was directly used in the next step without further purification. Analytical LCMS: (M+H)$^+$=528.0.

Step 3. 4-{3-[1-(1,3-Benzothiazol-6-yl)cyclopropyl][1,2,4]triazolo[4,3-b][1,2,4]triazin-6-yl}-N-{(1S)-1-[(dimethylamino)carbonyl]-2,2-dimethylpropyl}benzamide N,N-Diisopropylethylamine (14 µL, 0.080 mmol) was added to a mixture of (2S)-2-[(4-{3-[1-(1,3-benzothiazol-6-yl)cyclopropyl][1,2,4]triazolo[4,3-b][1,2,4]triazin-6-yl}benzoyl)amino]-3,3-dimethylbutanoic acid (14 mg, 0.026 mmol), dimethylamine (0.034 mmol) and benzotriazol-1-yloxytris(dimethylamino)phosphonium hexafluorophosphate (14 mg, 0.032 mmol) in DMF (0.4 mL). The mixture was stirred at RT overnight. The residue was diluted with methanol, and purified by RP-HPLC (pH=10) to afford the desired product. Analytical LCMS: (M+H)$^+$=555.1.

Example 83

6-(1-{6-[4-(1-Methyl-1H-pyrazol-4-yl)phenyl][1,2,4]triazolo[4,3-b][1,2,4]triazin-3-yl}cyclopropyl)quinoline

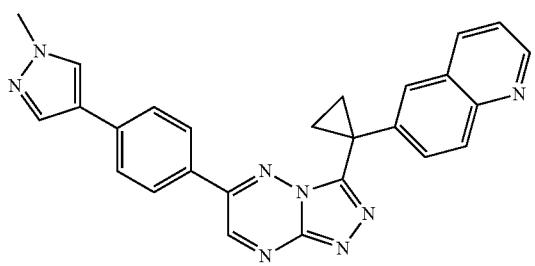

A mixture of 6-{1-[6-(4-bromophenyl)[1,2,4]triazolo[4,3-b][1,2,4]triazin-3-yl]cyclopropyl}quinoline (25 mg, 0.056 mmol, Example 41), 1-methyl-4-(4,4,5,5-tetramethyl-1,3,2-dioxaborolan-2-yl)-1H-pyrazole (18 mg, 0.084 mmol), tetrakis(triphenylphosphine) palladium(0) (4 mg, 0.003 mmol), sodium carbonate (18 mg, 0.17 mmol) in ethanol (400 µL) and toluene (400 µL) was heated at 150° C. for 2 h, then at 120° C. overnight. The mixture was concentrated. The residue was diluted with methanol and filtered. The filtrate was purified by RP-HPLC (pH=2) to afford the desired product as a TFA salt. Analytical LCMS: (M+H)$^+$=445.1.

Example 84

N-Methyl-5-{4-[3-(1-quinolin-6-ylcyclopropyl)[1,2,4]triazolo[4,3-b][1,2,4]triazin-6-yl]phenyl}pyridine-2-carboxamide

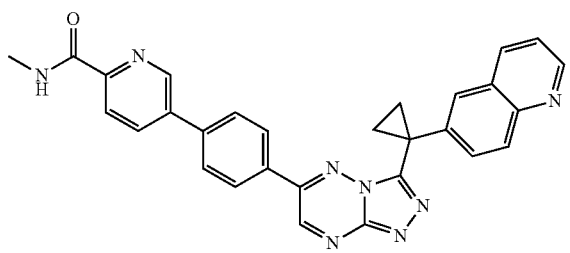

This compound was prepared using procedures analogous to those for Example 83. Analytical LCMS: (M+H)$^+$=499.1.

Example 85

N,N-Dimethyl-5-4-[3-(1-quinolin-6-ylcyclopropyl)[1,2,4]triazolo[4,3-b][1,2,4]triazin-6-yl]phenylpyridine-2-carboxamide

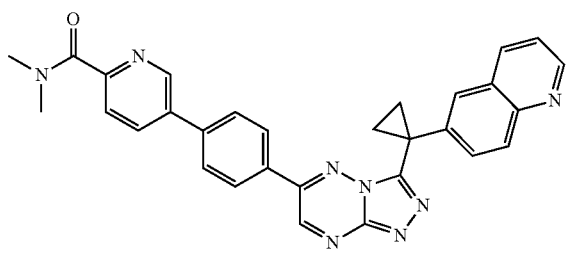

This compound was prepared using procedures analogous to those for Example 83. Analytical LCMS: (M+H)$^+$=513.1.

Example 86

6-(1-{6-[4-(1H-pyrazol-1-yl)phenyl][1,2,4]triazolo[4,3-b][1,2,4]triazin-3-yl}cyclopropyl)quinoline

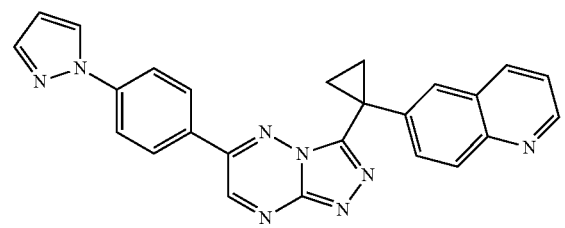

A mixture of 6-{1-[6-(4-bromophenyl) [1,2,4]triazolo[4,3-b][1,2,4]triazin-3-yl]cyclopropyl}quinoline (20 mg, 0.04 mmol, Example 41), 1H-pyrazole (4.6 mg, 0.068 mmol), potassium phosphate (20 mg, 0.095 mmol), N,N'-dimethyl-cyclohexane-1,2-diamine (1.4 µL), and copper(I) iodide (1.7 mg) in 1,4-dioxane (500 µL) was heated at 150° C. for 2 h. After cooling, the mixture was diluted with methanol and filtered. The filtrate was purified by RP-HPLC (pH=10) to afford the desired product. Analytical LCMS: (M+H)⁺= 431.1.

Example 87

N-(Cyclopropylmethyl)-4-[3-(1-quinolin-6-ylcyclopropyl)[1,2,4]triazolo[4,3-b][1,2,4]triazin-6-yl]benzamide

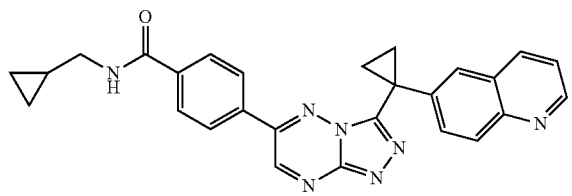

Step 1. Methyl 4-(oxoacetyl)benzoate

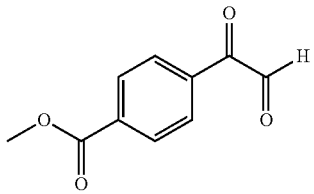

To a solution of 4-acetylbenzoic acid methyl ester (25 g, 0.14 mol) in dimethyl sulfoxide (300 mL) was added slowly a solution of hydrogen bromide in water (48%, 48 mL) at RT with stirring. The mixture was stirred at 60° C. overnight. After cooling it was poured into ice-water. The formed precipitate was collected by filtration and dried in-vacuo to afford the desired product (15.6 g, 79%).

Step 2. Methyl 4-(diethoxyacetyl)benzoate

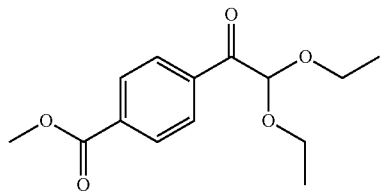

A mixture of methyl 4-(oxoacetyl)benzoate (13.5 g, 0.0702 mol), ethyl orthoformate (29 mL, 0.18 mol), p-toluenesulfonic acid monohydrate (0.7 g) in toluene (150 mL) was heated under reflux for 2 h. After cooling, the solvent was removed under reduced pressure. The crude material was flash chromatographed on a silica gel column to afford the desired product (15.4 g, 82%). Analytical LCMS: (M+Na)⁺= 289.0.

Step 3. Methyl 4-(3-oxo-2,3-dihydro-1,2,4-triazin-6-yl)benzoate

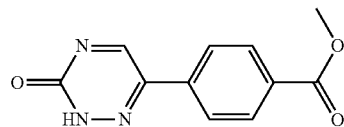

A mixture of methyl 4-(diethoxyacetyl)benzoate (15.4 g, 0.0578 mol), semicarbazide hydrochloride (7.1 g, 0.064 mol), N,N-diisopropylethylamine (12 mL, 0.069 mol) in 1,2-dichloroethane (150 mL), and methanol (2 mL) was heated at 95° C. for 4 h. To the mixture was added an additional 0.1 equivalents of semicarbazide hydrochloride. The mixture was stirred at 95° C. for 1 h. After cooling, the mixture was diluted with methylene chloride and washed with water and brine, dried over Na₂SO₄, filtered, and concentrated. The residue was refluxed with acetic acid (100 mL) and water (1.0 mL) overnight. The mixture was concentrated to yield quantitative crude material which was directly used in the next step without further purification.

Step 4. Methyl 4-(3-chloro-1,2,4-triazin-6-yl)benzoate

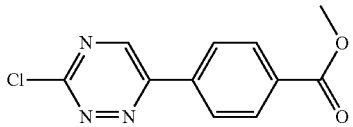

A mixture of methyl 4-(3-oxo-2,3-dihydro-1,2,4-triazin-6-yl)benzoate (13.4 g, 0.0580 mol), phosphoryl chloride (30 mL, 0.3 mol) in chloroform (50 mL) was heated at reflux (oil-bath temperature about 100° C.) for 2 h. After cooling, the mixture was concentrated to remove excess phosphoryl chloride. The residue was dissolved in DCM. The solution was poured into ice-water, and carefully neutralized with K₂CO₃. The organic layer was separated. The aqueous solution was extracted with methylene chloride. The combined extracts were dried over Na₂SO₄. After filtration the filtrate was concentrated and further purified by flash column to afford the desired product (2.5 g, 17%). Analytical LCMS: (M+H)⁺=249.9. ¹H NMR (300 MHz, CDCl₃): δ (ppm) 3.98 (s, 3H), 8.18 (d, 2H), 8.24 (d, 2H), 8.96 (s, 1H).

Step 5. Methyl 4-(3-hydrazino-1,2,4-triazin-6-yl)benzoate

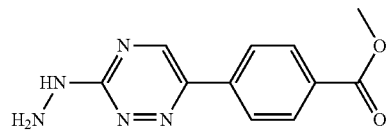

To a solution of methyl 4-(3-chloro-1,2,4-triazin-6-yl)benzoate (1.1 g, 0.0044 mol) in tetrahydrofuran (30 mL) was added hydrazine hydrate (1.1 mL, 0.022 mol) at RT with stirring. The mixture was stirred at RT for 1 h, and concentrated under reduced pressure to give the desired product (quantitatively). Analytical LCMS: (M+H)⁺=245.9.

Step 6. Methyl 4-[3-(1-quinolin-6-ylcyclopropyl)[1,2,4]triazolo[4,3-b][1,2,4]triazin-6-yl]benzoate

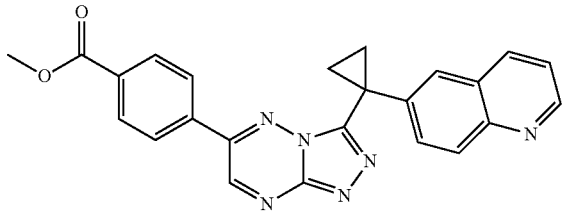

A mixture of methyl 4-(3-hydrazino-1,2,4-triazin-6-yl)benzoate (115 mg, 0.000469 mol) and 1-quinolin-6-ylcyclopropanecarbaldehyde (92 mg, 0.00047 mol) in ethanol (2 mL) and acetic acid (0.5 mL) was stirred at RT for 6 h. The volatiles were removed under reduced pressure. The residue was dried under high vacuum, and then dissolved in methylene chloride (6 mL). To the solution was added iodobenzene diacetate (180 mg, 0.00056 mol). The reaction mixture was stirred at RT overnight. The solvent was evaporated and the residue was flash chromatographed on a silica gel column to afford the desired product (120 mg, 60%). Analytical LCMS: (M+H)⁺=423.3.

Step 7. N-(Cyclopropylmethyl)-4-[3-(1-quinolin-6-ylcyclopropyl)[1,2,4]triazolo[4,3-b][1,2,4]triazin-6-yl]benzamide

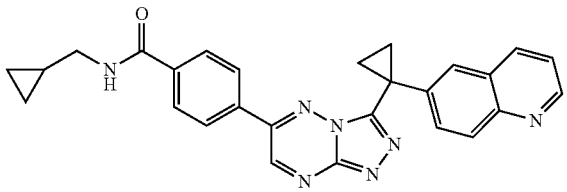

To a solution of methyl 4-[3-(1-quinolin-6-ylcyclopropyl)[1,2,4]triazolo[4,3-b][1,2,4]triazin-6-yl]benzoate (15 mg, 0.036 mmol) in toluene (0.2 mL) was added 2.0 M of trimethylaluminum in toluene (27 µL) at RT followed by addition of cyclopropylmethylamine (5.0 mg, 0.071 mmol). The mixture was stirred at 70° C. overnight. After cooling the mixture was diluted with methanol, and filtered. The filtrate was purified by RP-HPLC (pH=10) to afford the desired product. Analytical LCMS: (M+H)⁺=462.4.

Example 88

N-Ethyl-4-[3-(1-quinolin-6-ylcyclopropyl)[1,2,4]triazolo[4,3-b][1,2,4]triazin-6-yl]benzamide

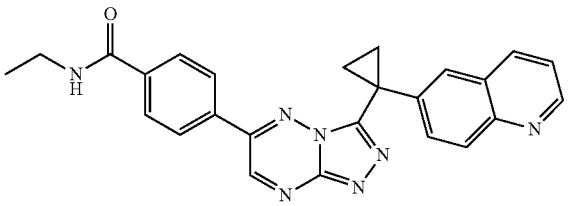

This compound was prepared using procedures analogous to those for Example 87. Analytical LCMS: (M+H)⁺=436.0.
¹H-NMR (400 MHz, DMSO-d₆): 1.12 (t, 3H), 1.72 (m, 2H), 1.84 (m, 2H), 3.28 (q, 2H), 7.66 (m, 1H), 7.82 (d, 1H), 7.96 (m, 2H), 8.02 (m, 3H), 8.06 (d, 1H), 8.58 (m, 1H), 8.62 (m, 1H), 9.00 (m, 1H), 9.38 (s, 1H).

Example 89

N,N-Dimethyl-4-[3-(1-quinolin-6-ylcyclopropyl)[1,2,4]triazolo[4,3-b][1,2,4]triazin-6-yl]benzamide

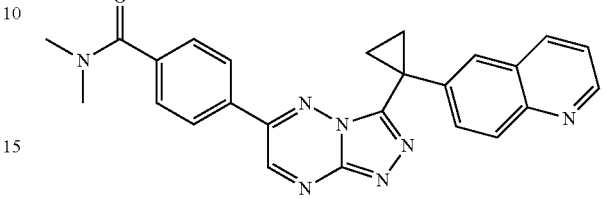

This compound was prepared using procedures analogous to those for Example 87. Analytical LCMS: (M+H)⁺=436.0.

Example 90

N-Cyclopropyl-4-[3-(1-quinolin-6-ylcyclopropyl)[1,2,4]triazolo[4,3-b][1,2,4]triazin-6-yl]benzamide

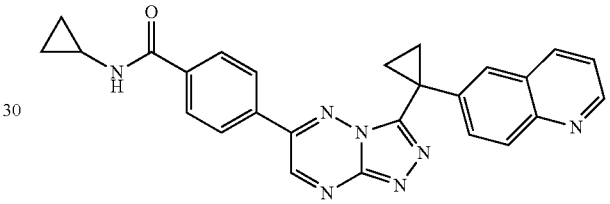

This compound was prepared using procedures analogous to those for Example 87. Analytical LCMS: (M+H)⁺=448.4.

Example 91

N-(Pyridin-2-ylmethyl)-4-[3-(1-quinolin-6-ylcyclopropyl)[1,2,4]triazolo[4,3-b][1,2,4]triazin-6-yl]benzamide

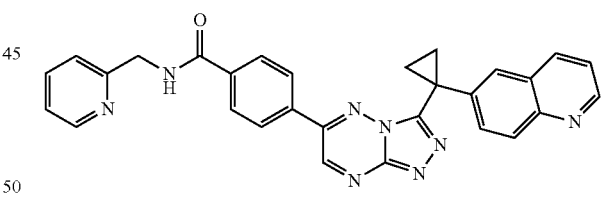

Step 1. 4-[3-(1-quinolin-6-ylcyclopropyl)[1,2,4]triazolo[4,3-b][1,2,4]triazin-6-yl]benzoic acid

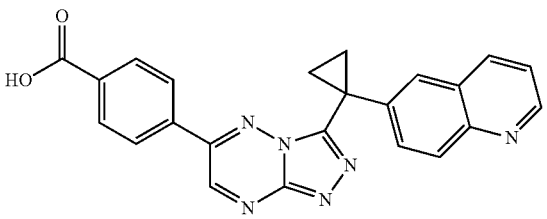

Methyl 4-[3-(1-quinolin-6-ylcyclopropyl)[1,2,4]triazolo[4,3-b][1,2,4]triazin-6-yl]benzoate (300 mg, 0.7 mmol) was dissolved in 6 ml of THF-MeOH—H₂O (3:1:1). To the solution was added a solution of 2.0 M of lithium hydroxide in water (710 μL) with stirring under N₂ atmosphere. The mixture was stirred at RT for 1 h, and then neutralized with aqueous HCl solution (1.0 M, 1.420 mL). The white precipitate formed was collected by filtration, and dried in-vacuo to give the desired product (210 mg, 72%). Analytical LCMS: m/z 409.0 (M+H).

Step 2. N-(pyridin-2-ylmethyl)-4-[3-(1-quinolin-6-ylcyclopropyl)[1,2,4]triazolo[4,3-b][1,2,4]triazin-6-yl]benzamide

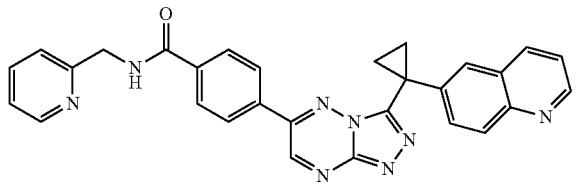

A mixture of 4-[3-(1-quinolin-6-ylcyclopropyl)[1,2,4]triazolo[4,3-b][1,2,4]triazin-6-yl]benzoic acid (10 mg, 0.00002 mol), 2-pyridinemethanamine (2.9 mg, 0.000027 mol), benzotriazol-1-yloxytris(dimethylamino)phosphonium hexafluorophosphate (12 mg, 0.000027 mol), N,N-diisopropylethylamine (11 μL, 0.000061 mol) in DMF (0.4 mL) was stirred at RT for 2 h. The mixture was diluted with methanol and purified by RP-HPLC (pH=10) to afford the desired product. Analytical LCMS: (M+H)⁺=499.1.

Example 92

Ethyl 4-{4-[3-(1-Quinolin-6-ylcyclopropyl)[1,2,4]triazolo[4,3-b][1,2,4]triazin-6-yl]benzoyl}piperazine-1-carboxylate

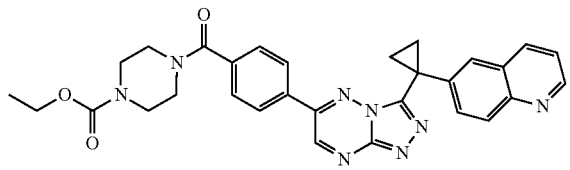

This compound was prepared using procedures analogous to those for Example 91. Analytical LCMS: (M+H)⁺=549.2.

Example 93

6-(1-{6-[4-(Pyrrolidin-1-ylcarbonyl)phenyl][1,2,4]triazolo[4,3-b][1,2,4]triazin-3-yl}cyclopropyl)quinoline

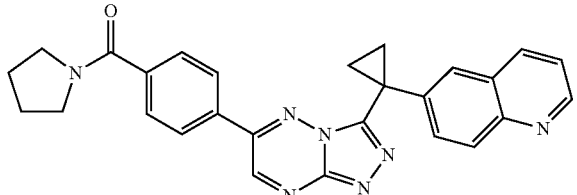

This compound was prepared using procedures analogous to those for Example 91. Analytical LCMS: (M+H)⁺=462.1.

Example 94

6-[1-(6-{4-[(3,3-Difluoropyrrolidin-1-yl)carbonyl]phenyl}[1,2,4]triazolo[4,3-b][1,2,4]triazin-3-yl)cyclopropyl]quinoline

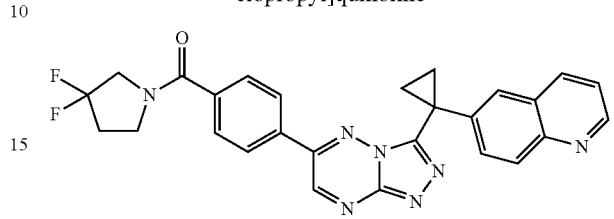

This compound was prepared using procedures analogous to those for Example 91. Analytical LCMS: (M+H)⁺=498.1.

Example 95

6-{1-[6-(4-{[3-(3-Fluorophenyl)pyrrolidin-1-yl]carbonyl}phenyl)[1,2,4]triazolo[4,3-b][1,2,4]triazin-3-yl]cyclopropyl}quinoline

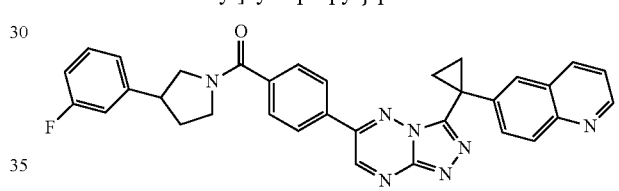

This compound was prepared using procedures analogous to those for Example 91. Analytical LCMS: (M+H)⁺=556.1.

Example 96

6-{1-[6-(4-{[(3S)-3-Fluoropyrrolidin-1-yl]carbonyl}phenyl)[1,2,4]triazolo[4,3-b][1,2,4]triazin-3-yl]cyclopropyl}quinoline

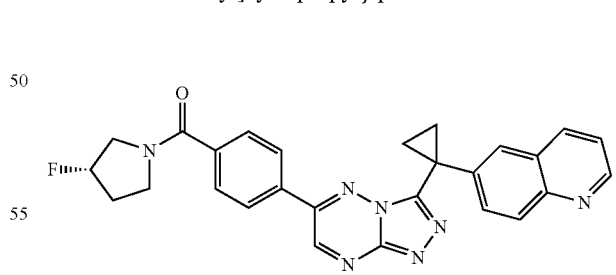

This compound was prepared using procedures analogous to those for Example 91. Analytical LCMS: (M+H)⁺=480.1.
¹H-NMR (400 MHz, CD₃OD): 9.27 (s, 1H), 8.79 (dd, J=4.4, 1.6 Hz, 1H), 8.34 (d, J=7.6 Hz, 1H), 8.04 (m, 3H), 7.98 (d, J=8.8 Hz, 1H), 7.85 (dd, J=9.0, 2.2 Hz, 1H), 7.67 (dd, J=8.4, 5.4 Hz, 2H), 7.57 (dd, J=8.4, 4.4 Hz, 1H), 5.30 (m, 1H), 3.88-3.53 (m, 4H), 2.36-2.14 (m, 2H), 1.91 (m, 2H), 1.77 (m, 2H).

Example 97

4-[3-(1-Quinolin-6-ylcyclopropyl) [1,2,4]triazolo[4,3-b][1,2,4]triazin-6-yl]-N-[(2S)-tetrahydrofuran-2-ylmethyl]benzamide

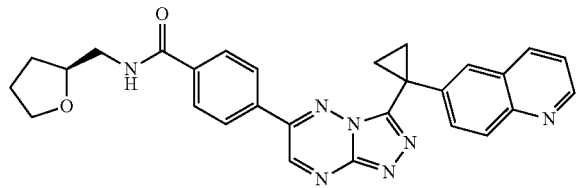

This compound was prepared using procedures analogous to those for Example 91. Analytical LCMS: (M+H)⁺=492.1.

Example 98

N-(1-Pyridin-2-ylcyclopropyl)-4-[3-(1-quinolin-6-ylcyclopropyl)[1,2,4]triazolo[4,3-b][1,2,4]triazin-6-yl]benzamide

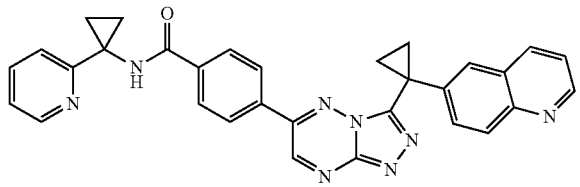

Step 1. 1-pyridin-2-ylcyclopropanamine

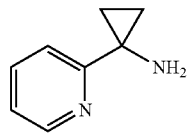

To a solution of 2-pyridinecarbonitrile (1.00 g, 9.60 mmol) in ether (30 mL) were added successively at RT titanium tetraisopropoxide (3.1 mL, 10.0 mmol) and 1.0 M of ethylmagnesium bromide in tetrahydrofuran (19 mL). After the mixture was stirred for 30 min, water (5.0 mL) was added. The mixture was extracted with diethyl ether. The combined organic layers were washed with brine, dried over MgSO₄, filtered, and concentrated to afford the crude product which was directly used in the next step without further purification.

Step 2. N-(1-pyridin-2-ylcyclopropyl)-4-[3-(1-quinolin-6-ylcyclopropyl)[1,2,4]triazolo[4,3-b][1,2,4]triazin-6-yl]benzamide

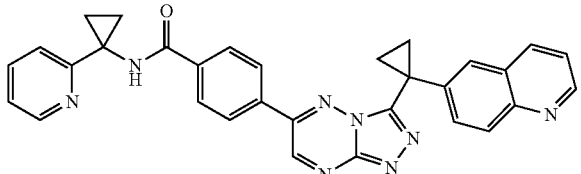

This compound was prepared using procedures analogous to those for Example 91. Analytical LCMS: (M+H)⁺=525.1.

Example 99

N-(1S)-2,2-Dimethyl-1-[(methylamino)carbonyl]propyl-4-[3-(1-quinolin-6-ylcyclopropyl)[1,2,4]triazolo[4,3-b][1,2,4]triazin-6-yl]benzamide

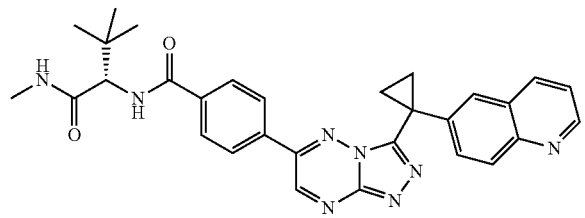

Step 1. tert-butyl (2S)-3,3-dimethyl-2-({4-[3-(1-quinolin-6-ylcyclopropyl) [1,2,4]triazolo[4,3-b][1,2,4]triazin-6-yl]benzoyl}amino)butanoate

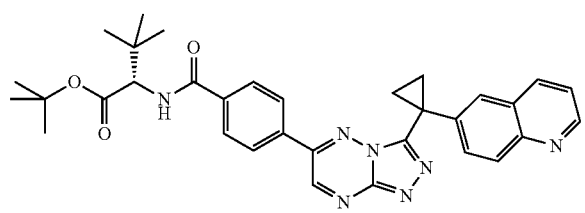

A mixture of 4-[3-(1-quinolin-6-ylcyclopropyl)[1,2,4]triazolo[4,3-b][1,2,4]triazin-6-yl]benzoic acid (40 mg, 0.10 mmol), tert-butyl (2S)-2-amino-3,3-dimethylbutanoate hydrochloride (26 mg, 0.12 mmol), benzotriazol-1-yloxytris(dimethylamino)phosphonium hexafluorophosphate (45.5 mg, 0.103 mmol), and N,N-diisopropylethylamine (60 μL, 0.34 mmol) in methylene chloride (1.5 mL) was stirred at RT overnight. The mixture was diluted with DCM, and washed with saturated NaHCO₃ solution, water and brine, dried over Na₂SO₄, filtered, and concentrated to yield desired product which was directly used in the next step without further purification.

Step 2. (2S)-3,3-dimethyl-2-({4-[3-(1-quinolin-6-ylcyclopropyl)[1,2,4]triazolo[4,3-b][1,2,4]triazin-6-yl]benzoyl}amino)butanoic acid

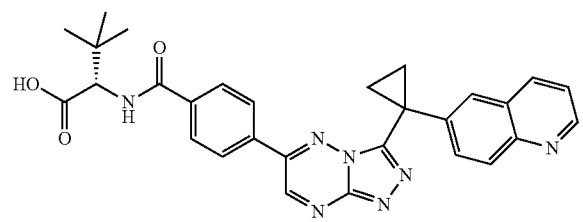

Tert-butyl-(2S)-3,3-dimethyl-2-({4-[3-(1-quino lin-6-ylcyclopropyl)-[1,2,4]triazolo[4,3-b][1,2,4]triazin-6-yl]benzoyl}amino)butanoate was dissolved in methylene chloride (0.7 ml). To the solution was added TFA (0.7 ml). The mixture was stirred for 1.5 h. The volatiles were removed under reduced pressure to yield the desired product. Analytical LCMS: (M+H)$^+$=522.2.

Step 3. N-(1S)-2,2-dimethyl-1-[(methylamino)carbonyl]propyl-4-[3-(1-quinolin-6-ylcyclopropyl)[1,2,4]triazolo[4,3-b][1,2,4]triazin-6-yl]benzamide

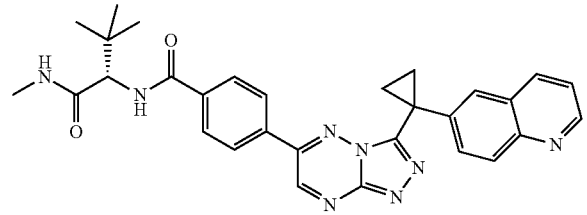

A mixture of (2S)-3,3-dimethyl-2-(4-[3-(1-quinolin-6-ylcyclopropyl)-[1,2,4]triazolo[4,3-b][1,2,4]triazin-6-yl]benzoylamino)butanoic acid (12 mg, 0.023 mmol), 2.00 M of methylamine in tetrahydrofuran (23 μL), benzotriazol-1-yloxytris(dimethylamino)phosphonium hexafluorophosphate (15 mg, 0.034 mmol) and N,N-diisopropylethylamine (16 μL, 0.092 mmol) in methylene chloride (0.5 mL) was stirred at RT for 3 h. The solvent was evaporated. The residue was dissolved in methanol, and purified by RP-HPLC (pH=10) to afford the desired product. Analytical LCMS: (M+H)$^+$=535.2.

Example 100

N-{(1S)-1-[(Dimethylamino)carbonyl]-2,2-dimethylpropyl}-4-[3-(1-quinolin-6-ylcyclopropyl)[1,2,4]triazolo[4,3-b][1,2,4]triazin-6-yl]benzamide

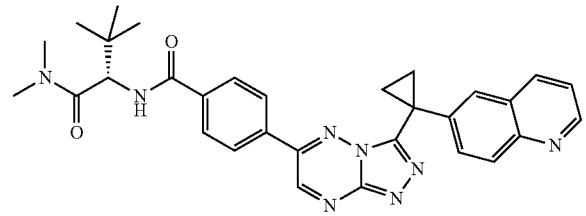

This compound was prepared using procedures analogous to those for Example 99. Analytical LCMS: (M+H)$^+$=549.2.

Example 101

N-[(1S)-1-(Azetidin-1-ylcarbonyl)-2,2-dimethylpropyl]-4-[3-(1-quinolin-6-ylcyclopropyl)[1,2,4]triazolo[4,3-b][1,2,4]triazin-6-yl]benzamide

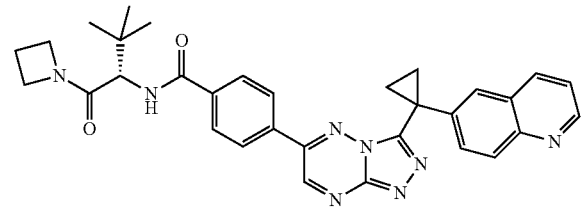

This compound was prepared using procedures analogous to those for Example 99. Analytical LCMS: (M+H)$^+$=561.2.

Example 102

N-[(1S)-2-Amino-1-methyl-2-oxoethyl]-4-[3-(1-quinolin-6-ylcyclopropyl)[1,2,4]triazolo[4,3-b][1,2,4]triazin-6-yl]benzamide

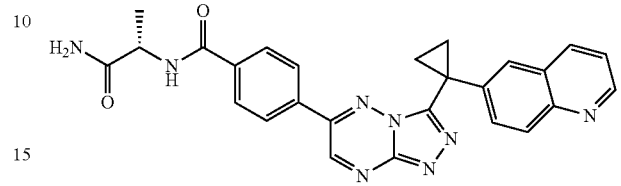

Step 1. benzyl[(1S)-2-amino-1-methyl-2-oxoethyl]carbamate

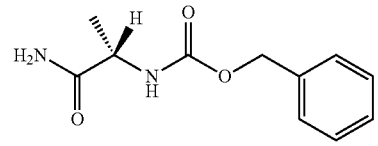

A mixture of (2S)-2-[(benzyloxy)carbonyl]aminopropanoic acid (0.5 g, 0.002 mol), ammonium carbonate (0.43 g, 0.0045 mol), benzotriazol-1-yloxytris(dimethylamino)phosphonium hexafluorophosphate (1.2 g, 0.0027 mol), N,N-diisopropylethylamine (980 μL, 0.0056 mol) in methylene chloride (3 mL) was stirred at RT overnight. The mixture was quenched with saturated NaHCO$_3$ solution, and extracted with DCM. The combined organic layers were washed with brine, dried over Na$_2$SO$_4$, filtered, and concentrated under reduced pressure. The residue was flash chromatographed on a silica gel column to afford the desired product (0.54 g). Analytical LCMS: (M+H)$^+$=223.1.

Step 2. (2S)-2-aminopropanamide

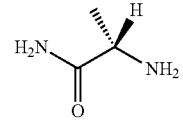

A mixture of benzyl[(1S)-2-amino-1-methyl-2-oxoethyl]carbamate in methanol (10 ml) with 10% Pd on charcoal catalyst (10 mg) was stirred under H$_2$ atmosphere (balloon) for 1 h. The mixture was filtered. The filtrate was concentrated to yield the desired product.

Step 3. N-[(1S)-2-amino-1-methyl-2-oxoethyl]-4-[3-(1-quinolin-6-ylcyclopropyl)[1,2,4]triazolo[4,3-b][1,2,4]triazin-6-yl]benzamide

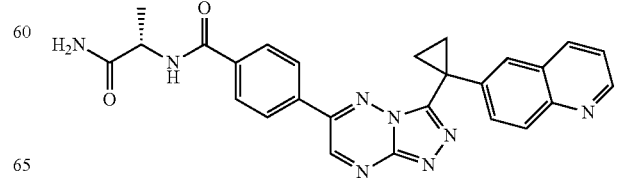

A mixture of 4-[3-(1-quinolin-6-ylcyclopropyl)[1,2,4]triazolo[4,3-b][1,2,4]triazin-6-yl]benzoic acid (10 mg, 0.02 mmol), (2S)-2-aminopropanamide (3.2 mg, 0.037 mmol), benzotriazol-1-yloxytris(dimethylamino)phosphonium hexafluorophosphate (13 mg, 0.029 mmol), and N,N-diisopropylethylamine (13 μL, 0.073 mmol) in methylene chloride (0.5 mL) was stirred at RT overnight. The solvent was evaporated. The residue was dissolved in methanol, and purified by RP-HPLC (pH=10) to afford the desired product. Analytical LCMS: (M+H)+=479.0.

Example 103

N-[(1S)-1-(Aminocarbonyl)-2-methylpropyl]-4-[3-(1-quinolin-6-ylcyclopropyl)[1,2,4]triazolo[4,3-b][1,2,4]triazin-6-yl]benzamide

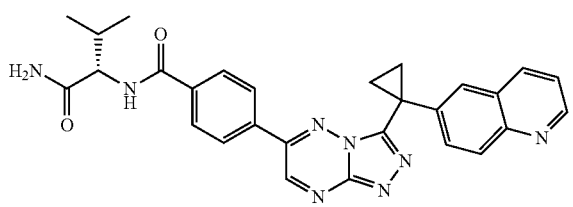

This compound was prepared using procedures analogous to those for Example 102. Analytical LCMS: (M+H)+=507.1.

Example 104

N-Ethyl-2-fluoro-4-[3-(1-quinolin-6-ylcyclopropyl)[1,2,4]triazolo[4,3-b][1,2,4]triazin-6-yl]benzamide

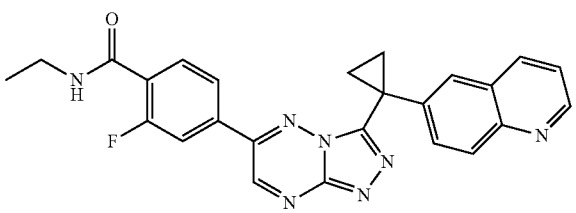

Step 1. methyl 4-acetyl-2-fluorobenzoate

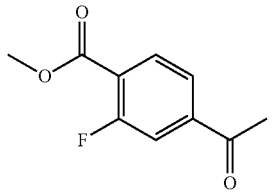

A mixture of methyl 4-bromo-2-fluorobenzoate (7.0 g, 0.030 mol), 1-(ethenyloxy)butane (13 mL, 0.099 mol), palladium acetate (200 mg, 0.0009 mol), 1,3-bis(diphenylphosphino)propane (700 mg, 0.002 mol), and potassium carbonate (4.29 g, 0.0310 mol) in DMF (50 mL) and water (3 mL) was heated at 80° C. with stirring for 24 h. After cooling to RT, to the solution was added 1N HCl solution (31 ml). The mixture was stirred at RT for 1 h, and then extracted with ethyl ether. The combined extracts were washed with brine; dried over Na₂SO₄, filtered concentrated. The residue was flash chromatographed on a silica gel column to give the desired product (1.64 g).

Step 2. methyl 2-fluoro-4-(oxoacetyl)benzoate

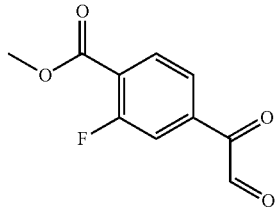

A mixture of methyl 4-acetyl-2-fluorobenzoate (1.6 g, 0.0082 mol), 48% of hydrogen bromide aqueous solution (2.8 mL) in dimethyl sulfoxide (20 mL) was stirred at 60° C. overnight. After cooling, the mixture was poured into ice-water. The product was extracted with ethyl ether. The combined extracts were washed with brine; dried over Na₂SO₄, filtered concentrated to yield 1.60 g of the product which was directly used in the next step without further purification.

Step 3. methyl 4-(diethoxyacetyl)-2-fluorobenzoate

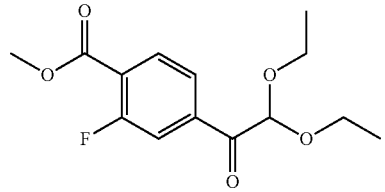

A mixture of methyl 2-fluoro-4-(oxoacetyl)benzoate (1.60 g), ethyl orthoformate (5.2 mL), p-toluenesulfonic acid monohydrate (70 mg) in toluene (20 mL) was heated under reflux for 3 h. After cooling, the mixture was concentrated. The residue was flash chromatographed on a silica gel column to give the desired product (0.63 g).

Step 4. methyl 4-(5-ethoxy-3-thioxo-2,3,4,5-tetrahydro-1,2,4-triazin-6-yl)-2-fluorobenzoate

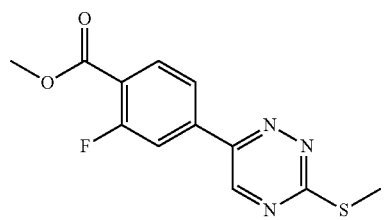

A mixture of methyl 4-(diethoxyacetyl)-2-fluorobenzoate (0.63 g, 0.0022 mol), thiosemicarbazide (0.24 g, 0.0026 mol), and p-toluenesulfonic acid monohydrate (20 mg) in ethanol (6 mL) was heated at 90° C. for 1.5 h. After cooling to RT, to the mixture was added methyl iodide (0.7 mL, 0.01 mol). The mixture was stirred at RT for 1 h. The mixture was concentrated. The residue was dissolved in acetic acid (4 mL), and heated at 60° C. for 2 h. After cooling, the reaction mixture was concentrated. The residue was treated with methanol.

The formed precipitate was collected by filtration, and dried in-vacuo to afford the desired product (180 mg). Analytical LCMS: (M+H)⁺=280.0.

Step 5. methyl 2-fluoro-4-[3-(methylsulfinyl)-1,2,4-triazin-6-yl]benzoate

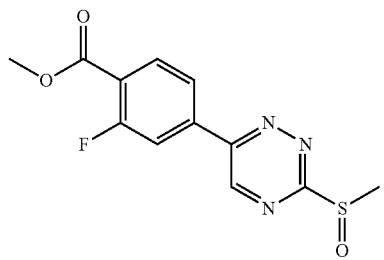

To a cooled (0° C.) solution of methyl 2-fluoro-4-[3-(methylthio)-1,2,4-triazin-6-yl]benzoate (0.180 g, 0.000644 mol) in methylene chloride (10 mL) was added m-chloroperbenzoic acid (0.32 g, 0.0014 mol) in DCM (3 ml) with stirring. The mixture was stirred at 0° C. for 1.5 h, and diluted with DCM. The resulting solution was quenched with saturated $Na_2S_2O_3$ solution. After separation the organic layer was washed with saturated $NaHCO_3$ solution, brine; and dried over $Na_2SO_4$. After filtration the filtrate was concentrated to yield nearly quantitative product which was directly used in the next step without further purification. Analytical LCMS: (M+H)⁺=296.0.

Step 6. methyl 2-fluoro-4-(3-hydrazino-1,2,4-triazin-6-yl)benzoate

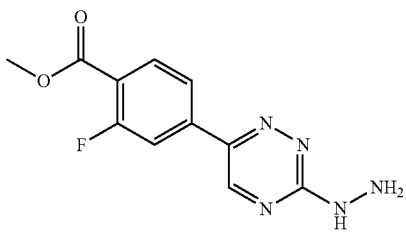

To a suspension of methyl 2-fluoro-4-[3-(methylsulfinyl)-1,2,4-triazin-6-yl]benzoate (0.19 g, 0.00064 mol) in tetrahydrofuran (20 mL) was added hydrazine hydrate (63 µL, 0.0013 mol) slowly. The mixture was stirred at RT for 1.5 h. The mixture was concentrated under reduced pressure to yield the desired product. Analytical LCMS: (M+H)⁺=264.1.

Step 7. methyl 2-fluoro-4-[3-(1-quinolin-6-ylcyclopropyl)[1,2,4]triazolo[4,3-b][1,2,4]triazin-6-yl]benzoate

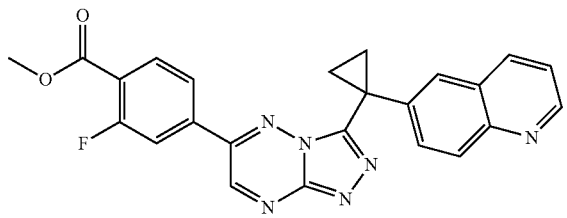

A mixture of methyl 2-fluoro-4-(3-hydrazino-1,2,4-triazin-6-yl)benzoate (0.17 g, 0.64 mmol) and 1-quinolin-6-ylcyclopropanecarbaldehyde (0.13 g, 0.64 mmol) in ethanol (10 mL) and acetic acid (1 mL) was stirred at RT for 2 h. The mixture was concentrated. The residue was dissolved in methylene chloride (5 mL). To the solution was added iodobenzene diacetate (230 mg, 0.71 mmol) with stirring. The mixture was stirred at RT for 2 h then concentrated. The residue was flash chromatographed on a silica gel column to give the desired product (150 mg). Analytical LCMS: (M+H)⁺=441.0.

Step 8. 2-fluoro-4-[3-(1-quinolin-6-ylcyclopropyl)[1,2,4]triazolo[4,3-b][1,2,4]triazin-6-yl]benzoic acid

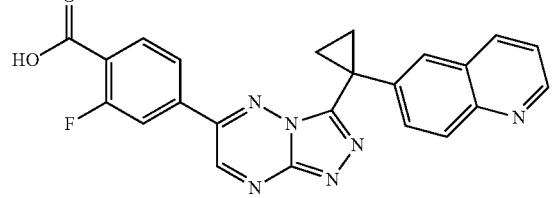

Methyl 2-fluoro-4-[3-(1-quinolin-6-ylcyclopropyl)[1,2,4]triazolo[4,3-b][1,2,4]triazin-6-yl]benzoate (0.15 g, 0.34 mmol) was dissolved in a solution of tetrahydrofuran (3 mL), methanol (1 mL) and water (1 mL) under $N_2$ atmosphere. To the solution was added lithium hydroxide aqueous solution (2.0 M, 0.30 mL) with stirring. The mixture was stirred at RT for 1 h, and acidified with 1.0 M of hydrogen chloride in water (0.68 mL). The organic solvents were removed. The formed precipitate was collected by filtration, and dried in-vacuo to afford the desired product (120 mg). Analytical LCMS: (M+H)⁺=427.0.

Step 9. N-ethyl-2-fluoro-4-[3-(1-quinolin-6-ylcyclopropyl)[1,2,4]triazolo[4,3-b][1,2,4]triazin-6-yl]benzamide

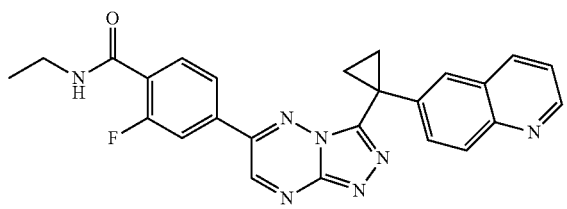

A mixture of 2-fluoro-4-[3-(1-quinolin-6-ylcyclopropyl)[1,2,4]triazolo[4,3-b][1,2,4]triazin-6-yl]benzoic acid (10 mg, 0.02 mmol), 2.0 M of ethylamine in tetrahydrofuran (23 mL), benzotriazol-1-yloxytris(dimethylamino)phosphonium hexafluorophosphate (12 mg, 0.028 mmol), and N,N-diisopropylethylamine (10.0 mL, 0.059 mmol) in methylene chloride (0.5 mL) was stirred at RT for 2 h. The solvent was evaporated. The residue was dissolved in methanol, and purified by RP-HPLC (pH=10) to afford the desired product. Analytical LCMS: (M+H)⁺=454.0. ¹H-NMR (400 MHz, $CD_3OD$): 1.12 (t, 3H), 1.84 (m, 2H), 2.02 (m, 2H), 3.42 (q, 2H), 7.80 (m, 2H), 7.90 (d, 2H), 7.98 (m, 1H), 8.18 (m, 2H), 8.32 (d, 1H), 9.00 (d, 1H), 9.10 (d, 1H), 9.32 (s, 1H).

Example 105

2-Fluoro-N-methyl-4-[3-(1-quinolin-6-ylcyclopropyl)[1,2,4]triazolo[4,3-b][1,2,4]triazin-6-yl]benzamide

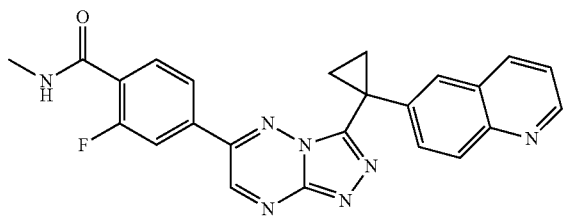

This compound was prepared using procedures analogous to those for Example 104. Analytical LCMS: (M+H)⁺=440.0.
¹H-NMR (400 MHz, CD₃OD): 1.87 (m, 2H), 2.03 (m, 2H), 2.94 (s, 3H), 7.77 (dd, J=11.5, 1.3 Hz, 1H), 7.85 (dd, J=7.9; 7.3 Hz, 1H), 7.91 (dd, J=8.1, 1.5 Hz, 1H), 8.02 (dd, J=8.3 Hz, 5.4; 1H), 8.17 (m, 1H), 8.17 (m, 1H), 8.33 (s, 1H), 9.06 (dd, J=8.1, 1.2 Hz, 1H), 9.13 (dd, J=5.3, 1.4 Hz, 1H), 9.31 (s, 1H).

Example 106

2-Fluoro-N-(trans-4-hydroxycyclohexyl)-4-[3-(1-quinolin-6-ylcyclopropyl)[1,2,4]triazolo[4,3-b][1,2,4]triazin-6-yl]benzamide

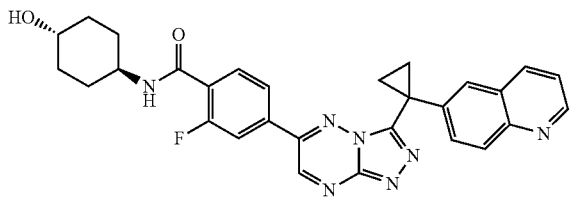

This compound was prepared using procedures analogous to those for Example 104. Analytical LCMS: (M+H)⁺=524.1.

Example 107

2-Fluoro-N-(2-methoxy-1,1-dimethylethyl)-4-[3-(1-quinolin-6-ylcyclopropyl)[1,2,4]triazolo[4,3-b][1,2,4]triazin-6-yl]benzamide

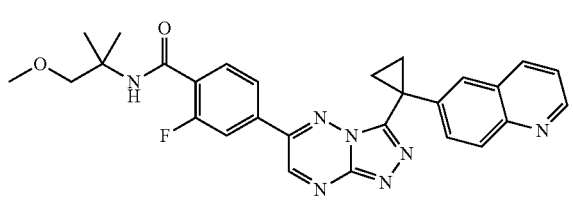

This compound was prepared using procedures analogous to those for Example 104. Analytical LCMS: (M+H)⁺=512.1.

Example 108

N-Cyclopropyl-2-fluoro-4-[3-(1-quinolin-6-ylcyclopropyl) [1,2,4]triazolo[4,3-b][1,2,4]triazin-6-yl]benzamide

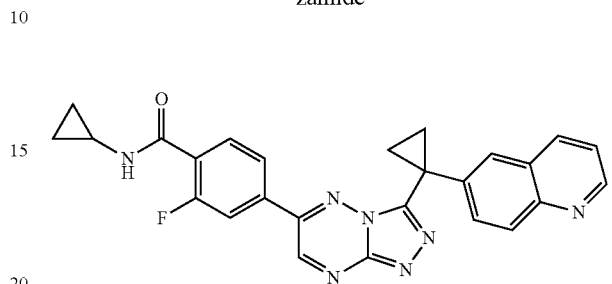

This compound was prepared using procedures analogous to those for Example 104. Analytical LCMS: (M+H)⁺=466.0.

Example 109

2-Fluoro-4-[3-(1-quinolin-6-ylcyclopropyl) [1,2,4]triazolo[4,3-b][1,2,4]triazin-6-yl]benzamide

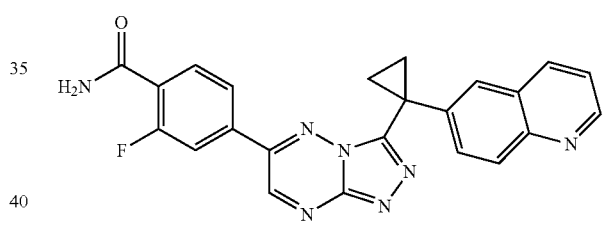

This compound was prepared using procedures analogous to those for Example 104. Analytical LCMS: (M+H)⁺=426.0.
¹H-NMR (400 MHz, CD₃OD): 1.86 (m, 2H), 2.03 (m, 2H), 7.77 (d, 1H), 7.90 (m, 2H), 7.98 (m, 1H), 8.18 (m, 2H), 8.32 (d, 1H), 9.00 (d, 1H), 9.10 (d, 1H), 9.32 (s, 1H).

Example 110

2-Fluoro-N,N-dimethyl-4-[3-(1-quinolin-6-ylcyclopropyl)[1,2,4]triazolo[4,3-b][1,2,4]triazin-6-yl]benzamide

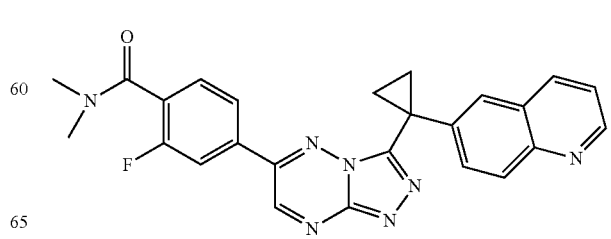

This compound was prepared using procedures analogous to those for Example 104. Analytical LCMS: (M+H)+=454.1.

Example 111

6-(1-{6-[3-Fluoro-4-(pyrrolidin-1-ylcarbonyl)phenyl][1,2,4]triazolo[4,3-b][1,2,4]triazin-3-yl}cyclopropyl)quinoline

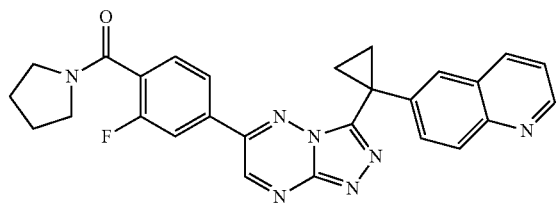

This compound was prepared using procedures analogous to those for Example 104. Analytical LCMS: (M+H)+=480.0.

Example 112

N-Methyl-N-2-[methyl(pyridin-2-yl)amino]ethyl-4-[3-(1-quinolin-6-ylcyclopropyl)[1,2,4]triazolo[4,3-b][1,2,4]triazin-6-yl]benzamide

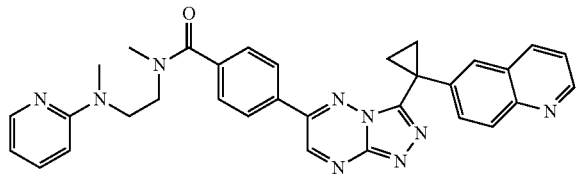

Step 1. tert-butyl 2-[methyl(pyridin-2-yl)-amino]ethylcarbamate

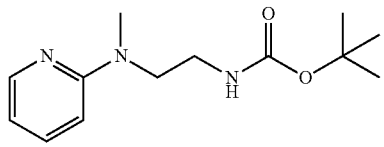

A solution of tert-butyl[2-(methylamino)ethyl]carbamate hydrochloride (0.30 g, 0.0014 mol), 2-chloropyridine (160 mg, 0.0014 mol), and triethylamine (300 μL, 0.0021 mol) in acetonitrile (5 mL) was heated at 90° C. overnight. The mixture was diluted with methanol, and purified by RP-HPLC (pH=10) to afford the desired product. Analytical LCMS: (M+H)+=252.1

Step 2. N-methyl-N-pyridin-2-ylethane-1,2-diamine trifluoroacetate

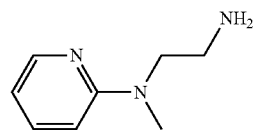

tert-Butyl 2-[methyl(pyridin-2-yl)amino]ethylcarbamate was stirred with DCM (0.5 ml) and TFA (0.5 ml) for 30 min. The volatiles were removed under reduced pressure to yield the product.

Step 3. N-methyl-N-2-[methyl(pyridin-2-yl)-amino]ethyl-4-[3-(1-quinolin-6-ylcyclopropyl)[1,2,4]triazolo[4,3-b][1,2,4]triazin-6-yl]benzamide

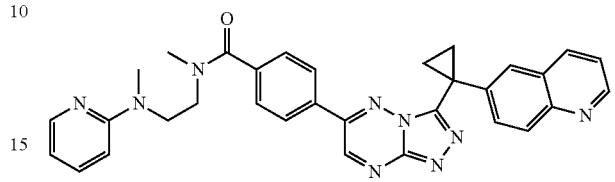

A mixture of 4-[3-(1-quinolin-6-ylcyclopropyl)[1,2,4]triazolo[4,3-b][1,2,4]triazin-6-yl]benzoic acid (10 mg, 0.02 mmol), N-methyl-N-pyridin-2-ylethane-1,2-diamine trifluoroacetate (6.1 mg, 0.037 mmol), benzotriazol-1-yloxytris(dimethylamino)phosphonium hexafluorophosphate (13 mg, 0.029 mmol), and N,N-diisopropylethylamine (13 mL, 0.073 mmol) in methylene chloride (0.5 mL) was stirred at RT for 2 h. The solvent was evaporated. The residue was dissolved in methanol, and purified by RP-HPLC (pH=10) to afford the desired product. Analytical LCMS: (M+H)+=556.2.

Example 113

N-[(1R)-1-(4-Methyl-1,3-thiazol-2-yl)ethyl]-4-[3-(1-quinolin-6-ylcyclopropyl) [1,2,4]triazolo[4,3-b][1,2,4]triazin-6-yl]benzamide

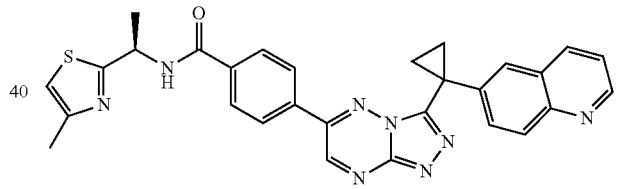

Step 1. tert-butyl[(1R)-2-amino-1-methyl-2-thioxoethyl]carbamate

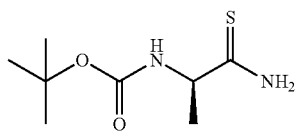

2,4-Bis(4-methoxyphenyl)-2,4-dithioxo-1,3,2,4-dithiadiphosphetane (1.6 g, 0.0038 mol) was added to a solution of tert-butyl[(1R)-2-amino-1-methyl-2-oxoethyl]carbamate (1.45 g, 0.00770 mol) in 1,2-dimethoxyethane (40 mL). The resulting suspension was stirred at RT for 5 h. After removal of solvent the residue was taken up into ethyl acetate. It was washed with 0.1 N NaOH solution, water, brine; dried over Na₂SO₄. After filtration the filtrate was concentrated to yield 1.58 g of the product. (yield: ~100%).

Step 2. tert-butyl[(1R)-1-(4-methyl-1,3-thiazol-2-yl)ethyl]carbamate

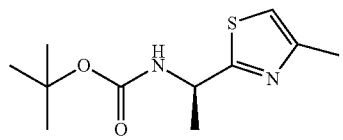

A mixture of tert-butyl[(1R)-2-amino-1-methyl-2-thioxoethyl]carbamate (100 mg, 0.49 mmol) with 3 equivalents of chloroacetone (0.135 g) in ethanol (1 mL) was heated at 80° C. for 2 h. After cooling, the solution was concentrated. The residue was dissolved in DCM (1 ml). To the solution was added TFA (1 mL). The mixture was stirred at RT for 30 min. The volatiles were removed under reduced pressure to yield desired product.

Step 3. N-[(1R)-1-(4-methyl-1,3-thiazol-2-yl)ethyl]-4-[3-(1-quinolin-6-ylcyclopropyl)[1,2,4]triazolo[4,3-b][1,2,4]triazin-6-yl]benzamide

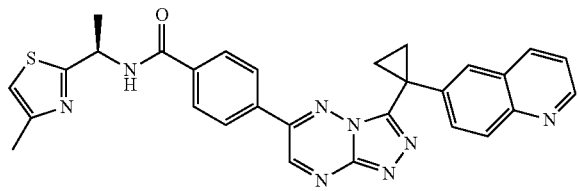

A mixture of 4-[3-(1-quinolin-6-ylcyclopropyl)[1,2,4]triazolo[4,3-b][1,2,4]triazin-6-yl]benzoic acid (10 mg, 0.02 mmol), (1R)-1-(4-methyl-1,3-thiazol-2-yl)ethanamine bis(trifluoroacetate) (14 mg, 0.037 mmol), benzotriazol-1-yloxytris(dimethylamino)phosphonium hexafluorophosphate (14 mg, 0.032 mmol), and N,N-diisopropylethylamine (21 µL, 0.12 mmol) in methylene chloride (0.5 mL) was stirred at RT for 2 h. The solvent was evaporated. The residue was dissolved in methanol, and purified by RP-HPLC (pH=10) to afford the desired product. Analytical LCMS: $(M+H)^+=533.1$.

Example A

In Vitro c-Met Kinase Enzyme Assays

Compounds were screened in vitro for their ability to inhibit c-Met kinase activity. The $IC_{50}$ values of compounds for the inhibition of c-Met kinase were determined as described in the literature with some modifications (Wang, X. et al, Mol. Cancer. Ther. 2003, 2(11):1085-1092; Calic, M. et al., Croatica Chemical ACTA. 2005, 78(3):367-374). Briefly, histidine-tagged c-Met catalytic domain fusion protein (Invitrogen, #PV3143) was used for the assay. $IC_{50}$ measurements were based on the degree of phosphorylation of poly Glu-Tyr (Sigma-Aldrich, #PO$_{275}$) that was coated (0.01 mg/per well) on 96-well microplates (R&D systems, #DY990). The reaction was carried out in a 50 µL solution containing 50 mM HEPES (pH 7.5), 10 mM $MnCl_2$, 10 mM $MgCl_2$, 0.5 mM DTT, 100 µM $Na_3VO_4$, 5 µM ATP (Cell Signaling Technology, #9804) and serial dilutions of individual compounds. The reaction lasted for 25 minutes at 30° C. After the reaction was completed, the contents of the plates was discarded. Plates were then washed with TBS-T (250 µL/well, 5×) and then blocked with TBS-T containing 1% BSA for 2 hours. The contents of the plates was discarded, and 100 µL (per well) of peroxidase-labeled anti-phospho-tyrosine antibody (Sigma, #A5964) diluted (1:60,000) in 1% BSA containing TBS-T were then added and incubated for 1 hour. Plates were washed with TBS-T (250 µL/well, 5×) and followed by the color reaction using 100 µL (1:1 mixture) of $H_2O_2$ and tetramethylbenzidine (R&D Systems, #DY999). The reaction was stopped in minutes with 100 µL of 2 N $H_2SO_4$. The optical density was measured immediately using a microplate reader at 450 nm with wavelength correction at 540 nm. $IC_{50}$ values were calculated with the GraphPad Prism software. The linear range (i.e., the time period over which the rate remained equivalent to the initial rate) was determined for the kinase and $IC_{50}$ determinations were performed within this range. Compounds having an $IC_{50}$ of 20 µM or less were considered active. The $IC_{50}$ value for the compound of Example 26 according to this assay was found to be 12.9 nM. The other Example compounds were also found to be active.

Wang, X., et al. Potent and selective inhibitors of the Met [hepatocyte growth factor/scatter factor (HGF/SF) receptor] tyrosine kinase block HGF/SF-induced tumor cell growth and invasion. Mol. Cancer. Ther. 2003, 2(11):1085-1092.

Calic, M., et al. Flavonoids as inhibitors of Lck and Fyn kinases. Croatica Chemica ACTA. 2005, 78(3):367-374.

Example B

Cell Proliferation/Survival Assays

Cell lines representing various human cancers (SNU-1 and SUN-5 gastric, A549 and NCI-H441 lung, U-87 glioblastoma, HT-29 colon, 786-0 kidney, PC-3 pancreatic) were obtained from American Type Culture Collection and routinely maintained in culture media and conditions recommended by ATCC. Optimal cell density used in proliferation/survival assay was predetermined for individual cell lines. Compounds were screened for their ability to inhibit cell proliferation/survival, and $IC_{50}$ values were determined Below are the sample protocols for SNU-5 and SNU-1 cell proliferation/survival assays. SNU-5 and SNU-1 cells were seeded into 96 well cell culture plates at 4000 cells/well and 2000 cells/well respectively in appropriate media containing 2% FBS and supplemented with serial dilutions of individual compounds in a final volume of 100 µL/well. After 72 hour incubation, 24 µL of CellTiter 96® AQueous One Solution reagent (Promega, #G3581) were added to each well (final concentration=333 µg/mL), and the plates were incubated for 2 more hours in a 37° C. incubator. The optical density was measured in the linear range using a microplate reader at 490 nm with wavelength correction at 650 nm. $IC_{50}$ values were calculated with the GraphPad Prism software. For proliferation assays using A549, NCI-H441, U-87, HT-29, 786-0 and PC-3 cells, the cells were first starved for 48 hours in low serum condition (0.1-0.5% FBS in appropriate culture media), then treated with different concentrations of compounds for 2 hours. After the cells were treated with HGF (50 ng/mL) (R&D, #294-HGN) for 24 hours, CellTiter 96® AQueous One Solution reagent was added and plates were incubated for 2 hours. The results were recorded with a plate reader. Compounds having an $IC_{50}$ of 20 µM or less were considered active.

Example C

Cell-Based c-Met Phosphorylation Assays

The inhibitory effect of compounds on c-Met phosphorylation in relevant cell lines (SNU-5 gastric, A549 and NCI-H441 lung, U-87 glioblastoma, HT-29 colon, 786-0 kidney and PC-3 pancreatic cancer cell lines and HUVEC cell line) was assessed using immunoblotting analysis and ELISA-based c-Met phosphorylation assays. Cells were grown in appropriate culture media and treated with various concentrations of individual compounds. For SNU-5, HT-29, 786-0 cells, cells were grown in appropriated media supplemented with 0.2% or 2% FBS and treated with compounds for 3-4 hours. Whole cell protein extracts were prepared using reagents and a protocol (#FNN0011) obtained from Biosource International with slight modifications. Briefly, protein extracts were made by incubation in lysis buffer with protease and phosphatase inhibitors [50 mM HEPES (pH 7.5), 100 mM NaCl, 1.5 mM $MgCl_2$, 10% Glycerol, 1% Triton X-100, 1 mM sodium orthovanadate, 1 mM sodium fluoride, aprotinin (2 μg/mL), leupeptin (2 μg/mL), pepstatin A (2 μg/mL), and phenylmethylsulfonyl fluoride (1 mM)] at 4° C. Protein extracts were cleared of cellular debris by centrifugation at 14,000×g for 20 minutes. For A549, H441, U-87 and PC-3 cells, cells were serum (0.2% FBS) starved for at least 24 hours, then pretreated with various concentrations of compounds for 1 hour. Whole cell extracts were prepared after the cells were treated with HGF (50 ng/mL) for 10 minutes.

Immunoblotting Analysis

Relevant antibodies were obtained from commercial sources: rabbit polyclonal antibodies included anti-human c-Met (Santa Cruz Biotechnology, #sc-161) and anti-phosphorylated-c-Met (Biosource International, pY1230/4/5 and pY1003). For immunoblotting, 10-20 μg of protein extracts from individual treatment conditions were resolved by electrophoresis on 10% SDS-PAGE gel, and electrotransferred to a nitrocellulose (or PVDF) membrane. The membrane was blocked in PBS containing 3% milk and 0.1% Tween-20 for 1 hour, and then incubated with primary anti-c-Met antibodies in blocking solution for 1 hour. After 3 washes, the membrane was incubated with appropriate horseradish-conjugated secondary antibodies for 1 hour. After final wash, the blot was incubated with chemiluminescence detection reagent for 5 minutes and exposed to X-ray film. The images were scanned, quantified and corrected with total c-Met, and $IC_{50}$ values were calculated. Compounds having an $IC_{50}$ of 20 μM or less were considered active.

ELISA

Cell protein extracts were analyzed using a human phospho-c-Met ELISA kit according to the manufacturer's instructions (R&D Systems, #DYC2480). Optimal amounts of protein extracts were predetermined for individual cell lines. Briefly, for the assay, appropriate amounts of protein extracts were captured with a capture anti-human c-Met antibody for 2 hours in a 96 well microplate. After washes, a detection antibody (HRP-conjugated anti-phospho-tyrosine antibody) was added and incubated for 2 hours. After additional washes, 100 μL of substrate solution (1:1 mixture of $H_2O_2$ and tetramethylbenzidine) were added into each well and the reaction was stopped with 2 N $H_2SO_4$ within an appropriate amount of time during color development. The optical density was measured in the linear range using a microplate reader at 450 nm with wavelength correction at 540 nm. $IC_{50}$ values were calculated with the GraphPad Prism software. Compounds having an $IC_{50}$ of 20 μM or less were considered active.

Example D

Assays to Assess Inhibition of c-Met Phosphorylation In Vivo

Mice

Female Balb/c nu/nu mice, 6-8 weeks old, were acquired from Charles River Laboratories (Wilmington, Mass.) and were maintained according to NIH standards. Animal studies were performed under Animal Welfare Regulation Guidelines in a facility accredited by the Association for the Assessment and Accreditation of Laboratory Animal Care (AAALAC).

Generation of Tumors

S114 cells, murine NIH 3T3 cells engineered to coexpress the human c-Met receptor and human hepatocyte growth factor (HGF) which were licensed from the NIH, were grown in culture in DMEM supplemented with 10% FBS. Cells were kept at 37° C. in a humidified incubator supplied with 5% $CO_2$. Prior to inoculation, logarithmically growing cells were washed, counted and resuspended in PBS. Injections of $5\times10^6$ cells in 0.1 mL were made into the right flank of Balb/c nu/nu mice. After 6-9 days, when tumor volumes reached an average of 125-400 $mm^3$, depending on the experiment, mice were randomized for testing in vivo compound potency.

Treatment and Sample Harvest

Tumor bearing mice were administered a single dose of 5-50 mg/kg compound orally in 5% DMAC in 0.5% methylcellulose. At various times between 1-8 hours post dose administration, mice were humanely euthanized using 100% $CO_2$ and tumors were excised, placed directly into lysis buffer with protease and phosphatase inhibitors [50 mM HEPES (pH 7.5), 100 mM NaCl, 1.5 mM $MgCl_2$, 10% Glycerol, 1% Triton X-100, 1 mM sodium orthovanadate, 1 mM sodium fluoride, aprotinin (2 μg/mL), leupeptin (2 μg/mL), pepstatin A (2 μg/mL), and phenylmethylsulfonyl fluoride (1 mM)] at 4° C. and processed for determination of c-Met phosphorylation by ELISA (described in Example C above). Terminal bloods were harvested for the determination of circulating compound levels in plasma. Data were graphed and analyzed using GraphPad Prism 3.0.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating bladder cancer, cervical cancer, cholangiocarcinoma cancer, colorectal cancer, esophageal cancer, head and neck cancer, liver cancer, nasopharyngeal cancer, thyroid cancer, osteosarcoma, synovial sarcoma, MFH/fibrosarcoma, leiomyosarcoma, Kaposi's sarcoma, multiple myeloma, lymphoma, adult T cell leukemia, acute myelogenous leukemia, chronic myeloid leukemia, astrocytoma, or Wilm's tumor in a patient, wherein said cancer is associated with dysregulation of the HGF/c-Met kinase signaling pathway, comprising administering to said patient a therapeutically effective amount of a compound of Formula I:

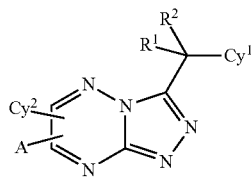

or pharmaceutically acceptable salt thereof, wherein:

$Cy^1$ is aryl, heteroaryl, cycloalkyl, or heterocycloalkyl, each optionally substituted by 1, 2, 3, 4, or 5 —W—X—Y—Z;

$Cy^2$ is aryl, heteroaryl, cycloalkyl, or heterocycloalkyl, each optionally substituted by 1, 2, 3, 4, or 5 —W'—X'—Y'—Z';

A is H, halo, $C_{1-6}$ alkyl, $C_{2-6}$ alkenyl, $C_{2-6}$ alkynyl, $C_{1-6}$ haloalkyl, CN, $NO_2$, $OR^A$, $SR^A$, $C(O)R^B$, $C(O)NR^CR^B$, $C(O)OR^A$, $OC(O)R^B$, $OC(O)NR^CR^D$, $NR^CR^D$, $NR^CC(O)R^B$, $NR^CC(O)NR^CR^D$, $NR^CC(O)OR^A$, $S(O)R^B$, $S(O)NR^CR^D$, $S(O)_2R^B$, $NR^CS(O)_2R^B$, or $S(O)_2NR^CR^D$;

$R^1$ and $R^2$ together with the carbon atom to which they are attached form a 3- to 7-membered cycloalkyl group or 3- to 7-membered heterocycloalkyl group, each optionally substituted by 1, 2, 3, 4, or 5 substituents independently selected from Q, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$, wherein said $C_{1-6}$ alkyl, $C_{2-6}$ alkenyl, and $C_{2-6}$ alkynyl is optionally substituted with 1, 2, or 3 substituents selected from Q, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$;

Q is aryl, heteroaryl, cycloalkyl, or heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

W and W' are independently absent or independently selected from $C_{1-6}$ alkylene, $C_{2-6}$ alkenylene, $C_{2-6}$ alkynylene, O, S, $NR^h$, CO, COO, $CONR^h$, SO, $SO_2$, $SONR^h$ and $NR^hCONR^i$, wherein each of the $C_{1-6}$ alkylene, $C_{2-6}$ alkenylene, and $C_{2-6}$ alkynylene is optionally substituted by 1, 2 or 3 substituents independently selected from halo, $C_{1-6}$ alkyl, $C_{1-6}$ haloalkyl, OH, $C_{1-6}$ alkoxy, $C_{1-6}$ haloalkoxy, amino, $C_{1-6}$ alkylamino, and $C_{2-8}$ dialkylamino;

X and X' are independently absent or independently selected from $C_{1-6}$ alkylene, $C_{2-6}$ alkenylene, $C_{2-6}$ alkynylene, arylene, cycloalkylene, heteroarylene, and heterocycloalkylene, wherein each of the $C_{1-6}$ alkylene, $C_{2-6}$ alkenylene, $C_{2-6}$ alkynylene, arylene, cycloalkylene, heteroarylene, and heterocycloalkylene is optionally substituted by 1, 2 or 3 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^i$, $C(O)NR^hR^i$, amino, $C_{1-6}$ alkylamino, and $C_{2-8}$ dialkylamino;

Y and Y' are independently absent or independently selected from $C_{1-6}$ alkylene, $C_{2-6}$ alkenylene, $C_{2-6}$ alkynylene, O, S, $NR^h$, CO, COO, $CONR^h$, SO, $SO_2$, $SONR^h$, and $NR^hCONR^i$, wherein each of the $C_{1-6}$ alkylene, $C_{2-6}$ alkenylene, and $C_{2-6}$ alkynylene is optionally substituted by 1, 2 or 3 substituents independently selected from halo, $C_{1-6}$ alkyl, $C_{1-6}$ haloalkyl, OH, $C_{1-6}$ alkoxy, $C_{1-6}$ haloalkoxy, amino, $C_{1-6}$ alkylamino, and $C_{2-8}$ dialkylamino;

Z and Z' are independently selected from H, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $S(O)R^{b2}$, $S(O)NR^{c2}R^{d2}$, $S(O)_2R^{b2}$, $NR^{c2}S(O)_2R^{b2}$, $S(O)_2NR^{c2}R^{d2}$, aryl, cycloalkyl, heteroaryl, and heterocycloalkyl, wherein said $C_{1-6}$ alkyl, $C_{2-6}$ alkenyl, $C_{2-6}$ alkynyl, aryl, cycloalkyl, heteroaryl, and heterocycloalkyl are optionally substituted by 1, 2, 3, 4 or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

wherein two adjacent —W—X—Y—Z, together with the atoms to which they are attached, optionally form a fused 4-, 5-, 6-, or 7-membered cycloalkyl ring or a fused 4-, 5-, 6-, or 7-membered heterocycloalkyl ring, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $S(O)R^{b2}$, $S(O)NR^{c2}R^{d2}$, $S(O)_2R^{b2}$, $NR^{c2}S(O)_2R^{b2}$, $S(O)_2NR^{c2}R^{d2}$, aryl, cycloalkyl, heteroaryl, and heterocycloalkyl;

wherein two adjacent —W'—X'—Y'—Z', together with the atoms to which they are attached, optionally form a fused 4-, 5-, 6-, or 7-membered cycloalkyl ring or a fused 4-, 5-, 6-, or 7-membered heterocycloalkyl ring, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $S(O)R^{b2}$, $S(O)NR^{c2}R^{d2}$, $S(O)_2R^{b2}$, $NR^{c2}S(O)_2R^{b2}$, $S(O)_2NR^{c2}R^{d2}$, aryl, cycloalkyl, heteroaryl, and heterocycloalkyl;

$R^A$ is H, $C_{1-4}$ alkyl, $C_{2-4}$ alkenyl, or $C_{2-4}$ alkynyl, wherein said $C_{1-4}$ alkyl, $C_{2-4}$ alkenyl, or $C_{2-4}$ alkynyl, is optionally substituted with 1, 2, or 3 substituents independently selected from OH, CN, amino, halo, and $C_{1-4}$ alkyl;

$R^B$ is H, $C_{1-4}$ alkyl, $C_{2-4}$ alkenyl, or $C_{2-4}$ alkynyl, wherein said $C_{1-4}$ alkyl, $C_{2-4}$ alkenyl, or $C_{2-4}$ alkynyl, is optionally substituted with 1, 2, or 3 substituents independently selected from OH, CN, amino, halo, and $C_{1-4}$ alkyl;

$R^C$ and $R^D$ are independently selected from H, $C_{1-4}$ alkyl, $C_{2-4}$ alkenyl, or $C_{2-4}$ alkynyl, wherein said $C_{1-4}$ alkyl, $C_{2-4}$ alkenyl, or $C_{2-4}$ alkynyl, is optionally substituted with 1, 2, or 3 substituents independently selected from OH, CN, amino, halo, and $C_{1-4}$ alkyl;

or $R^C$ and $R^D$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, and $C_{1-4}$ alkyl;

$R^a$, $R^{a1}$, $R^{a2}$, and $R^{a3}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^b$, $R^{b1}$, $R^{b2}$, and $R^{b3}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^c$ and $R^d$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^c$ and $R^d$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{c1}$ and $R^{d1}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c1}$ and $R^{d1}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{c2}$ and $R^{d2}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl are each optionally substituted with 1, 2, or 3 substituents independently selected from OH, CN, amino, halo, $C_{1-6}$ alkyl, $C_{1-6}$ alkoxy, $C_{1-6}$ haloalkyl, $C_{1-6}$ haloalkoxy, hydroxyalkyl, cyanoalkyl, aryl, heteroaryl, $C(O)OR^{a3}$, $C(O)R^{b3}$, $S(O)_2R^{b3}$, alkoxyalkyl, and alkoxyalkoxy;

or $R^{c2}$ and $R^{d2}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, $C_{1-6}$ haloalkoxy, hydroxyalkyl, cyanoalkyl, aryl, heteroaryl, $C(O)OR^{a3}$, $C(O)R^{b3}$, $S(O)_2R^{b3}$, alkoxyalkyl, and alkoxyalkoxy;

$R^e$ is H, $C_{1-6}$ alkyl, $C_{1-6}$ haloalkyl, $C_{2-6}$ alkenyl, $(C_{1-6}$ alkoxy)-$C_{1-6}$ alkyl, $C_{2-6}$ alkynyl, aryl, cycloalkyl, heteroaryl, heterocycloalkyl, arylalkyl, cycloalkylalkyl, heteroarylalkyl, or heterocycloalkylalkyl;

$R^f$ is H, $C_{1-6}$ alkyl, $C_{1-6}$ haloalkyl, $C_{2-6}$ alkenyl, $C_{2-6}$ alkynyl, aryl, cycloalkyl, heteroaryl, or heterocycloalkyl;

$R^g$, $R^{g1}$, and $R^{g2}$ are independently selected from H, CN, and $NO_2$;

$R^h$ and $R^i$ are independently selected from H and $C_{1-6}$ alkyl; and $R^j$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl.

2. The method of claim 1 wherein $Cy^1$ is aryl or heteroaryl, each optionally substituted by 1, 2, 3, 4, or 5 —W—X—Y—Z.

3. The method of claim 1 wherein $Cy^1$ is aryl or heteroaryl, each optionally substituted by 1, 2, 3, 4, or 5 —Z.

4. The method of claim 1 wherein $Cy^1$ is aryl or heteroaryl, each optionally substituted by 1, 2, or 3 substituents independently selected from halo, $C_{1-4}$ alkyl, $C_{1-4}$ haloalkyl, OH, and $C_{1-4}$ alkoxy.

5. The method of claim 1 wherein $Cy^1$ is phenyl or quinolinyl, each optionally substituted by 1, 2, 3, 4, or 5 —W—X—Y—Z.

6. The method of claim 1 wherein $Cy^2$ is aryl or heteroaryl, each optionally substituted by 1, 2, 3, 4, or 5 —W'—X'—Y'—Z'.

7. The method of claim 1 wherein $Cy^2$ is phenyl optionally substituted by 1, 2, 3, 4, or 5 W'—X'—Y'—Z'.

8. The method of claim 1 wherein $Cy^2$ is phenyl optionally substituted by 1, 2, 3, 4, or 5 —Z'.

9. The method of claim 1 wherein A is H, halo, $C_{1-6}$ alkyl, $C_{1-6}$ haloalkyl, CN, $NO_2$, $OR^A$, or $NR^CR^D$.

10. The method of claim 1 wherein A is H or $NR^CR^D$.

11. The method of claim 1 wherein $R^1$ and $R^2$ together with the carbon atom to which they are attached form a 3- to 7-membered cycloalkyl group optionally substituted by 1, 2, 3, 4, or 5 substituents independently selected from Q, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$, wherein said $C_{1-6}$ alkyl, $C_{2-6}$ alkenyl, and $C_{2-6}$ alkynyl is optionally substituted with 1, 2, or 3 substituents selected from Q, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$.

12. The method of claim 1 wherein $R^1$ and $R^2$ together with the carbon atom to which they are attached form a cyclopropyl group optionally substituted by 1, 2, 3, 4, or 5 substituents independently selected from Q, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$, wherein said $C_{1-6}$ alkyl, $C_{2-6}$ alkenyl, and $C_{2-6}$ alkynyl is optionally substituted with 1, 2, or 3 substituents selected from Q, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$.

13. The method of claim 1 wherein $R^1$ and $R^2$ together with the carbon atom to which they are attached form a 3- to 7-membered cycloalkyl group.

14. The method of claim 1 wherein $R^1$ and $R^2$ together with the carbon atom to which they are attached form a cyclopropyl group.

15. The method of claim 1 having Formula II:

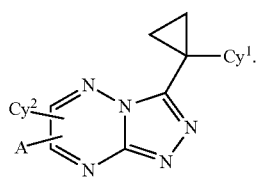

II

16. The method of claim 1 wherein said compound has Formula IIIa or IIIb:

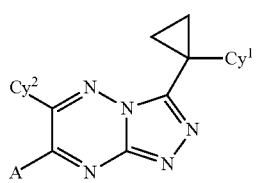

IIIa

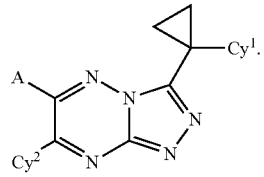

IIIb

17. The compound of claim 1 selected from:
3-[1-(4-Methoxyphenyl)cyclopropyl]-6-phenyl[1,2,4]triazolo[4,3-b][1,2,4]triazine;
3-[1-(4-Methoxyphenyl)cyclopropyl]-7-phenyl[1,2,4]triazolo[4,3-b][1,2,4]triazine;
4-[1-(6-Phenyl[1,2,4]triazolo[4,3-b][1,2,4]triazin-3-yl)cyclopropyl]phenol;
4-[1-(7-Phenyl[1,2,4]triazolo[4,3-b][1,2,4]triazin-3-yl)cyclopropyl]phenol;
6-(4-Fluorophenyl)-3-[1-(4-methoxyphenyl)cyclopropyl][1,2,4]triazolo[4,3-b][1,2,4]triazine;
7-(4-Fluorophenyl)-3-[1-(4-methoxyphenyl)cyclopropyl][1,2,4]triazolo[4,3-b][1,2,4]triazine;
3-[1-(4-Methoxyphenyl)cyclopropyl]-6-(4-morpholin-4-ylphenyl)[1,2,4]triazolo[4,3-b][1,2,4]triazine;
3-[1-(4-Methoxyphenyl)cyclopropyl]-7-(4-morpholin-4-ylphenyl)[1,2,4]triazolo[4,3-b][1,2,4]triazine;
6-(4-Chlorophenyl)-3-[1-(4-methoxyphenyl)cyclopropyl][1,2,4]triazolo[4,3-b][1,2,4]triazine;
7-(4-Chlorophenyl)-3-[1-(4-methoxyphenyl)cyclopropyl][1,2,4]triazolo[4,3-b][1,2,4]triazine;
4-3-[1-(4-Methoxyphenyl)cyclopropyl][1,2,4]triazolo[4,3-b][1,2,4]triazin-6-ylphenol;
4-{3-[1-(4-Methoxyphenyl)cyclopropyl][1,2,4]triazolo[4,3-b][1,2,4]triazin-7-yl}phenol;
4-3-[1-(4-Methoxyphenyl)cyclopropyl][1,2,4]triazolo[4,3-b][1,2,4]triazin-6-ylbenzonitrile;
4-{3-[1-(4-Methoxyphenyl)cyclopropyl][1,2,4]triazolo[4,3-b][1,2,4]triazin-7-yl}benzonitrile;
N-(4-3-[1-(4-Methoxyphenyl)cyclopropyl][1,2,4]triazolo[4,3-b][1,2,4]triazin-6-ylphenyl)acetamide;
N-(4-{3-[1-(4-Methoxyphenyl)cyclopropyl][1,2,4]triazolo[4,3-b][1,2,4]triazin-7-yl}phenyl)acetamide;
6-(4-Methoxyphenyl)-3-[1-(4-methoxyphenyl)cyclopropyl][1,2,4]triazolo[4,3-b][1,2,4]triazine;
7-(4-Methoxyphenyl)-3-[1-(4-methoxyphenyl)cyclopropyl][1,2,4]triazolo[4,3-b][1,2,4]triazine;
6-(2,4-Difluorophenyl)-3-[1-(4-methoxyphenyl)cyclopropyl][1,2,4]triazolo[4,3-b][1,2,4]triazine;
7-(2,4-Difluorophenyl)-3-[1-(4-methoxyphenyl)cyclopropyl][1,2,4]triazolo[4,3-b][1,2,4]triazine;
6-(3,4-Dichlorophenyl)-3-[1-(4-methoxyphenyl)cyclopropyl][1,2,4]triazolo[4,3-b][1,2,4]triazine;
7-(3,4-Dichlorophenyl)-3-[1-(4-methoxyphenyl)cyclopropyl][1,2,4]triazolo[4,3-b][1,2,4]triazine;
6-(3,4-Difluorophenyl)-3-[1-(4-methoxyphenyl)cyclopropyl][1,2,4]triazolo[4,3-b][1,2,4]triazine;
7-(3,4-Difluorophenyl)-3-[1-(4-methoxyphenyl)cyclopropyl][1,2,4]triazolo[4,3-b][1,2,4]triazine;
6-(3-Methoxyphenyl)-3-[1-(4-methoxyphenyl)cyclopropyl][1,2,4]triazolo[4,3-b][1,2,4]triazine;
7-(3-Methoxyphenyl)-3-[1-(4-methoxyphenyl)cyclopropyl][1,2,4]triazolo[4,3-b][1,2,4]triazine;
6-(3-Bromophenyl)-3-[1-(4-methoxyphenyl)cyclopropyl][1,2,4]triazolo[4,3-b][1,2,4]triazine;
7-(3-Bromophenyl)-3-[1-(4-methoxyphenyl)cyclopropyl][1,2,4]triazolo[4,3-b][1,2,4]triazine;

6-(5-Bromo-2-thienyl)-3-[1-(4-methoxyphenyl)cyclopropyl][1,2,4]triazolo[4,3-b][1,2,4]triazine;
7-(5-Bromo-2-thienyl)-3-[1-(4-methoxyphenyl)cyclopropyl][1,2,4]triazolo[4,3-b][1,2,4]triazine;
3-[1-(4-Methoxyphenyl)cyclopropyl]-6-(4-nitrophenyl)[1,2,4]triazolo[4,3-b][1,2,4]triazine;
3-[1-(4-Methoxyphenyl)cyclopropyl]-7-(4-nitrophenyl)[1,2,4]triazolo[4,3-b][1,2,4]triazine;
6-(4-Bromophenyl)-3-[1-(4-methoxyphenyl)cyclopropyl][1,2,4]triazolo[4,3-b][1,2,4]triazine;
7-(4-Bromophenyl)-3-[1-(4-methoxyphenyl)cyclopropyl][1,2,4]triazolo[4,3-b][1,2,4]triazine;
4-3-[1-(4-Methoxyphenyl)cyclopropyl][1,2,4]triazolo[4,3-b][1,2,4]triazin-6-ylaniline;
4-{3-[1-(4-Methoxyphenyl)cyclopropyl][1,2,4]triazolo[4,3-b][1,2,4]triazin-7-yl}aniline;
3-[1-(4-Methoxyphenyl)cyclopropyl]-6-[3-(1-methyl-1H-pyrazol-4-yl)phenyl][1,2,4]triazolo[4,3-b][1,2,4]triazine;
3-[1-(4-Methoxyphenyl)cyclopropyl]-7-[3-(1-methyl-1H-pyrazol-4-yl)phenyl][1,2,4]triazolo[4,3-b][1,2,4]triazine;
3-[1-(4-Methoxyphenyl)cyclopropyl]-6-[3-(1H-pyrazol-4-yl)phenyl][1,2,4]triazolo[4,3-b][1,2,4]triazine;
3-[1-(4-Methoxyphenyl)cyclopropyl]-7-[3-(1H-pyrazol-4-yl)phenyl][1,2,4]triazolo[4,3-b][1,2,4]triazine;
tert-Butyl (3'-3-[1-(4-methoxyphenyl)cyclopropyl][1,2,4]triazolo[4,3-b][1,2,4]triazin-6-ylbiphenyl-4-yl)carbamate;
tert-Butyl (3'-{3-[1-(4-methoxyphenyl)cyclopropyl][1,2,4]triazolo[4,3-b][1,2,4]triazin-7-yl}biphenyl-4-yl)carbamate;
3-[1-(4-Methoxyphenyl)cyclopropyl]-6-[4-(1H-pyrazol-4-yl)phenyl][1,2,4]triazolo[4,3-b][1,2,4]triazine;
3-[1-(4-Methoxyphenyl)cyclopropyl]-6-[4-(1-methyl-1H-pyrazol-4-yl)phenyl][1,2,4]triazolo[4,3-b][1,2,4]triazine;
3-[1-(4-Bromophenyl)cyclopropyl]-6-phenyl[1,2,4]triazolo[4,3-b][1,2,4]triazine;
3-[1-(3-Bromophenyl)cyclopropyl]-6-phenyl[1,2,4]triazolo[4,3-b][1,2,4]triazine;
3-[1-(4-Methoxyphenyl)cyclopropyl]-6-phenyl[1,2,4]triazolo[4,3-b][1,2,4]triazine;
6-[1-(6-Phenyl[1,2,4]triazolo[4,3-b][1,2,4]triazin-3-yl)cyclopropyl]quinoline;
3-[1-(4-Chlorophenyl)cyclopropyl]-6-(4-fluorophenyl)[1,2,4]triazolo[4,3-b][1,2,4]triazine;
3-[1-(2,4-Dichlorophenyl)cyclopropyl]-6-(4-fluorophenyl)[1,2,4]triazolo[4,3-b][1,2,4]triazine;
3-[1-(3-Bromophenyl)cyclopropyl]-6-(4-fluorophenyl)[1,2,4]triazolo[4,3-b][1,2,4]triazine;
3-[1-(4-Bromophenyl)cyclopropyl]-6-(4-fluorophenyl)[1,2,4]triazolo[4,3-b][1,2,4]triazine;
3-[1-(2-Chlorophenyl)cyclopropyl]-6-(4-fluorophenyl)[1,2,4]triazolo[4,3-b][1,2,4]triazine;
6-(4-Fluorophenyl)-3-[1-(2-methoxyphenyl)cyclopropyl][1,2,4]triazolo[4,3-b][1,2,4]triazine;
6-(4-Fluorophenyl)-3-[1-(3-fluorophenyl)cyclopropyl][1,2,4]triazolo[4,3-b][1,2,4]triazine;
6-(4-Fluorophenyl)-3-{1-[3-(trifluoromethyl)phenyl]cyclopropyl}[1,2,4]triazolo[4,3-b][1,2,4]triazine;
3-[1-(2-Chloro-6-fluorophenyl)cyclopropyl]-6-(4-fluorophenyl)[1,2,4]triazolo[4,3-b][1,2,4]triazine;
3-[1-(1,3-Benzodioxol-5-yl)cyclopropyl]-6-(4-fluorophenyl)[1,2,4]triazolo[4,3-b][1,2,4]triazine;
4-{1-[6-(4-Fluorophenyl)[1,2,4]triazolo[4,3-b][1,2,4]triazin-3-yl]cyclopropyl}quinoline;
6-{1-[6-(4-Fluorophenyl)[1,2,4]triazolo[4,3-b][1,2,4]triazin-3-yl]cyclopropyl}quinoline;
6-{1-[6-(3-Bromophenyl)[1,2,4]triazolo[4,3-b][1,2,4]triazin-3-yl]cyclopropyl}quinoline;
6-{1-[6-(4-Bromophenyl)[1,2,4]triazolo[4,3-b][1,2,4]triazin-3-yl]cyclopropyl}quinoline;
3-[3-(1-Quinolin-6-ylcyclopropyl)[1,2,4]triazolo[4,3-b][1,2,4]triazin-6-yl]benzonitrile;
4-[3-(1-Quinolin-6-ylcyclopropyl)[1,2,4]triazolo[4,3-b][1,2,4]triazin-6-yl]benzonitrile;
3-[1-(4-Methoxyphenyl)cyclopropyl]-6-phenyl[1,2,4]triazolo[4,3-b][1,2,4]triazin-7-amine;
6-(4-Fluorophenyl)-3-[1-(4-methoxyphenyl)cyclopropyl][1,2,4]triazolo[4,3-b][1,2,4]triazin-7-amine;
6-{3-[1-(4-Methoxyphenyl)cyclopropyl][1,2,4]triazolo[4,3-b][1,2,4]triazin-6-yl}-1,3-benzothiazol-2-amine;
1-(4-{3-[1-(4-Methoxyphenyl)cyclopropyl][1,2,4]triazolo[4,3-b][1,2,4]triazin-6-yl}phenyl)pyrrolidin-2-one;
N-Cyclopropyl-4-{3-[1-(4-methoxyphenyl)cyclopropyl][1,2,4]triazolo[4,3-b][1,2,4]triazin-6-yl}benzamide;
4-{3-[1-(4-Methoxyphenyl)cyclopropyl][1,2,4]triazolo[4,3-b][1,2,4]triazin-6-yl}-N-(tetrahydro-2H-pyran-4-yl)benzamide;
N-(trans-4-Hydroxycyclohexyl)-4-3-[1-(4-methoxyphenyl)cyclopropyl][1,2,4]triazolo[4,3-b][1,2,4]triazin-6-ylbenzamide;
Ethyl 4-[(4-{3-[1-(4-methoxyphenyl)cyclopropyl][1,2,4]triazolo[4,3-b][1,2,4]triazin-6-yl}benzoyl)amino]piperidine-1-carboxylate;
4-{3-[1-(4-Methoxyphenyl)cyclopropyl][1,2,4]triazolo[4,3-b][1,2,4]triazin-6-yl}-N-(pyridin-2-ylmethyl)benzamide;
Ethyl 1-[(4-{3-[1-(4-methoxyphenyl)cyclopropyl][1,2,4]triazolo[4,3-b][1,2,4]triazin-6-yl}benzoyl)amino]cyclopropanecarboxylate;
N-[1-(6-Fluoropyridin-2-yl)pyrrolidin-3-yl]-4-{3-[1-(4-methoxyphenyl)cyclopropyl][1,2,4]triazolo[4,3-b][1,2,4]triazin-6-yl}benzamide;
4-{3-[1-(4-Methoxyphenyl)cyclopropyl][1,2,4]triazolo[4,3-b][1,2,4]triazin-6-yl-N'-pyridin-2-yl}benzohydrazide;
6-(1-{6-[3-(1H-imidazol-1-yl)phenyl][1,2,4]triazolo[4,3-b][1,2,4]triazin-3-yl}cyclopropyl)quinoline;
6-(1-{6-[4-(1H-imidazol-1-yl)phenyl][1,2,4]triazolo[4,3-b][1,2,4]triazin-3-yl}cyclopropyl)quinoline;
3-{4-[3-(1-Quinolin-6-ylcyclopropyl)[1,2,4]triazolo[4,3-b][1,2,4]triazin-6-yl]phenyl}-1,3-oxazolidin-2-one;
6-(1-{6-[3-(6-Methoxypyridin-3-yl)phenyl][1,2,4]triazolo[4,3-b][1,2,4]triazin-3-yl}cyclopropyl)quinoline;
N,N-Dimethyl-5-{3-[3-(1-quinolin-6-ylcyclopropyl)[1,2,4]triazolo[4,3-b][1,2,4]triazin-6-yl]phenyl}pyridine-2-carboxamide;
N-Ethyl-5-{3-[3-(1-quinolin-6-ylcyclopropyl)[1,2,4]triazolo[4,3-b][1,2,4]triazin-6-yl]phenyl}pyridine-2-carboxamide;
N-Methyl-2-(4-{3-[3-(1-quinolin-6-ylcyclopropyl)[1,2,4]triazolo[4,3-b][1,2,4]triazin-6-yl]phenyl}-1H-pyrazol-1-yl)acetamide;
2-(4-{3-[3-(1-Quinolin-6-ylcyclopropyl)[1,2,4]triazolo[4,3-b][1,2,4]triazin-6-yl]phenyl}-1H-pyrazol-1-yl)-N-(tetrahydrofuran-3-yl)acetamide;
N-(1-Pyridin-2-ylethyl)-2-(4-{3-[3-(1-quinolin-6-ylcyclopropyl)[1,2,4]triazolo[4,3-b][1,2,4]triazin-6-yl]phenyl}-1H-pyrazol-1-yl)acetamide;

N,N-Dimethyl-2-(4-{3-[3-(1-quinolin-6-ylcyclopropyl)[1,2,4]triazolo[4,3-b][1,2,4]triazin-6-yl]phenyl}-1H-pyrazol-1-yl)acetamide;
N-Methyl-2-(4-{4-[3-(1-quinolin-6-ylcyclopropyl)[1,2,4]triazolo[4,3-b][1,2,4]triazin-6-yl]phenyl}-1H-pyrazol-1-yl)acetamide;
N-Isopropyl-2-(4-{4-[3-(1-quinolin-6-ylcyclopropyl)[1,2,4]triazolo[4,3-b][1,2,4]triazin-6-yl]phenyl}-1H-pyrazol-1-yl)acetamide;
N-(Cyclopropylmethyl)-2-(4-{4-[3-(1-quinolin-6-ylcyclopropyl)[1,2,4]triazolo[4,3-b][1,2,4]triazin-6-yl]phenyl}-1H-pyrazol-1-yl)acetamide;
N-Isopropyl-2-methyl-2-(4-{4-[3-(1-quinolin-6-ylcyclopropyl)[1,2,4]triazolo[4,3-b][1,2,4]triazin-6-yl]phenyl}-1H-pyrazol-1-yl)propanamide;
6-[1-(6-{4-[1-(1,1-Dimethyl-2-oxo-2-pyrrolidin-1-ylethyl)-1H-pyrazol-4-yl]phenyl}[1,2,4]triazolo[4,3-b][1,2,4]triazin-3-yl)cyclopropyl]quinoline;
(2R)—N,N-Dimethyl-2-(4-{4-[3-(1-quinolin-6-ylcyclopropyl)[1,2,4]triazolo[4,3-b][1,2,4]triazin-6-yl]phenyl}-1H-pyrazol-1-yl)propanamide;
(2S)—N,N-Dimethyl-2-(4-{4-[3-(1-quinolin-6-ylcyclopropyl)[1,2,4]triazolo[4,3-b][1,2,4]triazin-6-yl]phenyl}-1H-pyrazol-1-yl)propanamide;
6-(3-Bromophenyl)-3-[1-(3-methyl[1,2,4]triazolo[4,3-a]pyridin-6-yl)cyclopropyl][1,2,4]triazolo[4,3-b][1,2,4]triazine;
6-1-[6-(4-Bromo-3-fluorophenyl)[1,2,4]triazolo[4,3-b][1,2,4]triazin-3-yl]cyclopropylquinoline;
6-(1-{6-[3-Fluoro-4-(1H-imidazol-1-yl)phenyl][1,2,4]triazolo[4,3-b][1,2,4]triazin-3-yl}cyclopropyl)quinoline;
5-{2-Fluoro-4-[3-(1-quinolin-6-ylcyclopropyl)[1,2,4]triazolo[4,3-b][1,2,4]triazin-6-yl]phenyl}-N,N-dimethylpyridine-2-carboxamide;
5-{2-Fluoro-4-[3-(1-quinolin-6-ylcyclopropyl)[1,2,4]triazolo[4,3-b][1,2,4]triazin-6-yl]phenyl}pyridin-2-amine;
Methyl (5-{2-fluoro-4-[3-(1-quinolin-6-ylcyclopropyl)[1,2,4]triazolo[4,3-b][1,2,4]triazin-6-yl]phenyl}pyridin-2-yl)carbamate;
3-[1-(1,3-Benzothiazol-6-yl)cyclopropyl]-6-(4-bromophenyl)[1,2,4]triazolo[4,3-b][1,2,4]triazine;
4-{3-[1-(1,3-Benzothiazol-6-yl)cyclopropyl][1,2,4]triazolo[4,3-b][1,2,4]triazin-6-yl}-N-{(1S)-1-[(dimethylamino)carbonyl]propyl}benzamide;
4-{3-[1-(1,3-Benzothiazol-6-yl)cyclopropyl][1,2,4]triazolo[4,3-b][1,2,4]triazin-6-yl}-N-{(1S)-1-[(dimethylamino)carbonyl]-2-methylpropyl}benzamide;
4-{3-[1-(1,3-Benzothiazol-6-yl)cyclopropyl][1,2,4]triazolo[4,3-b][1,2,4]triazin-6-yl}-N-{(1S)-1-[(dimethylamino)carbonyl]-2,2-dimethylpropyl}benzamide;
6-(1-{6-[4-(1-Methyl-1H-pyrazol-4-yl)phenyl][1,2,4]triazolo[4,3-b][1,2,4]triazin-3-yl}cyclopropyl)quinoline;
N-Methyl-5-{4-[3-(1-quinolin-6-ylcyclopropyl)[1,2,4]triazolo[4,3-b][1,2,4]triazin-6-yl]phenyl}pyridine-2-carboxamide;
N,N-Dimethyl-5-{4-[3-(1-quinolin-6-ylcyclopropyl)[1,2,4]triazolo[4,3-b][1,2,4]triazin-6-yl]phenyl}pyridine-2-carboxamide;
6-(1-{6-[4-(1H-pyrazol-1-yl)phenyl][1,2,4]triazolo[4,3-b][1,2,4]triazin-3-yl}cyclopropyl)quinoline;
N-(Cyclopropylmethyl)-4-[3-(1-quinolin-6-ylcyclopropyl)[1,2,4]triazolo[4,3-b][1,2,4]triazin-6-yl]benzamide;
N-Ethyl-4-[3-(1-quinolin-6-ylcyclopropyl)[1,2,4]triazolo[4,3-b][1,2,4]triazin-6-yl]benzamide;
N,N-Dimethyl-4-[3-(1-quinolin-6-ylcyclopropyl)[1,2,4]triazolo[4,3-b][1,2,4]triazin-6-yl]benzamide;
N-Cyclopropyl-4-[3-(1-quinolin-6-ylcyclopropyl)[1,2,4]triazolo[4,3-b][1,2,4]triazin-6-yl]benzamide;
N-(Pyridin-2-ylmethyl)-4-[3-(1-quinolin-6-ylcyclopropyl)[1,2,4]triazolo[4,3-b][1,2,4]triazin-6-yl]benzamide;
Ethyl 4-{4-[3-(1-Quinolin-6-ylcyclopropyl)[1,2,4]triazolo[4,3-b][1,2,4]triazin-6-yl]benzoyl}piperazine-1-carboxylate;
6-(1-{6-[4-(Pyrrolidin-1-ylcarbonyl)phenyl][1,2,4]triazolo[4,3-b][1,2,4]triazin-3-yl}cyclopropyl)quinoline;
6-[1-(6-{4-[(3,3-Difluoropyrrolidin-1-yl)carbonyl]phenyl}[1,2,4]triazolo[4,3-b][1,2,4]triazin-3-yl)cyclopropyl]quinoline;
6-{1-[6-(4-{[(3-(3-Fluorophenyl)pyrrolidin-1-yl]carbonyl}phenyl)[1,2,4]triazolo[4,3-b][1,2,4]triazin-3-yl]cyclopropyl}quinoline;
6-{1-[6-(4-{[(3S)-3-Fluoropyrrolidin-1-yl]carbonyl}phenyl)[1,2,4]triazolo[4,3-b][1,2,4]triazin-3-yl]cyclopropyl}quinoline;
4-[3-(1-Quinolin-6-ylcyclopropyl)[1,2,4]triazolo[4,3-b][1,2,4]triazin-6-yl]-N-[(2S)-tetrahydrofuran-2-ylmethyl]benzamide;
N-(1-Pyridin-2-ylcyclopropyl)-4-[3-(1-quinolin-6-ylcyclopropyl)[1,2,4]triazolo[4,3-b][1,2,4]triazin-6-yl]benzamide;
N-(1S)-2,2-Dimethyl-1-[(methylamino)carbonyl]propyl-4-[3-(1-quinolin-6-ylcyclopropyl)[1,2,4]triazolo[4,3-b][1,2,4]triazin-6-yl]benzamide;
N-{(1S)-1-[(Dimethylamino)carbonyl]-2,2-dimethylpropyl}-4-[3-(1-quinolin-6-ylcyclopropyl)[1,2,4]triazolo[4,3-b][1,2,4]triazin-6-yl]benzamide;
N-[(1S)-1-(Azetidin-1-ylcarbonyl)-2,2-dimethylpropyl]-4-[3-(1-quinolin-6-ylcyclopropyl)[1,2,4]triazolo[4,3-b][1,2,4]triazin-6-yl]benzamide;
N-[(1S)-2-Amino-1-methyl-2-oxoethyl]-4-[3-(1-quinolin-6-ylcyclopropyl)[1,2,4]triazolo[4,3-b][1,2,4]triazin-6-yl]benzamide;
N-[(1S)-1-(Aminocarbonyl)-2-methylpropyl]-4-[3-(1-quinolin-6-ylcyclopropyl)[1,2,4]triazolo[4,3-b][1,2,4]triazin-6-yl]benzamide;
N-Ethyl-2-fluoro-4-[3-(1-quinolin-6-ylcyclopropyl)[1,2,4]triazolo[4,3-b][1,2,4]triazin-6-yl]benzamide;
2-Fluoro-N-methyl-4-[3-(1-quinolin-6-ylcyclopropyl)[1,2,4]triazolo[4,3-b][1,2,4]triazin-6-yl]benzamide;
2-Fluoro-N-(trans-4-hydroxycyclohexyl)-4-[3-(1-quinolin-6-ylcyclopropyl)[1,2,4]triazolo[4,3-b][1,2,4]triazin-6-yl]benzamide;
2-Fluoro-N-(2-methoxy-1,1-dimethylethyl)-4-[3-(1-quinolin-6-ylcyclopropyl)[1,2,4]triazolo[4,3-b][1,2,4]triazin-6-yl]benzamide;
N-Cyclopropyl-2-fluoro-4-[3-(1-quinolin-6-ylcyclopropyl)[1,2,4]triazolo[4,3-b][1,2,4]triazin-6-yl]benzamide;
2-Fluoro-4-[3-(1-quinolin-6-ylcyclopropyl)[1,2,4]triazolo[4,3-b][1,2,4]triazin-6-yl]benzamide;
2-Fluoro-N,N-dimethyl-4-[3-(1-quinolin-6-ylcyclopropyl)[1,2,4]triazolo[4,3-b][1,2,4]triazin-6-yl]benzamide;
6-(1-{6-[3-Fluoro-4-(pyrrolidin-1-ylcarbonyl)phenyl][1,2,4]triazolo[4,3-b][1,2,4]triazin-3-yl}cyclopropyl)quinoline;
N-Methyl-N-2-[methyl(pyridin-2-yl)amino]ethyl-4-[3-(1-quinolin-6-ylcyclopropyl)[1,2,4]triazolo[4,3-b][1,2,4]triazin-6-yl]benzamide;
N-[(1R)-1-(4-Methyl-1,3-thiazol-2-yl)ethyl]-4-[3-(1-quinolin-6-ylcyclopropyl)[1,2,4]triazolo[4,3-b][1,2,4]triazin-6-yl]benzamide;

or pharmaceutically acceptable salt thereof.

* * * * *

UNITED STATES PATENT AND TRADEMARK OFFICE
CERTIFICATE OF CORRECTION

PATENT NO. : 8,143,251 B2
APPLICATION NO. : 13/033918
DATED : March 27, 2012
INVENTOR(S) : Jincong Zhuo et al.

It is certified that error appears in the above-identified patent and that said Letters Patent is hereby corrected as shown below:

In Claim 1, Col. 105, line 19, delete "C(O)NR$^C$R$^B$," and insert --C(O)NR$^C$R$^D$,--, therefor.

In Claim 1, Col. 106, line 4, delete "C(O)OR$^i$," and insert --C(O)OR$^j$,--, therefor.

In Claim 1, Col. 106, line 33, delete "S(O)R$^{h2}$," and insert --S(O)R$^{b2}$,--, therefor.

In Claim 1, Col. 107, line 64, delete "R$^{dl}$" and insert --R$^{d1}$--, therefor.

In Claim 1, Col. 108, line 59, delete "5 W'—X'—Y'—Z'" and insert --5 —W'—X'—Y'—Z'--, therefor.

In Col. 11, lines 59-66 should read,

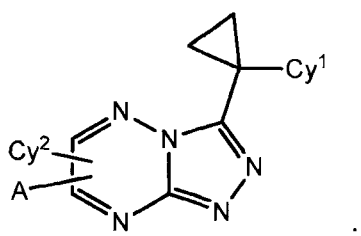

II

In Col. 12, lines 13-19 should read,

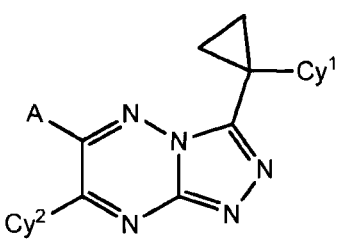

IIIb

Signed and Sealed this
Second Day of October, 2012

David J. Kappos
*Director of the United States Patent and Trademark Office*

CERTIFICATE OF CORRECTION (continued)
U.S. Pat. No. 8,143,251 B2

In Scheme 4, chemical structure 7 should read,

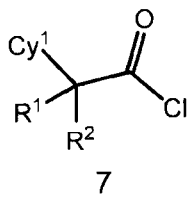

7

In Schemes 4, 6, and 7, chemical structure 5 should read,

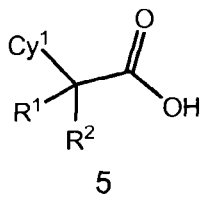

5

In Claim 15, Col. 109, lines 44-51 should read.

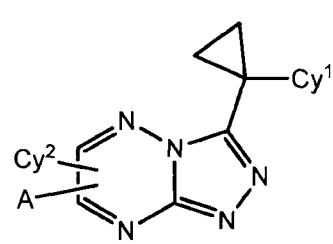

II

In Claim 16, Col. 110, lines 1-9 should read,

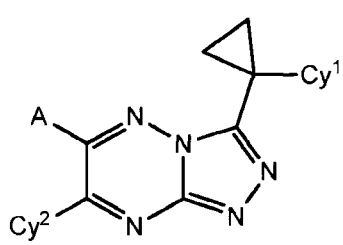

IIIb